US011981943B2

(12) United States Patent
Mahajan et al.

(10) Patent No.: US 11,981,943 B2
(45) Date of Patent: May 14, 2024

(54) METHODS AND COMPOSITION FOR DETECTING CAPN5

(71) Applicant: UNIVERSITY OF IOWA RESEARCH FOUNDATION, Iowa City, IA (US)

(72) Inventors: Vinit B. Mahajan, Iowa City, IA (US); Alexander G. Bassuk, Iowa City, IA (US); Diana F. Colgan, Iowa City, IA (US); Gabriel Velez, Iowa City, IA (US); Kellie Schaefer, Iowa City, IA (US); Marcus Toral, Iowa City, IA (US); Shu Wu, Iowa City, IA (US); Lokesh Gakhar, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 867 days.

(21) Appl. No.: 16/340,657

(22) PCT Filed: Oct. 2, 2017

(86) PCT No.: PCT/US2017/054727
§ 371 (c)(1),
(2) Date: Apr. 9, 2019

(87) PCT Pub. No.: WO2018/071216
PCT Pub. Date: Apr. 19, 2018

(65) Prior Publication Data
US 2019/0284544 A1 Sep. 19, 2019

Related U.S. Application Data

(60) Provisional application No. 62/406,806, filed on Oct. 11, 2016, provisional application No. 62/525,510, filed on Jun. 27, 2017.

(51) Int. Cl.
| | |
|---|---|
| *C12N 9/64* | (2006.01) |
| *A61K 9/08* | (2006.01) |
| *A61K 38/00* | (2006.01) |
| *A61P 27/02* | (2006.01) |
| *A61P 29/00* | (2006.01) |
| *C07K 14/49* | (2006.01) |
| *C07K 14/81* | (2006.01) |
| *G01N 33/573* | (2006.01) |
| *C07K 7/64* | (2006.01) |

(52) U.S. Cl.
CPC ............. *C12N 9/6472* (2013.01); *A61K 9/08* (2013.01); *A61P 27/02* (2018.01); *A61P 29/00* (2018.01); *C07K 14/49* (2013.01); *C07K 14/81* (2013.01); *C07K 14/8139* (2013.01); *C12Y 304/22* (2013.01); *G01N 33/573* (2013.01); *A61K 38/00* (2013.01); *C07K 7/64* (2013.01); *C07K 2319/00* (2013.01)

(58) Field of Classification Search
None
See application file for complete search history.

(56) References Cited

U.S. PATENT DOCUMENTS

| 5,869,336 A | 2/1999 | Meyer et al. |
|---|---|---|
| 6,235,481 B1 | 5/2001 | Horikawa et al. |
| 6,569,665 B1* | 5/2003 | Boehm .................... C12Q 1/37 435/226 |
| 2002/0150885 A1* | 10/2002 | Weber .................. G01N 33/533 435/5 |
| 2003/0003477 A1 | 1/2003 | Kapeller-Libermann et al. |
| 2003/0114373 A1 | 6/2003 | Chen et al. |
| 2004/0014093 A1 | 1/2004 | Duclos et al. |
| 2009/0312265 A1* | 12/2009 | Schmidtchen .......... A61P 15/02 530/331 |
| 2010/0233079 A1 | 9/2010 | Jakob et al. |
| 2012/0087862 A1 | 4/2012 | Hood et al. |
| 2012/0240246 A1 | 9/2012 | Moldoveanu |

FOREIGN PATENT DOCUMENTS

JP 2002241304 A 8/2002

OTHER PUBLICATIONS

Guo et al., PNAS, Jun. 2004 101(25) 9205-9210 (Year: 2004).*
Huang et al., Investigative Ophthalmology & Visual Science, Jun. 2010, vol. 51, No. 6, 3049-3054 (Year: 2010).*
Lehrer et al., Ji. Immun. Methods 137(2) 1991, 167-173 (Year: 1991).*
Yampolsky, Genetics 170: 1459-1472 2005 (Year: 2005).*
Betts and Russel, Chapter 14 of Bioinformatics for Geneticists, 2003, 289-316 (Year: 2003).*
Bowie et al., Science 247, 1990, pp. 1306-1311 (Year: 1990).*
Uniprot O15484, version 135 entered Mar. 16, 2016, 4 pages, downloaded Mar. 7, 2022 from www.uniprot.org (Year: 2016).*
Wenschuh et al., Rapid Communications in Mass Spectrometry, vol. 12, 115-119 (1998) (Year: 1998).*
Wert et al., Human Mutation 2019; 1-16 (Year: 2019).*
Bassuk, A , et al., "Structural Modeling of a Novel CAPN 5 mutation that causes uveitis and neovascular detachment", PLOS One, DOI:10.1371/journal.pone.0122352, 11 pages (Apr. 9, 2015).
Charm, A , et al., "Secondary glaucoma in CAPN5-associated neovascular inflammatory vitreoretinopathy", Clin Ophthalmol 10, 1187-1197 (2016).
Gakhar, L , et al., "Small-angle x-ray scattering of calpain-5 reveals a highly open conformation among calpains", J Struct Biol 196(3), 309-318 (2016).
Nelson, N , et al., "CAPN5 gene silencing by short hairpin RNA interference", BMC Res Notes 7, 642, 7 pages (2014).
Patent Cooperation Treaty , International Searching Authority, Search Report and Written Opinion for PCT/US2017/054727, 9 pages, dated Feb. 1, 2018.

(Continued)

*Primary Examiner* — Melissa L Fisher
*Assistant Examiner* — Joseph Fischer
(74) *Attorney, Agent, or Firm* — Viksnins Harris Padys Malen LLP

(57) ABSTRACT

The present disclosure provides CAPN5 substrates and CAPN5 inhibitors, nucleic acids encoding CAPN5 substrates or CAPN5 inhibitors, methods to deliver CAPN5 substrate or CAPN5 inhibitor agents to the eye, and methods of identifying inhibitors of CAPN5.

14 Claims, 24 Drawing Sheets

Specification includes a Sequence Listing.

(56) References Cited

OTHER PUBLICATIONS

Schaefer, K., et al., "Calpain-5 gene expression in the mouse eye and brain", J Invest Ophthalmol Vis Sci 57, 2509-2521 (2016).

Schaefer, K., et al., "CAPN5 proteolysis and release of angiogenic growth factors from cells leads to eye phenotype", Biology of Calpains in Health and Disease Conference in Asilomar, CA, Abstract, 1 page (Jul. 16, 2019).

Velez, G., et al., "Structure-function relationships in a non-classical calpain associated with neuroinflammation", Biology of Calpains in Health and Disease Conference in Asilomar, CA, Abstract, 1 page (Jul. 15, 2019).

Wert, K., et al., "CAPN5 genetic inactivation phenotype supports therapeutic inhibition trials", Human Mutation 1-16 (2019).

Wert, K., et al., "CAPN5 mutation in hereditary uveitis: the R243L mutation increases calpain catalytic activity and triggers intraocular inflammation in a mouse model", Human Molecular Genetics 24(16), 4584-4598 (2015).

* cited by examiner

FIG 1. CAPN5 HAS TWO AUTOPROTEOLYSIS SITES. A. CALCIUM-ACTIVATED CAPN5 AUTOPROTEOLYSIS RELEASES A 60 kDa AND 45 kDa FRAGMENT. B. SBP-TAGGED CAPN5-PC (WT, AND R243L) INCUBATED WITH 1mM CALCIUM PRODUCED 60 kDa FRAGMENTS. R243L CAPN5 PRODUCED THE 60 kDa FRAGMENT AT EARLIER TIME POINTS THAN WT.

Figures 5A

CAPN5-370-380 ALIGNMENT

| | | | | | | | | | | | | | | | | | | | | | | | |
|---|---|---|---|---|---|---|---|---|---|---|---|---|---|---|---|---|---|---|---|---|---|---|---|
| CAPN1  | R | G | S | T | A | G | G | C | R | N | - | Y | P | A | T | F | W | V | N | P | Q | F | K |
| CAPN2  | R | G | S | T | A | G | G | C | R | N | - | Y | P | N | T | F | W | M | N | P | Q | Y | L |
| CAPN3  | R | G | C | S | A | G | G | C | R | N | - | F | P | D | T | F | W | T | N | P | Q | Y | R |
| CAPN5  | R | Q | N | R | G | G | C | I | N | - | H | K | D | T | F | Q | N | P | Q | Y | I | | |
| CAPN6  | L | M | N | R | S | G | G | C | Y | N | - | N | R | D | T | F | L | Q | N | P | Q | Y | I |
| CAPN8  |   | G | S | T | A | G | G | C | Q | N | - | Y | P | A | T | Y | W | T | N | P | Q | F | K |
| CAPN9  |   | G | S | T | A | G | G | C | R | N | - | F | L | D | T | F | W | T | N | P | Q | I | K |
| CAPN11 | R | G | S | S | A | G | G | C | R | N | - | H | P | G | T | F | W | T | N | P | Q | F | K |
| CAPN12 | R | G | F | N | S | G | S | Q | P | - | N | A | E | T | F | W | T | N | P | Q | F | R | |
| CAPN13 | L | G | N | T | A | G | G | P | R | N | D | A | Q | F | N | F | S | V | Q | E | P | M | E |
| CAPN14 | K | R | S | T | A | G | G | Q | R | Q | L | L | Q | D | T | F | W | K | N | P | Q | F | L |

Figures 5B

CAPN5-370-380 ALIGNMENT

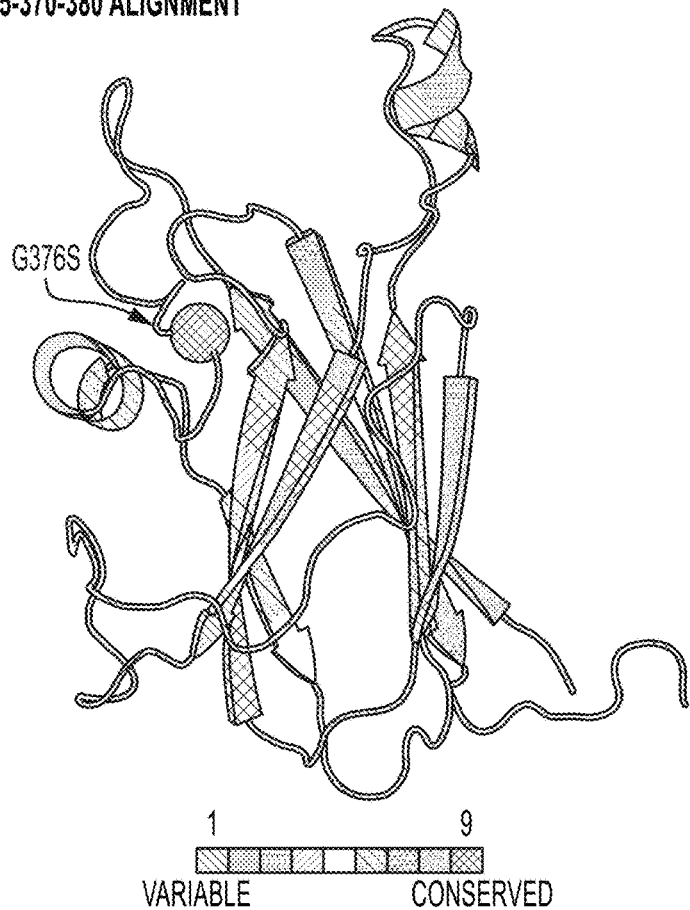

G376S

1 — 9
VARIABLE — CONSERVED

| PEPTIDE | PROTEASE: CAPN5 | | |
|---|---|---|---|
| | Vmax | Km | Ki |
| CAPN5 (372-378) | 0.3657 +/- 0.05283 | 20.29 +/- 8.444 | - |
| CAPN5 (370-380) | 2.071 +/- 0.401 | 16.46 +/- 4.925 | 43.17 +/- 14.02 |
| CAPN5 (370-390) | 1.424 +/- 0.2138 | 79 +/- 21.47 | - |

Figure 13A
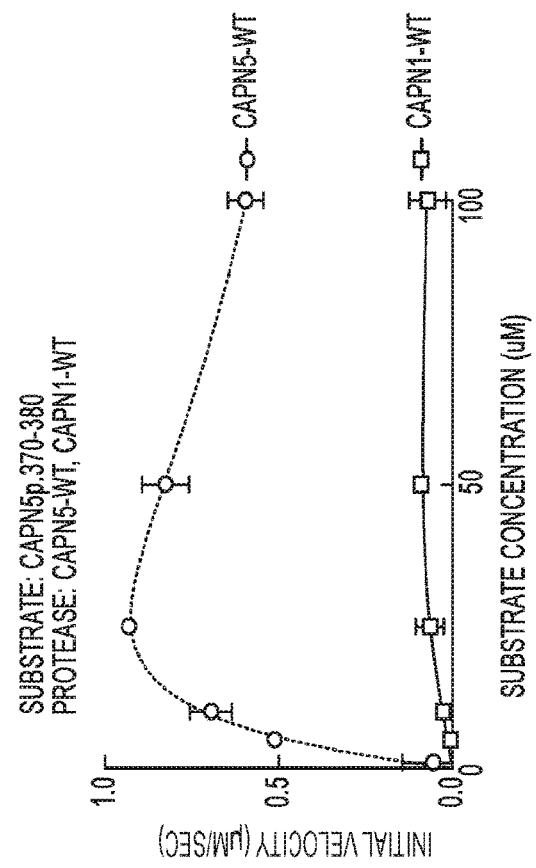
Figure 13B
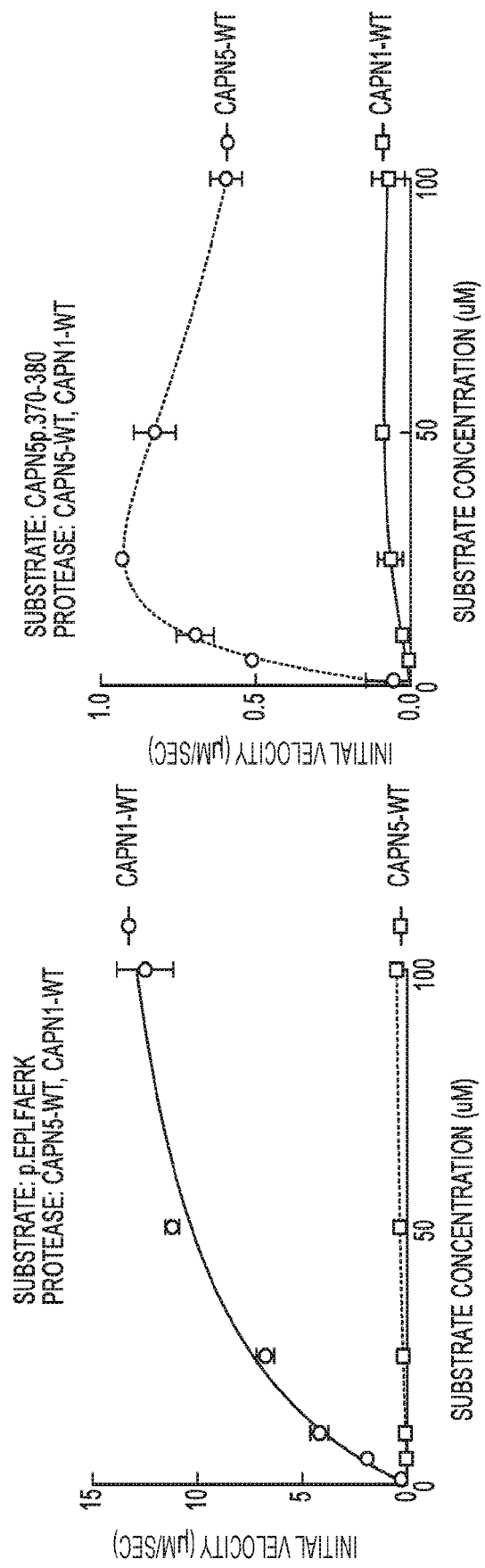
Figure 13C
| PEPTIDE | PROTEASE: CAPN1 | | PROTEASE: CAPN5 | | |
|---|---|---|---|---|---|
| | Vmax | Km | Vmax | Km | Ki |
| CAPN5 (370-380) | - | - | 2.071 +/- 0.401 | 16.46 +/- 4.925 | 43.17 +/- 14.02 |
| EPLFAERK | 17.29 +/- 1.072 | 33.76 +/- 5.084 | 0.9432 +/- 0.1193 | 79.34 +/- 18.14 | - |

ALIGNMENT OF CALPAIN FAMILY PEPTIDES

| | | | | | | | | | | | |
|---|---|---|---|---|---|---|---|---|---|---|---|
| CAPN5 | R | Q | N | R | G | G | C | I | N | H | |
| CAPN1/CAPN2 | R | G | S | T | A | G | G | C | R | N | Y |
| CAPN3 | R | G | C | S | A | G | G | C | R | N | F |
| CAPN6 | L | M | N | R | S | G | G | C | Y | N | N |
| CAPN7 | | G | Q | S | A | G | G | C | G | N | F |
| CAPN9 | | G | S | T | A | G | G | C | R | N | F L |
| CAPN10 | | G | Q | S | A | G | G | C | R | N | N |
| CAPN12 | R | G | F | N | S | G | G | S | Q | P | N |
| CAPN13 | L | G | N | T | A | G | G | P | R | N | D |
| CAPN14 | K | R | S | T | A | G | G | Q | R | Q | L |

Fig. 14A

CALPAIN FAMILY PEPTIDES KINETICS

| PEPTIDE | PROTEASE: CAPN1 | | | PROTEASE: CAPN5 | | |
|---|---|---|---|---|---|---|
| | Vmax | Km | | Vmax | Km | Ki |
| CAPN1/CAPN2 | 0.1685 +/- 0.07611 | 26.09 +/- 32.05 | | 0.3926 +/- 0.1802 | 127.1 +/- 93.15 | - |
| CAPN3 | - | - | | - | - | - |
| CAPN5 | - | - | | 2.071 +/- 0.401 | 16.46 +/- 4.925 | 43.17 +/- 14.02 |
| CAPN6 | - | - | | - | - | - |
| CAPN7 | - | - | | 0.3069 +/- 2.142 | 819.6 +/- 6304 | - |
| CAPN9 | - | - | | - | - | - |
| CAPN10 | 0.3672 +/- 0.1277 | 138.9 +/- 73.33 | | 0.2188 +/- 0.04303 | 51.44 +/- 21.21 | - |
| CAPN12 | - | - | | - | - | - |
| CAPN13 | - | - | | - | - | - |
| CAPN14 | 0.1973 +/- 0.08071 | 175.1 +/- 102.2 | | 0.2357 +/- 0.04566 | 0.4546 +/- 0.8602 | - |

Figure 14D

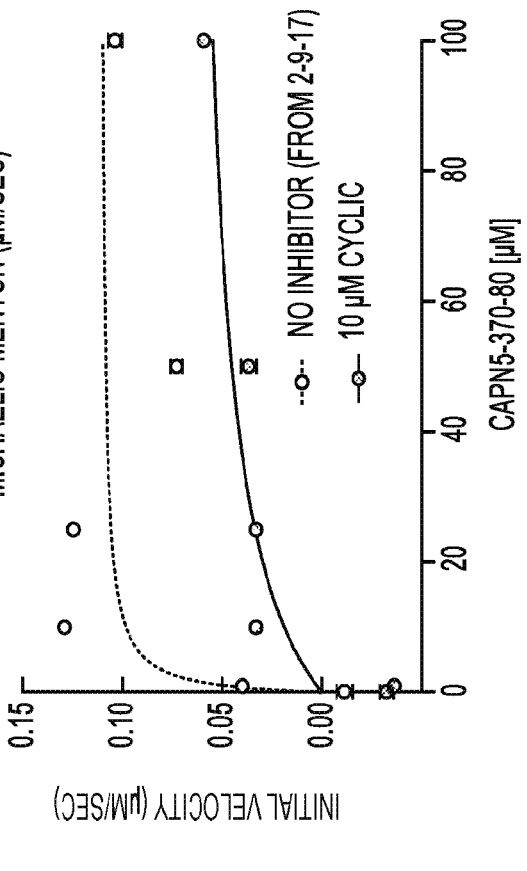
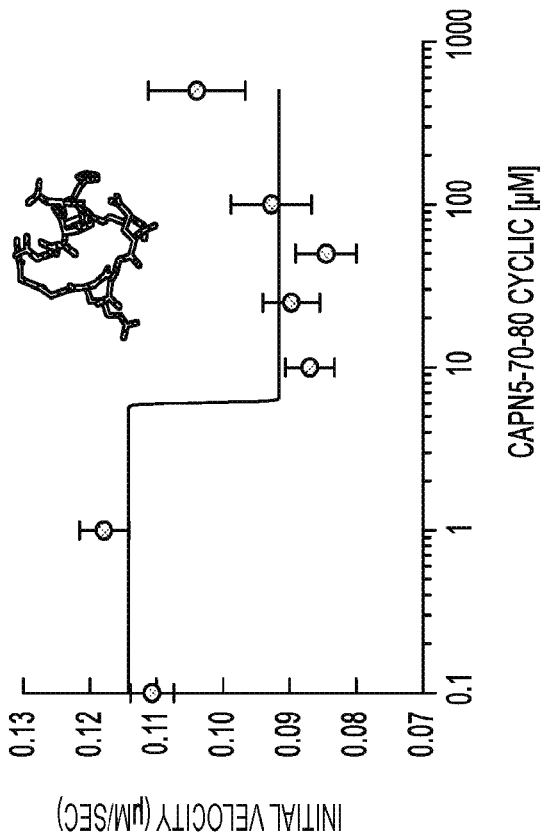
Figure 16B
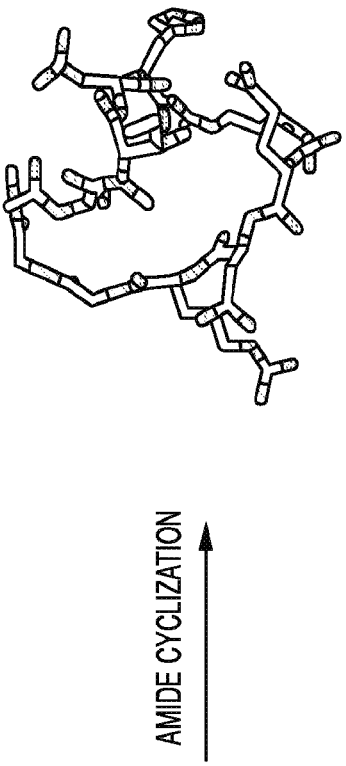
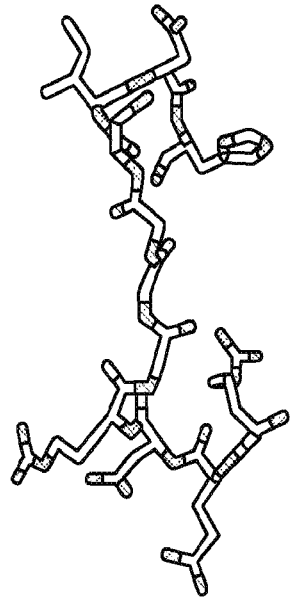
Figure 16A

BIOPHYSICAL CHARACTERIZATION OF CAPN5-p.370-80 PEPTIDE COMPLEX.

CO-CRYSTALLIZATION OF CAPN5 WITH CAPN5 p. 370-80 PEPTIDE.

MODIFICATION OF LEAD COMPOUND REDUCES ACTIVITY

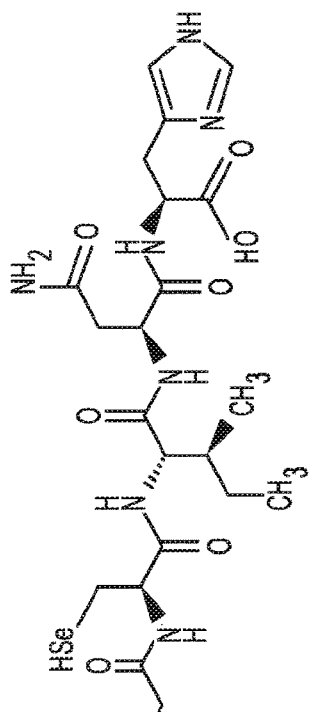
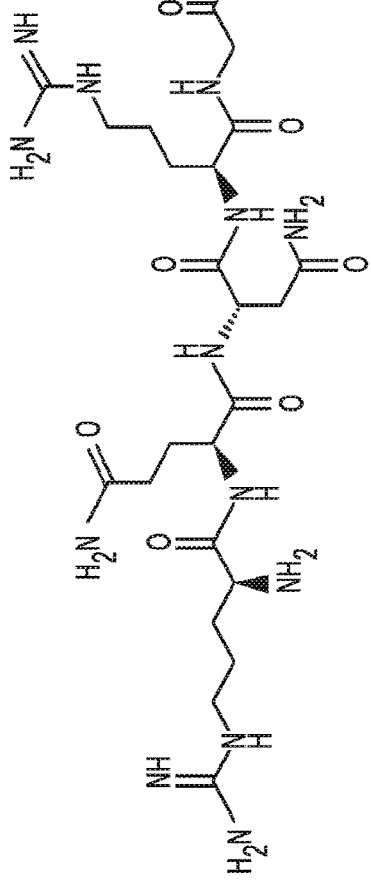
RQNRGGGCINH
NO MODIFICATION
Figure 19A
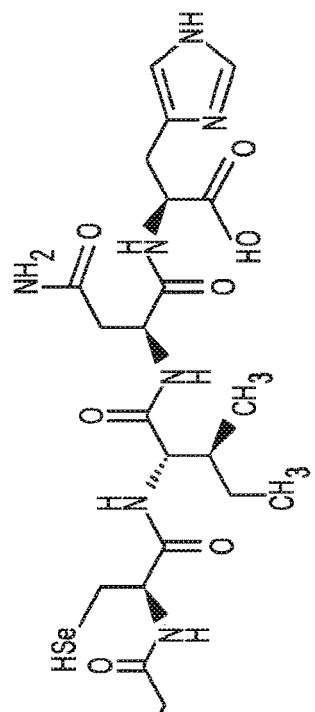
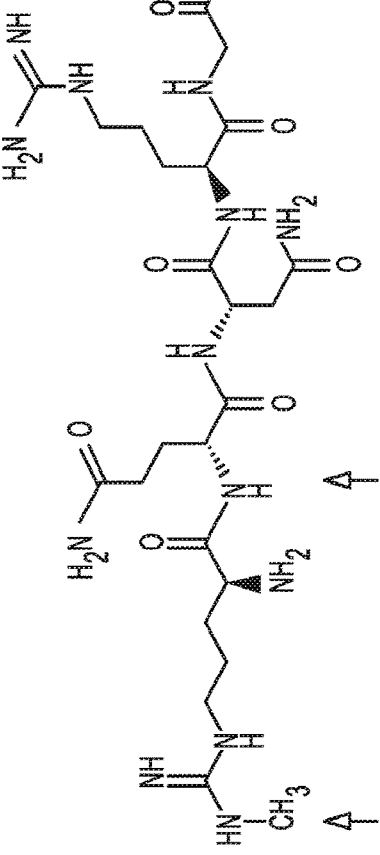
Pep-1-Mod
Methy-Arginine   D-Glutamine
Figure 19B

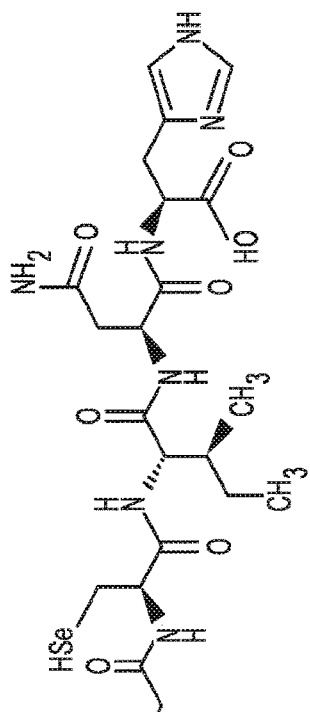
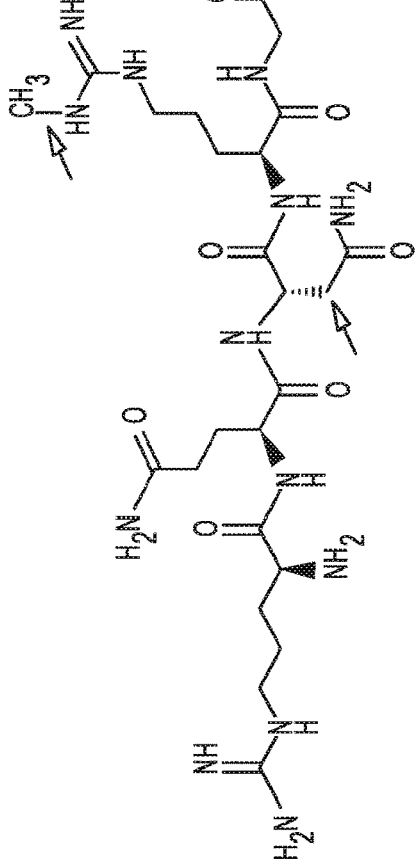
Figure 19C
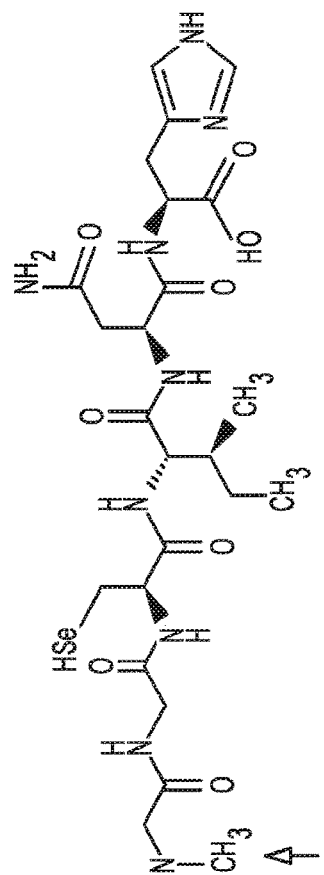
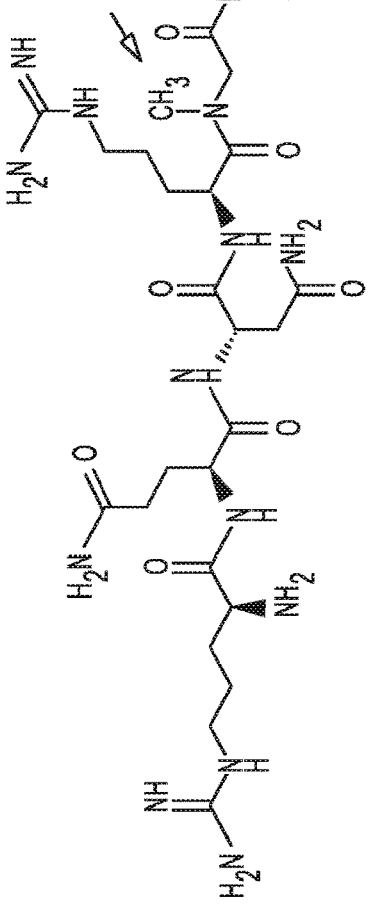
Figure 19D

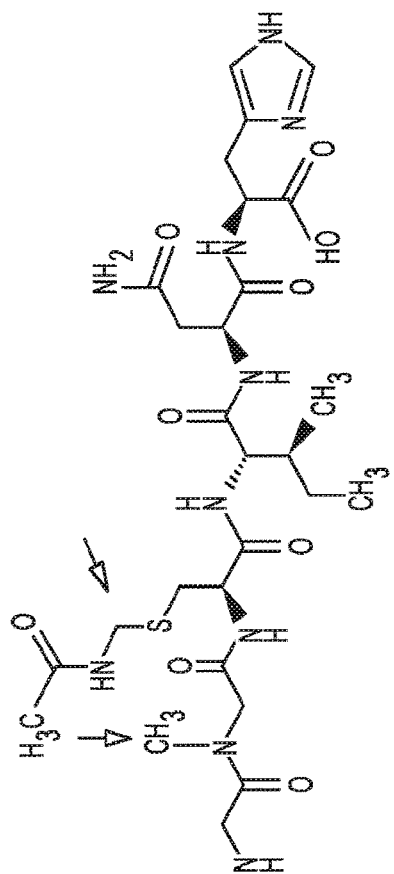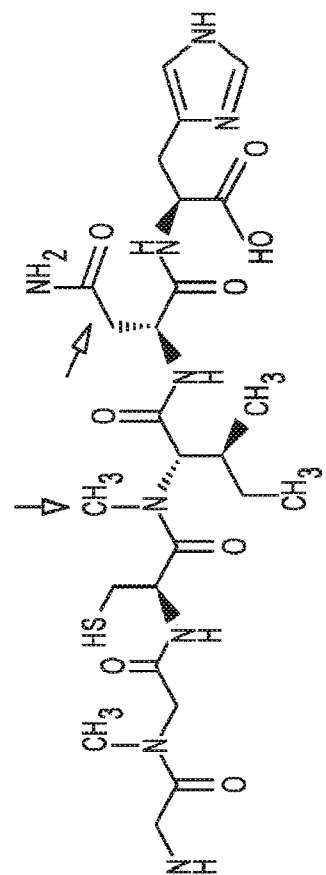
Figure 19E
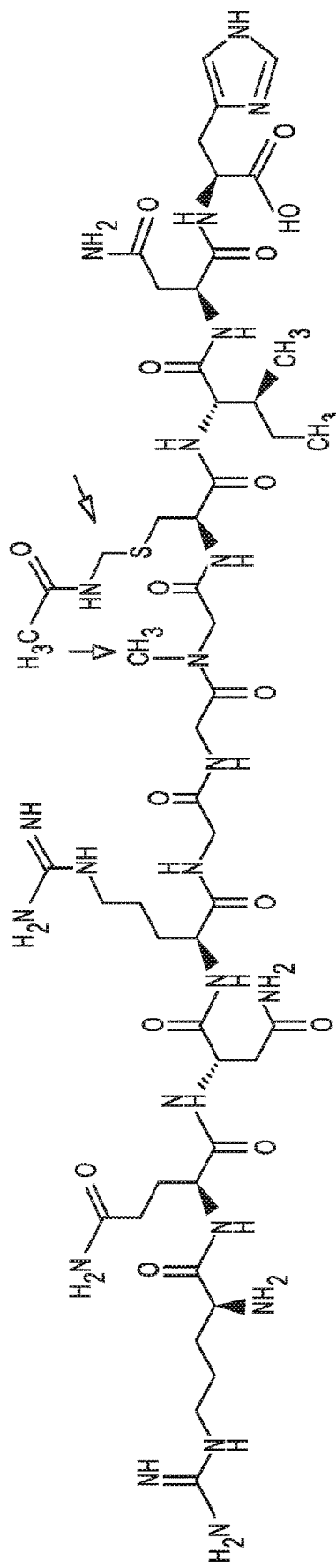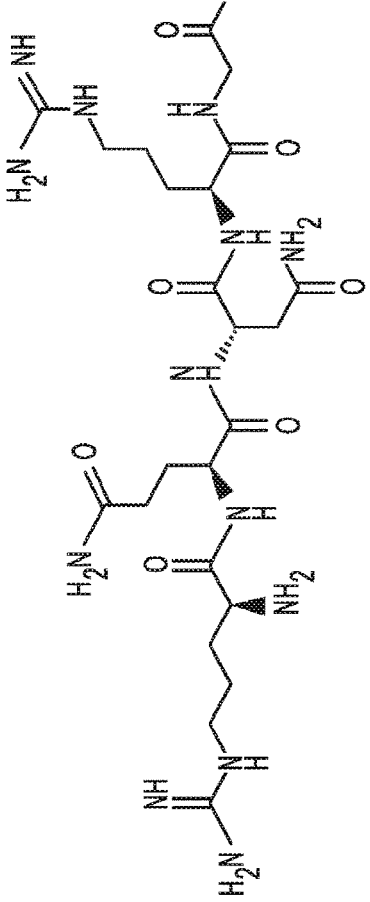
Figure 19F

METHODS AND COMPOSITION FOR DETECTING CAPN5

RELATED APPLICATIONS

This application claims priority to U.S. Provisional Application Ser. No. 62/406,806 that was filed on Oct. 11, 2016, and U.S. Provisional Application Ser. No. 62/525,510 that was filed on Jun. 27, 2017. The entire content of the applications referenced above are hereby incorporated by reference herein.

STATEMENT REGARDING FEDERALLY SPONSORED RESEARCH

This invention was made with government support under RO1 EY024665 and RO1 EY025225 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 2, 2017, is named 17023_203WO1_SL.txt and is 47,129 bytes in size.

INTRODUCTION

Uveitis (intraocular inflammation) remains a common yet difficult-to-treat cause of visual loss in all ages, for which the molecular cause is unknown.

Autosomal Dominant Neovascular Inflammatory Vitreoretinopathy (ADNIV) is an inherited disease characterized by retinal and iris neovascularization, abnormal retinal pigmentation, anterior chamber and vitreous inflammation, cystoid macular edema, vitreous hemorrhage, and traction retinal detachment. Mutations in the CAPN5 gene cause ADNIV. CAPN5 is the first nonsyndromic gene for autoimmune uveitis, and among the very few Mendelian autoimmune diseases where the gene is identified. CAPN5 encodes the protease calpain-5, a calcium-activated intracellular cysteine protease, which is expressed in many tissues including photoreceptors and their nuclei. It is one of 16 calpain proteases, which cleave subdomains from target proteins to irreversibly change their function. The disease mechanisms are not understood, but the disease mimics several common diseases such as diabetic retinopathy, retinitis pigmentosa, and proliferative vitreoretinopathy.

Therapies for genetic diseases of the eye, including ADNIV, need to be developed.

SUMMARY

The present inventors have discovered therapeutic agents, such as peptides, that inhibit the CAPN5 enzyme. The present invention provides therapies to treat or prevent the onset of Autosomal Dominant Neovascular Inflammatory Vitreoretinopathy (ADNIV) and its sequelae by administering to a mammal in need of such therapy, an effective amount of these therapeutic agents that inhibit CAPN5.

The present invention provides in certain embodiments a CAPN5 substrate comprising an amino acid sequence of 10-30 amino acids in length having at least 80% sequence identity to a peptide, wherein the peptide is PDGFB (SEQ ID NO:18), IRX3 (SEQ ID NO:19), CAPN5-370-390 (SEQ ID NO:20), CAPN5-390-410 (SEQ ID NO:21), CAPN5-370-380 (SEQ ID NO:23) or CAPN14 (SEQ ID NO: 32).

The present invention provides in certain embodiments a CAPN5 substrate having at least 90% sequence identity to a peptide, wherein the peptide is PDGFB (SEQ ID NO:18), IRX3 (SEQ ID NO:19), CAPN5-370-390 (SEQ ID NO:20), CAPN5-390-410 (SEQ ID NO:21), CAPN5-370-380 (SEQ ID NO:23) or CAPN14 (SEQ ID NO: 32).

The present invention provides in certain embodiments a CAPN5 substrate having at least 95% sequence identity to a peptide, wherein the peptide is PDGFB (SEQ ID NO:18), IRX3 (SEQ ID NO:19), CAPN5-370-390 (SEQ ID NO:20), CAPN5-390-410 (SEQ ID NO:21), CAPN5-370-380 (SEQ ID NO:23) or CAPN14 (SEQ ID NO: 32).

In certain embodiments the peptide is CAPN5-370-380 (SEQ ID NO:23).

The present invention provides in certain embodiments a CAPN5 substrate or CAPN5 inhibitor as described above, wherein the peptide contains an unnatural (also called an "artificial") amino acid residue.

In certain embodiments, the unnatural amino acid residue renders the peptide bond uncleavable by calpain.

In certain embodiments, the modified amino acid residue is methylated.

In certain embodiments, the methylated amino acid residue is methyl-arginine, methyl-glycine, or methyl-isoleucine.

In certain embodiments, the unnatural amino acid residue is a D-amino acid.

In certain embodiments, the D-amino acid is D-glutamine or D-asparagine.

In certain embodiments, the unnatural amino acid residue is Acm-cysteine.

The present invention provides in certain embodiments a CAPN5 substrate or CAPN5 inhibitor as described above, wherein the peptide forms an alpha-helix. In certain embodiments, the peptide forms a circular peptide.

In certain embodiments, the peptide is from 5 to 11 amino acids in length.

In certain embodiments, the inhibitory peptide occupies the catalytic groove or region that prevents formation of the catalytic triad.

In certain embodiments, the inhibitory peptide is soluble in aqueous solutions.

In certain embodiments, the present invention provides a CAPN5 substrate that is Pep-1-Mod (SEQ ID NO:33), Pep-2-Mod (SEQ ID NO:34), Pep-3-Mod (SEQ ID NO:35), Pep-4-Mod (SEQ ID NO:36), Pep-5-Mod (SEQ ID NO:37) or Pep-6-Mod (SEQ ID NO:38).

In certain embodiments, the CAPN5 substrate is Pep-6-Mod (SEQ ID NO:38).

The present invention provides in certain embodiments a composition comprising the CAPN5 substrate or CAPN5 inhibitor as described above and a physiologically acceptable carrier.

The present invention provides in certain embodiments a method of identifying an inhibitor of CAPN5 comprising, contacting CAPN5 with a CAPN5 substrate described above in the presence of a target inhibitor, and measuring an activity level of the CAPN5 in the presence of the target inhibitor as compared to an activity level of CAPN5 in the absence of the target inhibitor. In certain embodiments, the present invention provides CAPN5 inhibitor identified by this method.

The present invention provides in certain embodiments a method of treating CAPN5-related inflammation by administering a therapeutic agent comprising the CAPN5 substrate or CAPN5 inhibitor as described above.

The present invention provides in certain embodiments a method of treating uveitis by administering a therapeutic agent comprising the CAPN5 substrate or CAPN5 inhibitor as described above.

The present invention provides in certain embodiments a therapeutic method for preventing or treating a pathological condition or symptom in a mammal, such as a human, wherein an anti-inflammatory activity is desired, comprising administering to a mammal in need of such therapy, an effective amount of a therapeutic agent comprising the CAPN5 substrate or CAPN5 inhibitor as described above.

The present invention provides in certain embodiments a therapeutic method for preventing or treating intraocular inflammation in a mammal, such as a human, comprising administering to a mammal in need of such therapy, an effective amount of a therapeutic agent comprising the CAPN5 substrate or CAPN5 inhibitor as described above.

The present invention provides in certain embodiments a method to treat intraocular inflammation comprising administering a therapeutically effective amount of a therapeutic agent comprising the CAPN5 substrate or CAPN5 inhibitor as described above to a mammal.

The present invention provides in certain embodiments a CAPN5 substrate or CAPN5 inhibitor as described above for use in medical therapy.

The present invention provides in certain embodiments the use of a CAPN5 substrate or CAPN5 inhibitor as described above for the manufacture of a medicament useful for the treatment of intraocular inflammation in a mammal.

The present invention provides in certain embodiments a solution comprising a carrier and a CAPN5 substrate or CAPN5 inhibitor as described above dispersed in the carrier.

The present invention provides in certain embodiments an isolated or purified nucleic acid that is less than 150 nucleotides in length encoding a peptide as described above.

In certain embodiments, the isolated or purified nucleic acid is less than 120 nucleotides in length.

The present invention provides in certain embodiments an expression cassette comprising the nucleic acid described above. In certain embodiments, the expression cassette, further comprises a promoter.

The present invention provides in certain embodiments a vector comprising the expression cassette described above.

The present invention provides in certain embodiments a cell comprising the expression cassette or the vector described above.

In certain embodiments, the present invention provides the CAPN5 substrate as described above, further comprising a detection agent to form a labelled CAPN5 substrate.

In certain embodiments, the detection agent is a fluorescent or colorimetric chemical agent.

In certain embodiments, the present invention provides a method of detecting CAPN5 comprising administering a labelled CAPN5 substrate_described above.

The terms "protein," "peptide" and "polypeptide" are used interchangeably herein. Peptide sequences specifically recited herein are written with the amino terminus on the left and the carboxy terminus on the right.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

BRIEF DESCRIPTION OF THE DRAWINGS

FIG. 1A. Calcium-activated CAPN5 autoproteolysis releases a 60 kDa and 45 kDa fragment. FIG. 1B. SBP-tagged CAPN5-PC (WT, and R243L) incubated with 1 mM calcium produced 60 kDa fragments. R243L CAPN5 produced the 60 kDa fragment at earlier time points than WT.

FIGS. 5A-5B. The CAPN5-370-80 peptide comprises a sequence motif that is conserved among calpains. (FIG. 5A) Multiple sequence alignment of the CAPN5-370-80 peptide with homologous sequences from other human calpains reveals highly related sequences that are specific to their corresponding calpains. There is high sequence conservation in the p.G376-377 positions, highlighting the functional importance of these residues in calpain structure and function. FIG. 5A discloses SEQ ID NOS 24-34, respectively, in order of appearance. (FIG. 5B) A homology model of domain III from human CAPN5 was generated using CAPN2 (PDB: 1KFU) as a template in MODELLER. Further conservation analysis was performed using the ConSurf server and was visualized on the domain III model in PyMOL. Results of this analysis identified p.G376-377 to be 100% conserved across 88 homologous calpain sequences. Structural modeling placed these residues on an exposed flexible loop, which would serve as an accessible site for calpain autoproteolysis.

FIG. 7A. EPLFAERK (SEQ ID NO: 22), FIG. 7B. CAPN5(p370-380)

FIG. 10 discloses "EPLFAERK" as SEQ ID NO: 22.

FIG. 12A: Substrate CAPN5p.372-378. FIG.

12B: Substrate CAPN5p.370-380. FIG. 12C. Substrate CAPN5p.370-390. FIG. 12A &C: The data from these peptides were fit using the Michaelis-Menten equation: Y=Vmax*X/(Km+X) B. The data from this peptide was fit using the substrate inhibition equation: Y=Vmax*X/(Km+X*(1+X/Ki)) FIG. 12D: Kinetics data from the Michaelis-Menten and substrate inhibition equations are shown in the table.

FIGS. 13A-13C. Tested peptides show calpain-specificity. Peptides were incubated in calpain activity buffer. FIG. 13A: The fluorescence measured for our lead peptide, CAPN5p370-380, was plotted and lines were fit using the following substrate inhibition equation, Y=Vmax*X/(Km+X*(1+X/Ki)). The peptide shows high proteolysis when incubated with CAPN5-WT and very limited proteolysis when incubated with CPAN1-WT (green). FIG. 13A discloses SEQ ID NO: 22. FIG. 13B: The fluorescence measure for a previously published calpain-1 peptide, EPLFAERK (SEQ ID NO: 22), was plotted and lines were fit using the following Michaelis-Menten equation, Y=Vmax*X/(Km+X). The peptide shows high proteolysis when incubated with CAPN1-WT (green) and very limited proteolysis when incubated with CAPN5-WT (blue), suggesting substrate specificity. FIG. 13C: Kinetics data from the Michaelis-Menten and substrate inhibition equations are shown in a table. FIG. 13C discloses SEQ ID NO: 22.

FIGS. 14A-14D: CAPN5 specifically targets a peptide corresponding to its own autocatalytic site and not homologous regions in other calpains. FIG. 14A: An alignment of the peptides shows very limited sequence homology. FIG. 14A discloses SEQ ID NOS 23 and 35-43, respectively, in order of appearance. FIG. 14B: CAPN5 did not proteolyze homologous regions of other CAPN members as well as it proteolyzed its own site, although there was some proteolysis of the CAPN14 peptide. The data points were plotted and fit using the Michaelis-Menten equation (not shown) and the substrate inhibition equation (shown). FIG. 14C: Peptides tested in (FIG. 14B) were incubated with CAPN1. CAPN1 does not appear to proteolyze these regions. The data points were plotted and fit using the Michaelis-Menten equation. FIG. 14D: Kinetics data from the Michaelis-Menten and substrate inhibitions equations are shown in a table.

FIG. 15A: Various concentrations of SNJ-1945 were incubated in a reaction with 50 µM EPLFAERK (SEQ ID NO: 22) (a CAPN1 substrate) and CAPN1 WT in activity. Data is plotted for CAPN1 as initial velocity (µM/sec) versus SNJ-1945 concentration. Addition of 1 µM SNJ-1945 slows the initial reaction rate by 100%. FIG. 15B: CAPN1 WT was incubated with and without SNJ-1945 at increasing concentrations of EPLFAERK substrate (SEQ ID NO: 22). Data is plotted for CAPN1 as initial velocity (µM/sec) versus substrate concentration. FIG. 15C: Various concentrations of SNJ-1945 were incubated in a reaction with CAPN5p.370-80 and CAPN5 WT in an activity buffer. Data is plotted for CAPN5 as initial velocity (µM/sec) versus SNJ-1945 concentration. Only after addition of 100 µM SNJ-1945 did the initial reaction rate slow to 100%. FIG. 15D: CAPN5 WT was incubated with and without SNJ-1945 at increasing concentrations of CAPN5 p.370-80 substrate. Data is plotted for CAPN5 as initial velocity (µM/sec) versus substrate concentration. Increasing substrate concentration for CAPN5 overcomes the inhibition by SNJ-1945.

FIGS. 16A-16B. Second generation inhibitors based off lead compound competitively inhibit CAPN5. First generation lead compound CAPN5 p.370-80 was modified using amide cyclization to generate a second generation competitive cyclic inhibitor. (FIG. 16A) Various concentrations of Cyclic CAPN5 p.370-80 were incubated in a reaction with CAPN5p.370-80 and CAPN5 WT in an activity buffer. Data is plotted for CAPN5 as initial velocity (µM/sec) versus Cyclic CAPN5 p.370-80 concentration. Addition of 10 µM Cyclic CAPN5 p.370-80 slows the initial reaction rate by 40%. (FIG. 16B) CAPN5 WT was incubated with and without 10 µM Cyclic CAPN5 p.370-80 at increasing concentrations of CAPN5 p.370-80 substrate. Data is plotted for CAPN5 as initial velocity (µM/sec) versus substrate concentration. Increasing concentrations of substrate does not overcome inhibition by cyclic peptide.

FIG. 18A. Structural model of the CAPN5 protease core with the peptide docked to it using AutoDock VINA. FIG. 18B. Scanning modifications were made to the amino acids of the lead compound to make the bonds un-cleavable by CAPN5. Despite modifications, the peptide still fit in the catalytic groove using docking predictions. FIG. 18C. N-terminal (EDANS) and C-terminal GLU-(DABCYL) FRET tags were added to the peptides for our standard CAPN5 assay and were dissolved in 70% DMSO. Peptides incubated for 15 minutes at various concentrations with 5 µg of MBP-CAPN5 WT. Data is plotted as initial velocity (uM/sec) versus peptide concentration fit to the Michaelis-Menten equation. Modification of the amino acids slows the reaction rate. FIG. 18D. Data is plotted as initial velocity (µM/sec) versus peptide concentration fit to the substrate inhibition equation.

FIGS. 19A-19G. Non-modified and modified peptides. FIG. 19A. Unmodified CAPN5-370-80 peptide (RQNRGGGCINH (SEQ ID NO: 23)). FIG. 19B. Pep-1-Mod containing methyl-Arginine and D-Glutamine. FIG. 19C. Pep-2-Mod containing D-Asparagine and methyl-Arginine. FIG. 19D. Pep-3-Mod containing N-Me Glycine and N-Me Glycine. FIG. 19E. Pep-4-Mod containing N-Me Glycine and Acm-Cysteine. FIG. 19F. Pep-5-Mod containing N-Me Isoleucine and D-Glutamine. FIG. 19G. Pep-6-Mod, which is a cyclization amide.

FIG. 20A. Structural model of the CAPN5 protease core with the peptide docked to it using AutoDock VINA. FIG. 20B. Chemical structure of the CAPN5-370-80 peptide (RQNRGGGCINH (SEQ ID NO: 23)). Scanning modifications were made to the amino acids of the peptide to make the bonds un-cleavable by CAPN5. The location of the modifications are denoted with circles N-terminal (EDANS) and C-terminal GLU-(DABCYL) FRET tags were added to the peptides for the standard CAPN5 assay and were dissolved in 70% DMSO. FIG. 20C. Peptides incubated for 15 minutes at various concentrations with 5 µg of MBP-CAPN5 WT in a buffer containing 20 mM Tris, 300 mM NaCl, 2 mM DTT, pH 7.5 to measure activity. Data is plotted as initial velocity (µM/sec) versus peptide concentration. Modification of the amino acids slows the reaction rate. FIG. 20C discloses SEQ ID NOS 23 and 44-45, respectively, in order of appearance. FIG. 20D. Close-up of graph region highlighting the differences in proteolytic activity at 5 µM substrate. FIG. 20D discloses SEQ ID NOS 23 and 44-45, respectively, in order of appearance.

DETAILED DESCRIPTION

Figure 1A:
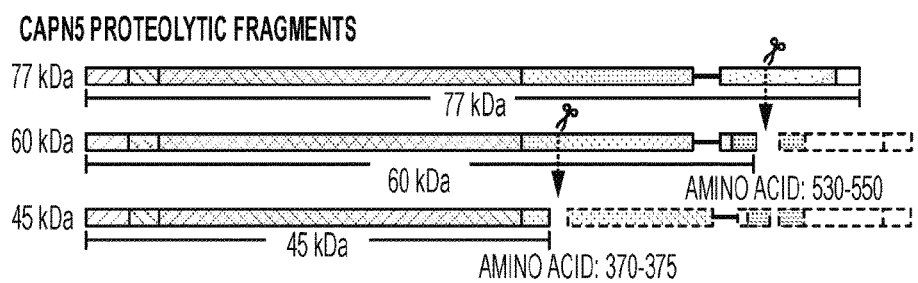
FIGS. 1A-1B. CAPN5 has two autoproteolysis sites.

CAPN5 inhibition is one strategy for therapeutically inhibiting retinal damage. The studies described herein demonstrate novel molecules and assays used to inhibit CAPN5 activity. To demonstrate CAPN5 inhibition, a CAPN5 in vitro proteolysis assay and a specific substrate was needed. Potential substrates were identified from a recent CAPN5 proteolysis screen of the retinal proteome. These CAPN5 proteolytic targets were verified in vitro, and narrowed down the exact site of cleavage, until it was possible to identify short polypeptides that are CAPN5 substrates. This approach was used on several targets, including CAPN5 itself. These substrates are modified to design a CAPN5-specific inhibitor.

Peptides of the Present Invention

The present invention provides in certain embodiments a CAPN5 substrate comprising an amino acid sequence of 10-30 amino acids in length having at least 80% sequence identity to a peptide, wherein the peptide is PDGFB (SEQ ID NO:18), IRX3 (SEQ ID NO:19), CAPN5-370-390 (SEQ ID NO:20), CAPN5-390-410 (SEQ ID NO:21) or CAPN5-370-390 (SEQ ID NO:23). In certain embodiments, the peptide has at least 81%, 82%, 83%, 84%, 85%, 86%, 87%, 88%, 89%, 90%, 91%, 92%, 93%, 94%, 95%, 96%, 97%, 98%, 99% or 100% sequence identity to a peptide, wherein the peptide is PDGFB (SEQ ID NO:18), IRX3 (SEQ ID NO:19), CAPN5-370-390 (SEQ ID NO:20), CAPN5-390-410 (SEQ ID NO:21) or CAPN5-370-390 (SEQ ID NO:23). In certain embodiments the peptide is CAPN5-370-390 (SEQ ID NO:23).

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes peptides with reduced peptide bonds, which will prevent proteolytic degradation of the peptide. Also, the term includes the amino acid analog α-amino-isobutyric acid. The term also includes natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

In certain embodiments, the peptides are modified by C-terminal amidation, head to tail cyclic peptides, or containing Cys residues for disulfide cyclization, siderophore modification, or N-terminal acetylation.

The term "peptide" describes a sequence of 7 to 50 amino acids or peptidyl residues. Preferably a peptide comprises 7 to 25, or 7 to 15 or 7 to 13 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

As used herein, the term "enzyme" includes variants or biologically active or inactive fragments of a polypeptides.

A "variant" of one of the polypeptides is a polypeptide that is not completely identical to a native protein. Such variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Aline is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The amino acid changes are achieved by changing the codons of the corresponding nucleic acid sequence. It is known that such polypeptides can be obtained based on substituting certain amino acids for other amino acids in the polypeptide structure in order to modify or improve biological activity. For example, through substitution of alternative amino acids, small conformational changes may be conferred upon a polypeptide that results in increased activity. Alternatively, amino acid substitutions in certain polypeptides may be used to provide residues, which may then be linked to other molecules to provide peptide-molecule conjugates which retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated is intended for use in immunological embodiments. The greatest local average hydrophilicity of a "protein", as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant protein has at least 50%, at least about 80%, or even at least about 90% but less than 100%, contiguous amino acid sequence homology or identity to the amino acid sequence of a corresponding native protein.

The amino acid sequence of the variant polypeptide corresponds essentially to the native polypeptide's amino acid sequence. As used herein "correspond essentially to" refers to a polypeptide sequence that will elicit a biological response substantially the same as the response generated by the native protein. Such a response may be at least 60% of the level generated by the native protein, and may even be at least 80% of the level generated by native protein.

A variant may include amino acid residues not present in the corresponding native protein or deletions relative to the corresponding native protein. A variant may also be a truncated "fragment" as compared to the corresponding native protein, i.e., only a portion of a full-length protein. Protein variants also include peptides having at least one D-amino acid.

The variant protein may be expressed from an isolated DNA sequence encoding the variant protein. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence. The terms "protein," "peptide" and "polypeptide" are used interchangeably herein.

In certain embodiments, the peptide forms an alpha-helix.
In certain embodiments, the inhibitor is a circular peptide.

Screening Methods

The present disclosure provides methods to screen for and identify amino acid sequences that target, e.g., specifically target CAPN5. The present invention provides in certain embodiments a method of identifying an inhibitor of CAPN5 comprising, contacting CAPN5 with a CAPN5 substrate in the presence of a target inhibitor, and measuring an activity level of CAPN5 substrate as described above in the presence of the target inhibitor as compared to an activity level of CAPN5 in the absence of the target inhibitor.

Compositions and Methods of Use

The present invention provides in certain embodiments a composition comprising the CAPN5 substrate or CAPN5 inhibitor as described above and a physiologically acceptable carrier.

The present invention provides in certain embodiments a therapeutic method for preventing or treating a pathological condition or symptom in a mammal, such as a human, wherein an anti-inflammatory activity is desired, comprising administering to a mammal in need of such therapy, an effective amount of a therapeutic agent comprising the CAPN5 substrate or CAPN5 inhibitor as described above.

The present invention provides in certain embodiments a therapeutic method for preventing or treating intraocular inflammation in a mammal, such as a human, comprising administering to a mammal in need of such therapy, an effective amount of a therapeutic agent comprising the CAPN5 substrate or CAPN5 inhibitor as described above.

The present invention provides in certain embodiments a method to treat intraocular inflammation comprising administering a therapeutically effective amount of a therapeutic agent comprising the CAPN5 substrate or CAPN5 inhibitor as described above to a mammal.

The present invention provides in certain embodiments a CAPN5 substrate or CAPN5 inhibitor as described above for use in medical therapy.

The present invention provides in certain embodiments the use of a CAPN5 substrate or CAPN5 inhibitor as described above for the manufacture of a medicament useful for the treatment of intraocular inflammation in a mammal.

The present invention provides in certain embodiments a solution comprising a carrier and a CAPN5 substrate or CAPN5 inhibitor as described above dispersed in the carrier.

Nucleic Acids of the Present Invention

The present invention provides in certain embodiments an isolated or purified nucleic acid that is less than 50 nucleotides in length encoding a peptide as described above.

In certain embodiments, the isolated or purified nucleic acid is less than 20 nucleotides in length. In certain embodiments, the peptide is 10, 11, 12, 13, 14, 15, 16, 17, 18, 19, 20, 21, 22, 23, 24, 25, 26, 27, 28, 29, or 30 nucleotides in length.

The present invention provides in certain embodiments an expression cassette comprising the nucleic acid described above. In certain embodiments, the expression cassette, further comprises a promoter.

The present invention provides in certain embodiments a vector comprising the expression cassette described above.

The present invention provides in certain embodiments a cell comprising the expression cassette or the vector described above.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell or bacteriophage. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "chimeric" refers to any gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The terms "protein," "peptide" and "polypeptide" are used interchangeably herein.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis which encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, NY: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the anti sense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a known mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wisconsin, USA). Alignments using these programs can be performed using the default parameters.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world-wide-web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. Generally, highly stringent hybridization and wash conditions are selected to be about 5EC lower than the $T_m$ for the specific sequence at a defined ionic strength and pH.

An example of highly stringent wash conditions is 0.15 M NaCl at 72EC for about 15 minutes. An example of stringent wash conditions is a 0.2×SSC wash at 65EC for 15 minutes. Often, a high stringency wash is preceded by a low stringency wash to remove background probe signal. An example medium stringency wash for a duplex of, e.g., more than 100 nucleotides, is 1×SSC at 45EC for 15 minutes. An example low stringency wash for a duplex of, e.g., more than 100 nucleotides, is 4-6×SSC at 40EC for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30EC and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of therapeutic agents may be accomplished through the administration of the therapeutic agent, such as a peptide. Pharmaceutical formulations, dosages and routes of administration for peptide are generally known.

The present invention envisions treating uveitis in a mammal by the administration of an agent, e.g., a peptide. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly administered to the eye. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intraocular routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 saline solutions and water.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

The invention will now be illustrated by the following non-limiting Examples.

Example 1

Figure 1B:
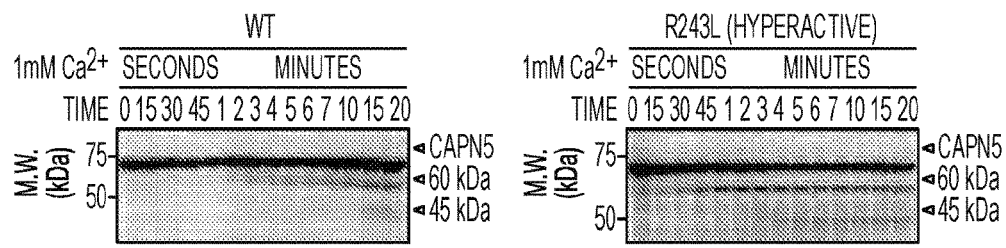

Mutant CAPN5 undergoes increased autoproteolysis. Autoproteolysis was used as a starting point for finding a CAPN5-specific substrate. CAPN5 cleaves itself at two sites, releasing a 60 kDa or 45 kDa enzyme (FIGS. 1A-B). A time course of CAPN5 autoproteolysis showed that the R243L mutant had a faster rate of autoproteolysis than WT CAPN5 (FIG. 1B). The sequence comprising this site was used to home in on a peptide substrate.

Identification of optimal CAPN5 cleavage peptides. Possible substrate sequences were narrowed down to 10-20 amino acids (data not shown). CAPN5 autoproteolysis cleavages sites were narrowed down to two peptides, which we term CAPN5-370-390 and CAPN5-390-410 (Table 1). FRET peptides were designed based on determined cleavage sites (Biopeptek; Table 1).

TABLE 1

Putative CAPN5 Cleavage Site Peptides

| Target Protein | Amino Acids | Sequence | SEQ ID NO |
|---|---|---|---|
| PDGFB | 155-170 | KIEIVRKKPIFKKATV | SEQ ID NO: 18 |
| IRX3 | 441-451 | AAGHPAAAAAF | SEQ ID NO: 19 |
| CAPN5-370-390 | 370-390 | RQNRGGGCINHKDTFFQNPQY | SEQ ID NO: 20 |
| CAPN5-390-410 | 390-410 | YIFEVKKPEDEVLICIQQRPK | SEQ ID NO: 21 |
| Negative control | — | EPLFAERK, (AC)-LLY-(AFC) | SEQ ID NO: 22 |

Figure 2:
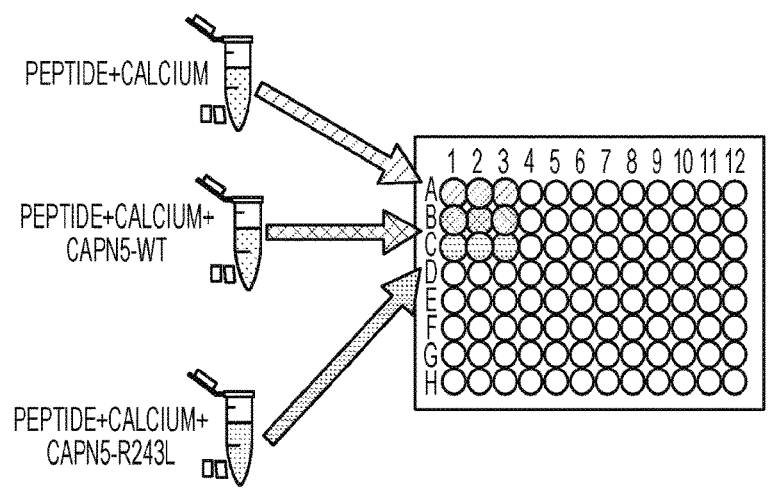
FIG. 2. Diagram of Assay. 10 uM of FRET substrates were added to a solution containing 2 mM DTT, 5 uM Calcium, and CAPN5 Buffer (20 mM Tris, 300 mM NaCl, pH 7.5) to a volume of 100 uL. The solution was pipetted into a 96 well plate in wells that contained 24 uM of CAPN5-WT, CAPN5-R243L, or no CAPN5. The fluorescence of each well was measured using a Tecan Infinite M200 Pro plate reader.
Figure 3:
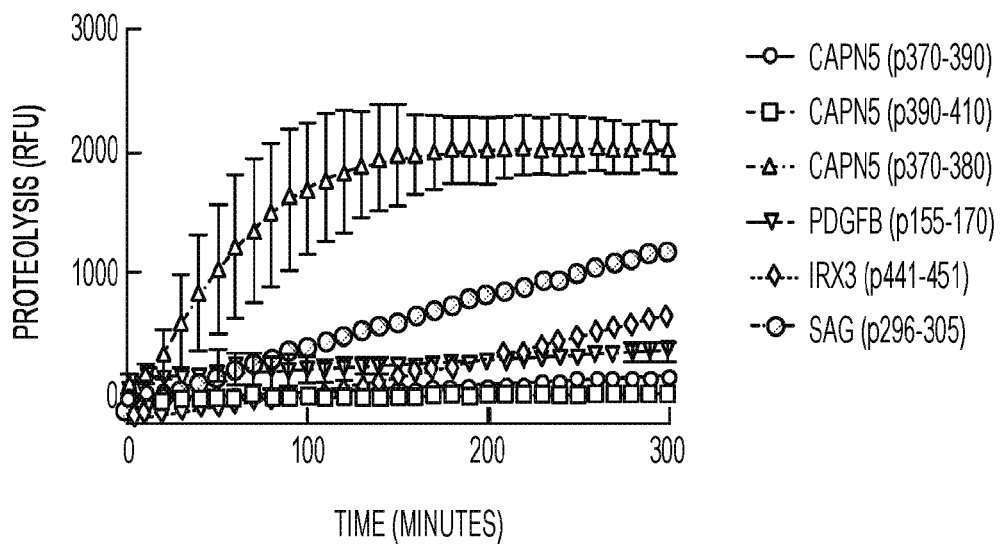
FIG. 3. CAPN5-WT proteolyzes the substrate, CAPN5 (p370-380), at a higher rate than other peptides. When CAPN5-WT is added to a variety of substrates, the greatest fluorescent intensity is detected with substrate CAPN5 (p370-380).
Figure 4:
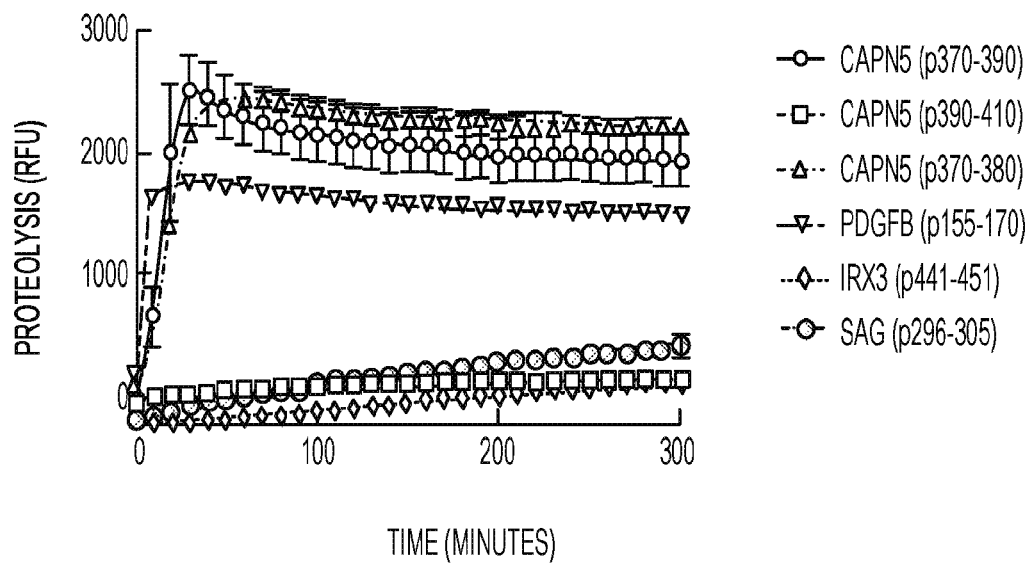
FIG. 4. CAPN5-R243L proteolyzes three substrates at a higher rate than other peptides. When CAPN5-R243L is added to a variety of substrates, the greatest fluorescent intensity is detected with substrates CAPN5 (p370-390), CAPN5 (370-380), and PDGFB (155-170).

An assay to determine efficiency of CAPN5 peptide targets is demonstrated in FIG. 2. Peptide substrates dissolved in DMSO and H$_2$O were incubated with WT CAPN5 at 37° C. in the presence or absence of calcium until a change in fluorescence was no longer detected. Interestingly, the CAPN5-370-380 fragment was the most sensitive to cleavage by both WT and R243L CAPN5 (FIGS. 3 and 4). As expected, R243LCAPN5 (hyperactive) cleaved substrate fragments at a higher rate (FIG. 4). Inhibitor peptides were identified that serve as the lead compounds for optimization. FIGS. 3 and 4 show that CAPN5 amino acids 370-380 represent a putative new therapeutic compound for CAPN5 inhibition.

The CAPN5-370-80 peptide comprises a sequence motif that is conserved among calpains (FIGS. 5A and 5B).

A previously-identified CAPN1 peptide, EPLFAERK (SEQ ID NO: 22), is specific to CAPN1 as it is not proteolyzed by CAPN5. Alternatively, a peptide derived from a suspected CAPN5 autoproteolysis site, CAPN5 (370-380, RQNRGGGCINH (SEQ ID NO:23)), is specific to CAPN5 and is not proteolyzed by CAPN1.

Example 2

Figure 6:
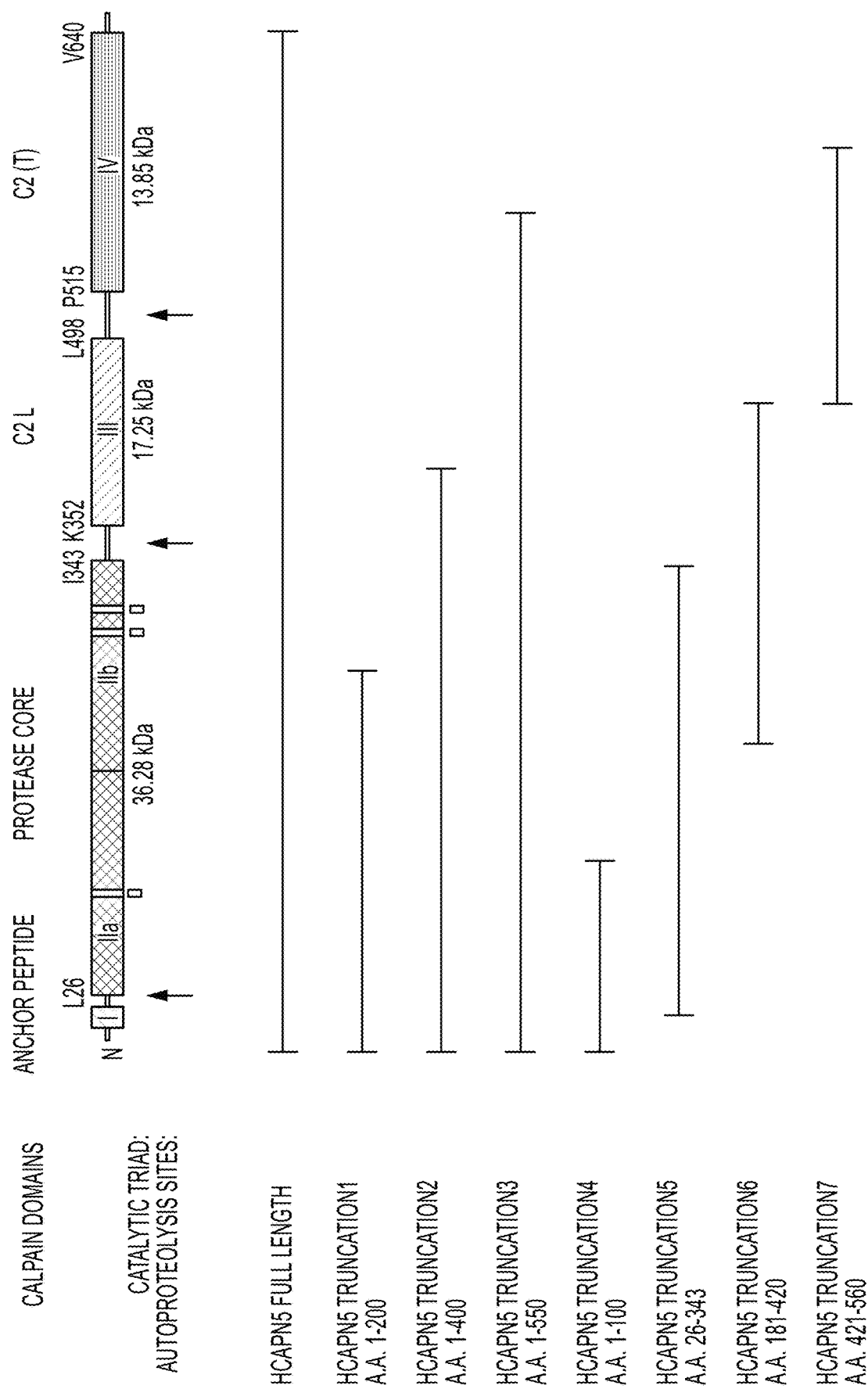
FIG. 6. Schematic of Calpain Domains and various truncations of *Homo sapiens* calpain 5 (CAPN5).
Figure 7A:
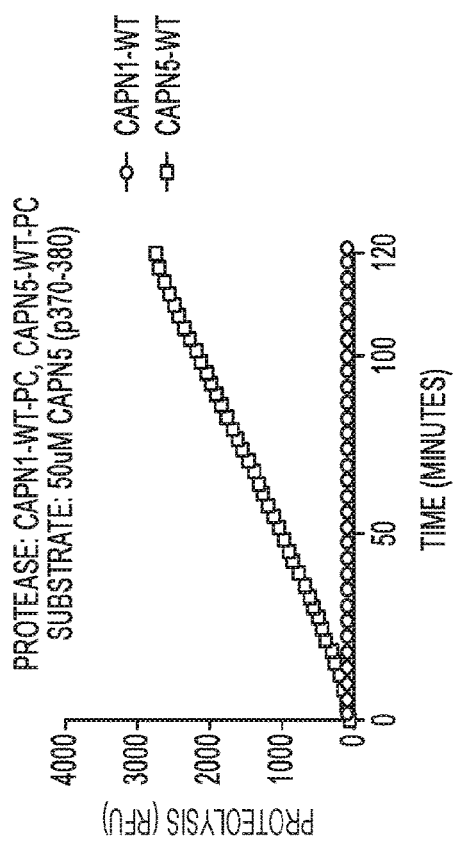
FIGS. 7A-7B. Graphs showing CAPN1 vs. CAPN5 cleavage.
Figure 7B:
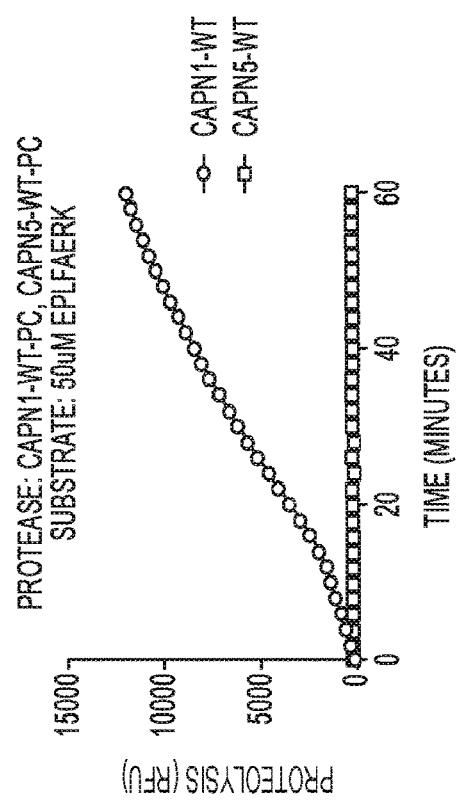
Figure 8:
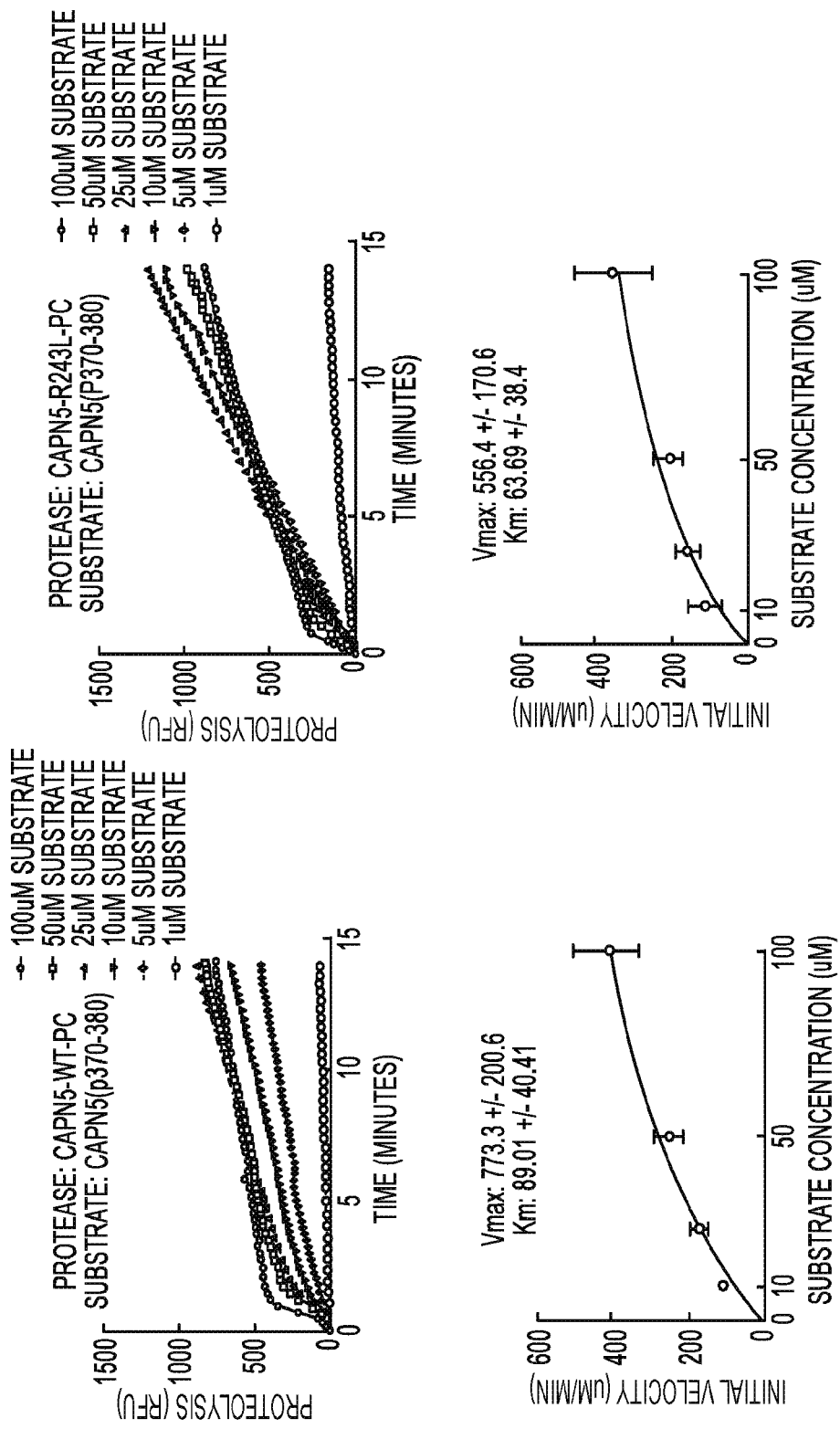
FIG. 8. Kinetics of initial slope for CAPN5-WT and CAPN5-R243L.
Figure 9:
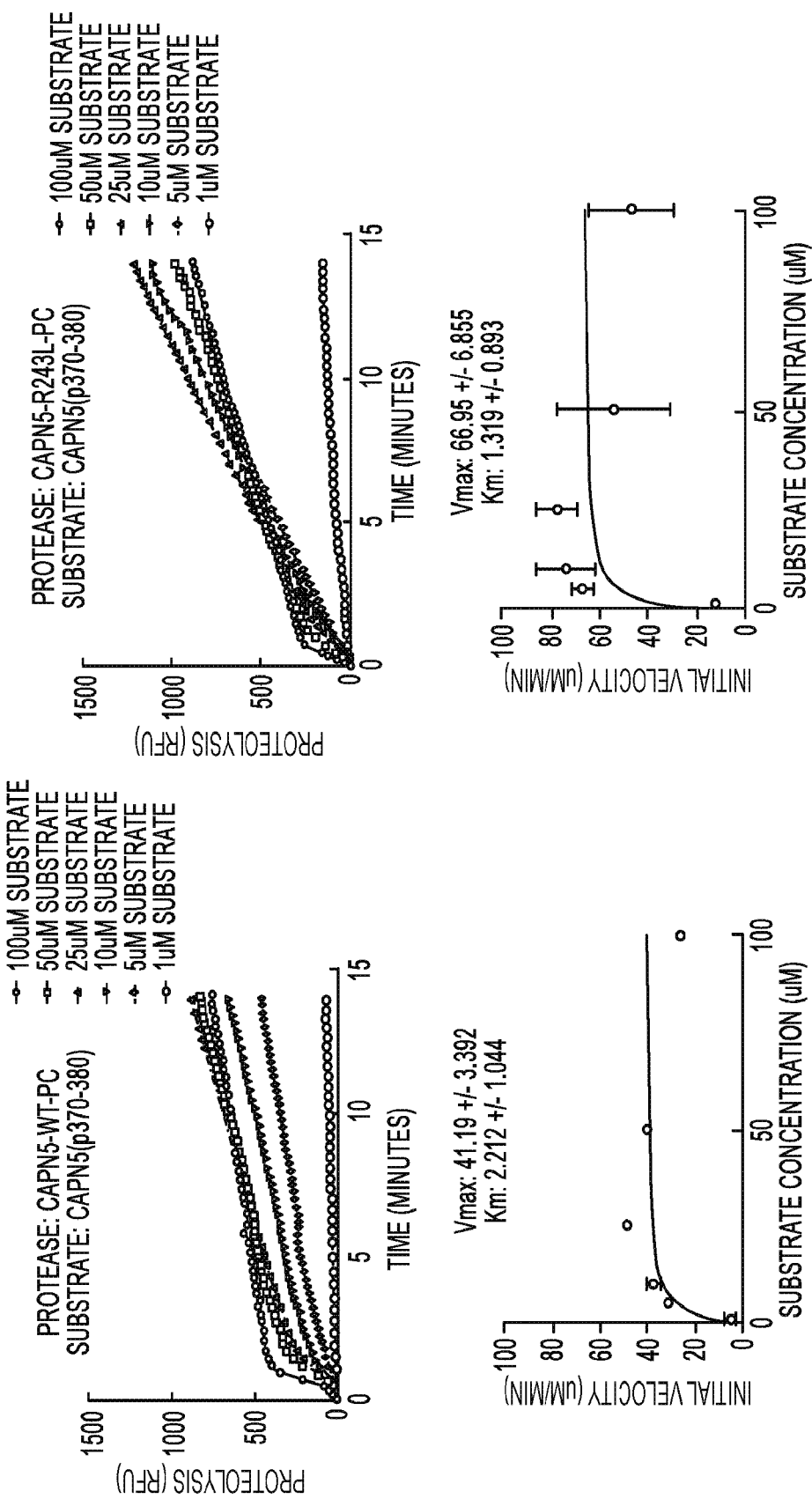
FIG. 9. Kinetics of steady slope for CAPN5-WT and CAPN5-R243L.
Figure 10:
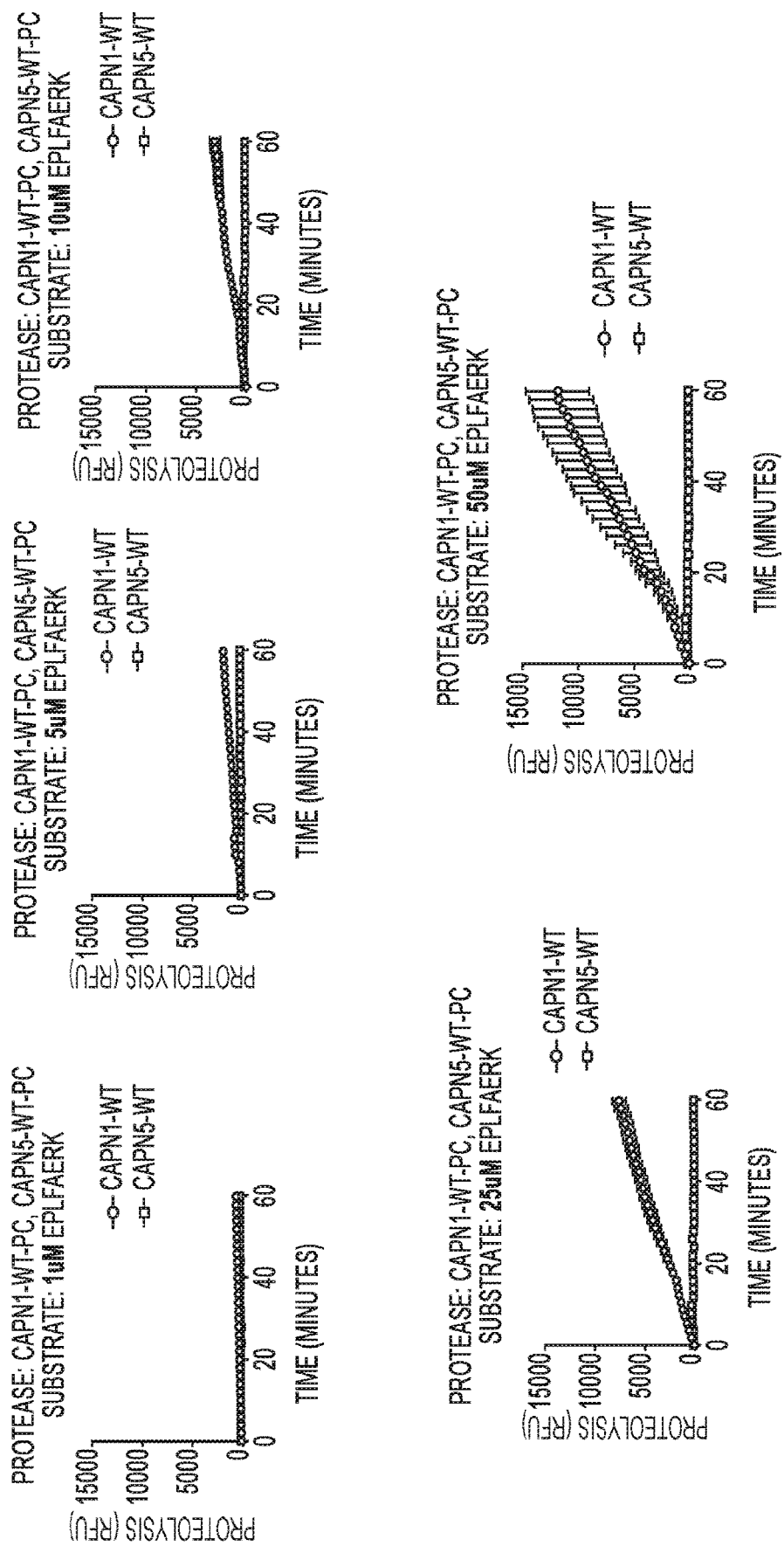
FIG. 10. Peptides are specific to CAPN1 or CAPN5.
Figure 11:
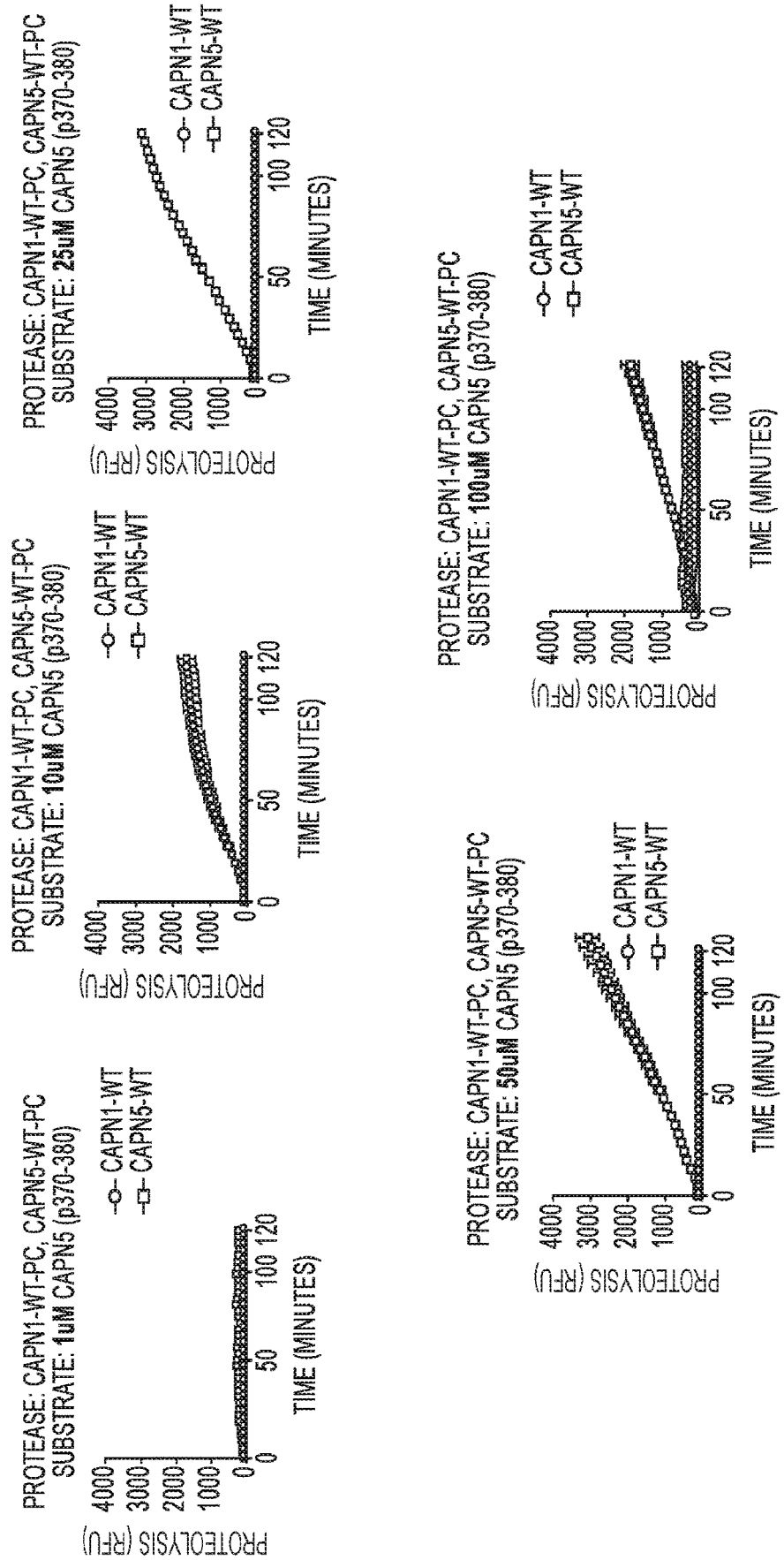
FIG. 11. Peptides are specific to CAPN1 or CAPN5.

Various truncations of *Homo sapiens* calpain 5 (CAPN5) were generated, as shown in FIG. 6. Nucleic acid and protein sequences for *Homo sapiens* calpain 5 (CAPN5) and various truncations are provided below:
Homo sapiens calpain 5 (CAPN5), mRNA
NCBI Reference Sequence: NM_004055.4
GenBank Graphics
>gi|87044927:186-2108 *Homo sapiens* calpain 5 (CAPN5), mRNA DNA Sequence:

(SEQ ID NO: 1)
ATGTTCTCGTGTGTGAAGCCCTATGAGGAACCAGACTACTCAGCCCTGAG

GCGGGACTGCCGGCGCAGGAAGGTGCTCTTCGAGGACCCCCTCTTCCCCG

CCACTGACGACTCACTCTACTATAAGGGCACGCCGGGGCCCGCCGTCAGG

TGGAAGCGACCCAAGGGCATCTGCGAGGACCCCCGCCTCTTTGTGGATGG

CATCAGCTCCCACGACCTGCACCAGGGCCAGGTGGGCAACTGCTGGTTTG

TGGCAGCCTGCTCGTCACTTGCCTCCCGGGAGTCGCTGTGGCAAAAGGTC

-continued

ATCCCAGACTGGAAGGAGCAGGAATGGGACCCCGAAAAGCCCAACGCCTA

CGCGGGCATCTTCCACTTCCACTTCTGGCGCTTCGGGGAATGGGTGGACG

TGGTCATCGATGACCGGCTGCCCACAGTCAACAACCAGCTCATCTACTGC

CACTCCAACTCCCGCAATGAGTTTTGGTGCGCCCTAGTGGAGAAGGCCTA

TGCCAAACTGGCAGGCTGTTACCAGGCCCTGGATGGAGGCAACACAGCAG

ACGCACTGGTGGACTTCACGGGTGGTGTTTCTGAGCCCATCGACCTGACC

GAGGGTGACTTTGCCAACGATGAGACTAAGAGGAACCAGCTCTTTGAGCG

CATGTTAAAGGTGCACAGCCGGGGCGGCCTCATCAGTGCCTCCATCAAGG

CAGTGACAGCAGCTGACATGGAGGCCCGCCTGGCGTGCGGCCTGGTAAAG

GGCCACGCATACGCCGTCACTGATGTGCGCAAGGTGCGCCTGGGCCACGG

CCTACTGGCCTTCTTCAAGTCAGAGAAGTTGGACATGATCCGCCTGCGCA

ACCCCTGGGGCGAGCGGGAGTGGAACGGGCCCTGGAGTGACACCTCGGAG

GAGTGGCAGAAAGTGAGCAAGAGTGAGCGGGAGAAGATGGGTGTGACCGT

GCAGGACGACGGTGAGTTCTGGATGACCTTCGAGGACGTGTGCCGGTACT

TCACGGACATCATCAAGTGCCGCGTGATCAACACATCCCACCTGAGCATC

CACAAGACGTGGGAGGAGGCCCGGCTGCATGGCGCCTGGACGCTGCATGA

GGACCCGCGACAGAACCGCGGTGGCGGCTGCATCAACCACAAGGACACCT

TCTTCCAGAACCCACAGTACATCTTCGAAGTCAAGAAGCCAGAAGATGAA

GTCCTGATCTGCATCCAGCAGCGGCCAAAGCGGTCTACGCGCCGGGAGGG hcapn5-FL: capn5 full length+3×myc (indicated in bold), 2013 nucleotides, 671 amino acids
DNA Sequence:

(SEQ ID NO: 2)
ATGTTCTCGTGTGTGAAGCCCTATGAGGACCAGAACTACTCAGCCCTGAG
GCGGGACTGCCGGCGCAGGAAGGTGCTCTTCGAGGACCCCCTCTTCCCCG
CCACTGACGACTCACTCTACTATAAGGGCACGCCGGGGCCCGCCGTCAGG
TGGAAGCGACCCAAGGGCATCTGCGAGGACCCCCGCCTCTTTGTGGATGG
CATCAGCTCCCACGACCTGCACCAGGGCCAGGTGGGCAACTGCTGGTTTG
TGGCAGCCTGCTCGTCACTTGCCTCCCGGGAGTCGCTGTGGCAAAAGGTC
ATCCCAGACTGGAAGGAGCAGGAATGGGACCCCGAAAAGCCCAACGCCTA
CGCGGGCATCTTCCACTTCCACTTCTGGCGCTTCGGGGAATGGGTGGACG
TGGTCATCGATGACCGGCTGCCCACAGTCAACAACCAGCTCATCTACTGC
CACTCCAACTCCCGCAATGAGTTTTGGTGCGCCCTAGTGGAGAAGGCCTA
TGCCAAACTGGCAGGCTGTTACCAGGCCCTGGATGGAGGCAACACAGCAG
ACGCACTGGTGGACTTCACGGGTGGTGTTTCTGAGCCCATCGACCTGACC
GAGGGTGACTTTGCCAACGATGAGACTAAGAGGAACCAGCTCTTTGAGCG
CATGTTAAAGGTGCACAGCCGGGGCGGCCTCATCAGTGCCTCCATCAAGG
CAGTGACAGCAGCTGACATGGAGGCCCGCCTGGCGTGCGGCCTGGTAAAG
GGCCACGCATACGCCGTCACTGATGTGCGCAAGGTGCGCCTGGGCCACGG
CCTACTGGCCTTCTTCAAGTCAGAGAAGTTGGACATGATCCGCCTGCGCA
ACCCCTGGGGCGAGCGGGAGTGGAACGGGCCTGGAGTGACACCTCGGAG
GAGTGGCAGAAAGTGAGCAAGAGTGAGCGGGAGAAGATGGGTGTGACCGT
GCAGGACGACGGTGAGTTCTGGATGACCTTCGAGGACGTGTGCCGGTACT
TCACGGACATCATCAAGTGCCGCGTGATCAACACATCCCACCTGAGCATC
CACAAGACGTGGGAGGAGGCCCGGCTGCATGCGCCTGGACGCTGCATGA
GGACCCGCGACAGAACCGCGGTGGCGGCTGCATCAACCACAAGGACACCT

TCTTCCAGAACCCACAGTACATCTTCGAAGTCAAGAAGCCAGAAGATGAA
GTCCTGATCTGCATCCAGCAGCGGCCAAAGCGGTCTACGCGCCGGGAGGG
CAAGGGTGAGAACCTGGCCATTGGCTTTGACATCTACAAGGTGGAGGAGA
ACCGCCAGTACCGCATGCACAGCCTGCAGCACAAGGCCGCCAGCTCCATC
TACATCAACTCACGCAGCGTCTTCCTGCGCACCGACCAGCCCGAGGGCCG
CTATGTCATCATCCCCACAACCTTCGAGCCAGGCCACACTGGCGAGTTCC
TGCTCCGAGTCTTCACTGATGTGCCCTCCAACTGCCGGGAGCTGCGCCTG
GATGAGCCCCCACACACCTGCTGGAGCTCCCTCTGTGGCTACCCCCAGCT
GGTGACCCAGGTACATGTCCTGGGAGCTGCTGGCCTCAAGGACTCCCCAA
CAGGGGCTAACTCTTATGTGATCATCAAGTGTGAGGGAGACAAAGTCCGC
TCGGCTGTGCAGAAGGGCACCTCCACACCAGAGTACAATGTGAAAGGCAT
CTTCTACCGCAAGAAGCTGAGCCAGCCCATCACTGTACAGGTCTGGAACC
ACCGAGTGCTGAAGGATGAATTTCTGGGCCAGGTGCACCTAAAGGCTGAC
CCGGACAACCTCCAGGCCCTGCATACCCTCCACCTCCGGGACCGAAATAG
CCGGCAGCCCAGCAACCTGCCAGGCACTGTGGCCGTGCACATTCTCAGCA
GCACCTCCCTCATGGCTGTC**GAGCAGAAACTCATCTCAGAAGAGGATCTG
GAGCAGAAACTCATCTCAGAAGAGGATCTGGAGCAGAAACTCATCTCAGA
AGAGGATCTG**TGA

Protein Sequence:

(SEQ ID NO: 3)
MFSCVKPYED QNYSALRRDC RRRKVLFEDP LFPATDDSLY
YKGTPGPAVR WKRPKGICED PRLFVDGISS HDLHQGQVGN
CWFVAACSSL ASRESLWQKV IPDWKEQEWD PEKPNAYAGI
FHFHFWRFGE WVDVVIDDRL PTVNNQLIYC HSNSRNEFWC
ALVEKAYAKL AGCYQALDGG NTADALVDFT GGVSEPIDLT
EGDFANDETK RNQLFERMLK VHSRGGLISA SIKAVTAADM
EARLACGLVK GHAYAVTDVR KVRLGHGLLA FFKSEKLDMI
RLRNPWGERE WNGPWSDTSE EWQKVSKSER EKMGVTVQDD
GEFWMTFEDV CRYFTDIIKC RVINTSHLSI HKTWEEARLH
GAWTLHEDPR QNRGGGCINH KDTFFQNPQY IFEVKKPEDE
VLICIQQRPK RSTRREGKGE NLAIGFDIYK VEENRQYRMH
SLQHKAASSI YINSRSVFLR TDQPEGRYVI IPTTFEPGHT
GEFLLRVFTD VPSNCRELRL DEPPHTCWSS LCGYPQLVTQ
VHVLGAAGLK DSPTGANSYV IIKCEGDKVR SAVQKGTSTP
EYNVKGIFYR KKLSQPITVQ VWNHRVLKDE FLGQVHLKAD
PDNLQALHTL HLRDRNSRQP SNLPGTVAVH ILSSTSLMAV
EQKLISEEDL EQKLISEEDL EQKLISEEDL * hCAPN5-truncation1: 1-200 amino acids+3×myc (indicated in bold), 693 nucleotides, 231 amino acids DNA Sequence:

(SEQ ID NO: 4)
ATGTTCTCGTGTGTGAAGCCCTATGAGGACCAGAACTACTCAGCCCTGAG
GCGGGACTGCCGGCGCAGGAAGGTGCTCTTCGAGGACCCCCTCTTCCCCG
CCACTGACGACTCACTCTACTATAAGGGCACGCCGGGCCCGCCGTCAGG
TGGAAGCGACCCAAGGGCATCTGCGAGGACCCCCGCCTCTTTGTGGATGG
CATCAGCTCCCACGACCTGCACCAGGGCCAGGTGGGCAACTGCTGGTTTG
TGGCAGCCTGCTCGTCACTTGCCTCCCGGGAGTCGCTGTGGCAAAAGGTC
ATCCCAGACTGGAAGGAGCAGGAATGGGACCCCGAAAAGCCCAACGCCTA
CGCGGGCATCTTCCACTTCCACTTCTGGCGCTTCGGGGAATGGGTGGACG
TGGTCATCGATGACCGGCTGCCCACAGTCAACAACCAGCTCATCTACTGC
CACTCCAACTCCCGCAATGAGTTTTGGTGCGCCCTAGTGGAGAAGGCCTA
TGCCAAACTGGCAGGCTGTTACCAGGCCCTGGATGGAGGCAACACAGCAG
ACGCACTGGTGGACTTCACGGGTGGTGTTTCTGAGCCCATCGACCTGACC
GAGCAGAAACTCATCTCAGAAGAGGATCTGGAGCAGAAACTCATCTCAGA
AGAGGATCTGGAGCAGAAACTCATCTCAGAAGAGGATCTGTGA

Protein Sequence:

(SEQ ID NO: 5)
MFSCVKPYED QNYSALRRDC RRRKVLFEDP LFPATDDSLY
YKGTPGPAVR WKRPKGICED PRLFVDGISS HDLHQGQVGN
CWFVAACSSL ASRESLWQKV IPDWKEQEWD PEKPNAYAGI
FHFHFWRFGE WVDVVIDDRL PTVNNQLIYC HSNSRNEFWC
ALVEKAYAKL AGCYQALDGG NTADALVDFT GGVSEPIDLT
EQKLISEEDL EQKLISEEDL EQKLISEEDL * hCAPN5-truncation2: 1-400 amino acids+3×myc (indicated in bold), 1293 nts, 431 amino acids DNA Sequence:

(SEQ ID NO: 6)
ATGTTCTCGTGTGTGAAGCCCTATGAGGACCAGAACTACTCAGCCCTGAG
GCGGGACTGCCGGCGCAGGAAGGTGCTCTTCGAGGACCCCCTCTTCCCCG
CCACTGACGACTCACTCTACTATAAGGGCACGCCGGGCCCGCCGTCAGG
TGGAAGCGACCCAAGGGCATCTGCGAGGACCCCCGCCTCTTTGTGGATGG
CATCAGCTCCCACGACCTGCACCAGGGCCAGGTGGGCAACTGCTGGTTTG
TGGCAGCCTGCTCGTCACTTGCCTCCCGGGAGTCGCTGTGGCAAAAGGTC
ATCCCAGACTGGAAGGAGCAGGAATGGGACCCCGAAAAGCCCAACGCCTA
CGCGGGCATCTTCCACTTCCACTTCTGGCGCTTCGGGGAATGGGTGGACG
TGGTCATCGATGACCGGCTGCCCACAGTCAACAACCAGCTCATCTACTGC
CACTCCAACTCCCGCAATGAGTTTTGGTGCGCCCTAGTGGAGAAGGCCTA
TGCCAAACTGGCAGGCTGTTACCAGGCCCTGGATGGAGGCAACACAGCAG
ACGCACTGGTGGACTTCACGGGTGGTGTTTCTGAGCCCATCGACCTGACC
GAGGGTGACTTTGCCAACGATGAGACTAAGAGGAACCAGCTCTTTGAGCG
CATGTTAAAGGTGCACAGCCGGGGCGGCCTCATCAGTGCCTCCATCAAGG
CAGTGACAGCAGCTGACATGGAGGCCCGCCTGGCGTGCGGCCTGGTAAAG
GGCCACGCATACGCCGTCACTGATGTGCGCAAGGTGCGCCTGGGCCACGG
CCTACTGGCCTTCTTCAAGTCAGAGAAGTTGGACATGATCCGCCTGCGCA
ACCCCTGGGGCGAGCGGGAGTGGAACGGGCCCTGGAGTGACACCTCGGAG
GAGTGGCAGAAAGTGAGCAAGAGTGAGCGGGAGAAGATGGGTGTGACCGT
GCAGGACGACGGTGAGTTCTGGATGACCTTCGAGGACGTGTGCCGGTACT
TCACGGACATCATCAAGTGCCGCGTGATCAACACATCCCACCTGAGCATC
CACAAGACGTGGGAGGAGGCCCGGCTGCATGGCGCCTGGACGCTGCATGA
GGACCCGCGACAGAACCGCGGTGGCGGCTGCATCAACCACAAGGACACCT
TCTTCCAGAACCCACAGTACATCTTCGAAGTCAAGAAGCCAGAAGATGAA
GAGCAGAAACTCATCTCAGAAGAGGATCTGGAGCAGAAACTCATCTCAGA
AGAGGATCTGGAGCAGAAACTCATCTCAGAAGAGGATCTGTGA

Protein Sequence:

(SEQ ID NO: 7)
MFSCVKPYED QNYSALRRDC RRRKVLFEDP LFPATDDSLY
YKGTPGPAVR WKRPKGICED PRLFVDGISS HDLHQGQVGN
CWFVAACSSL ASRESLWQKV IPDWKEQEWD PEKPNAYAGI
FHFHFWRFGE WVDVVIDDRL PTVNNQLIYC HSNSRNEFWC
ALVEKAYAKL AGCYQALDGG NTADALVDFT GGVSEPIDLT
EGDFANDETK RNQLFERMLK VHSRGGLISA SIKAVTAADM
EARLACGLVK GHAYAVTDVR KVRLGHGLLA FFKSEKLDMI
RLRNPWGERE WNGPWSDTSE EWQKVSKSER EKMGVTVQDD
GEFWMTFEDV CRYFTDIIKC RVINTSHLSI HKTWEEARLH
GAWTLHEDPR QNRGGGCINH KDTFFQNPQY IFEVKKPEDE
EQKLISEEDL EQKLISEEDL EQKLISEEDL * hCAPN5-truncation3: 1-550 amino acids+3×myc (indicated in bold), 1743 nts, 581 amino acids DNA Sequence:

(SEQ ID NO: 8)
ATGTTCTCGTGTGTGAAGCCCTATGAGGACCAGAACTACTCAGCCCTGAG
GCGGGACTGCCGGCGCAGGAAGGTGCTCTTCGAGGACCCCCTCTTCCCCG
CCACTGACGACTCACTCTACTATAAGGGCACGCCGGGCCCGCCGTCAGG
TGGAAGCGACCCAAGGGCATCTGCGAGGACCCCCGCCTCTTTGTGGATGG
CATCAGCTCCCACGACCTGCACCAGGGCCAGGTGGGCAACTGCTGGTTTG
TGGCAGCCTGCTCGTCACTTGCCTCCCGGGAGTCGCTGTGGCAAAAGGTC
ATCCCAGACTGGAAGGAGCAGGAATGGGACCCCGAAAAGCCCAACGCCTA
CGCGGGCATCTTCCACTTCCACTTCTGGCGCTTCGGGGAATGGGTGGACG
TGGTCATCGATGACCGGCTGCCCACAGTCAACAACCAGCTCATCTACTGC
CACTCCAACTCCCGCAATGAGTTTTGGTGCGCCCTAGTGGAGAAGGCCTA
TGCCAAACTGGCAGGCTGTTACCAGGCCCTGGATGGAGGCAACACAGCAG

-continued

```
ACGCACTGGTGGACTTCACGGGTGGTGTTTCTGAGCCCATCGACCTGACC

GAGGGTGACTTTGCCAACGATGAGACTAAGAGGAACCAGCTCTTTGAGCG

CATGTTAAAGGTGCACAGCCGGGGCGGCCTCATCAGTGCCTCCATCAAGG

CAGTGACAGCAGCTGACATGGAGGCCCGCCTGGCGTGCGGCCTGGTAAAG

GGCCACGCATACGCCGTCACTGATGTGCGCAAGGTGCGCCTGGGCCACGG

CCTACTGGCCTTCTTCAAGTCAGAGAAGTTGGACATGATCCGCCTGCGCA

ACCCCTGGGGCGAGCGGGAGTGGAACGGGCCCTGGAGTGACACCTCGGAG

GAGTGGCAGAAAGTGAGCAAGAGTGAGCGGGAGAAGATGGGTGTGACCGT

GCAGGACGACGGTGAGTTCTGGATGACCTTCGAGGACGTGTGCCGGTACT

TCACGGACATCATCAAGTGCCGCGTGATCAACACATCCCACCTGAGCATC

CACAAGACGTGGGAGGAGGCCCGGCTGCATGGCGCCTGGACGCTGCATGA

GGACCCGCGACAGAACCGCGGTGGCGGCTGCATCAACCACAAGGACACCT

TCTTCCAGAACCCACAGTACATCTTCGAAGTCAAGAAGCCAGAAGATGAA

GTCCTGATCTGCATCCAGCAGCGGCCAAAGCGGTCTACGCGCCGGGAGGG

CAAGGGTGAGAACCTGGCCATTGGCTTTGACATCTACAAGGTGGAGGAGA

ACCGCCAGTACCGCATGCACAGCCTGCAGCACAAGGCCGCCAGCTCCATC

TACATCAACTCACGCAGCGTCTTCCTGCGCACCGACCAGCCCGAGGGCCG

CTATGTCATCATCCCCACAACCTTCGAGCCAGGCCACACTGGCGAGTTCC

TGCTCCGAGTCTTCACTGATGTGCCCTCCAACTGCCGGGAGCTGCGCCTG

GATGAGCCCCCACACACCTGCTGGAGCTCCCTCTGTGGCTACCCCCAGCT

GGTGACCCAGGTACATGTCCTGGGAGCTGCTGGCCTCAAGGACTCCCCAA

CAGGGGCTAACTCTTATGTGATCATCAAGTGTGAGGGAGACAAAGTCCGC

GAGCAGAAACTCATCTCAGAAGAGGATCTGGAGCAGAAACTCATCTCAGA

AGAGGATCTGGAGCAGAAACTCATCTCAGAAGAGGATCTGTGA
```

Protein Sequence:

```
                                            (SEQ ID NO: 9)
    MFSCVKPYED QNYSALRRDC RRRKVLFEDP LFPATDDSLY

YKGTPGPAVR WKRPKGICED PRLFVDGISS HDLHQGQVGN

CWFVAACSSL ASRESLWQKV IPDWKEQEWD PEKPNAYAGI

FHFHFWRFGE WVDVVIDDRL PTVNNQLIYC HSNSRNEFWC

ALVEKAYAKL AGCYQALDGG NTADALVDFT GGVSEPIDLT

EGDFANDETK RNQLFERMLK VHSRGGLISA SIKAVTAADM

EARLACGLVK GHAYAVTDVR KVRLGHGLLA FFKSEKLDMI

RLRNPWGERE WNGPWSDTSE EWQKVSKSER EKMGVTVQDD

GEFWMTFEDV CRYFTDIIKC RVINTSHLSI HKTWEEARLH

GAWTLHEDPR QNRGGGCINH KDTFFQNPQY IFEVKKPEDE

VLICIQQRPK RSTRREGKGE NLAIGFDIYK VEENRQYRMH
```

```
    SLQHKAASSI YINSRSVFLR TDQPEGRYVI IPTTFEPGHT

GEFLLRVFTD VPSNCRELRL DEPPHTCWSS LCGYPQLVTQ

VHVLGAAGLK DSPTGANSYV IIKCEGDKVR EQKLISEEDL

EQKLISEEDL EQKLISEEDL *
``` hCAPN5-truncation4: 1-100 amino acids+3×myc (indicated in bold), 393 nts, 131 amino acids DNA Sequence:

```
                                            (SEQ ID NO: 10)
ATGTTCTCGTGTGTGAAGCCCTATGAGGACCAGAACTACTCAGCCCTGAG

GCGGGACTGCCGGCGCAGGAAGGTGCTCTTCGAGGACCCCCTCTTCCCCG

CCACTGACGACTCACTCTACTATAAGGGCACGCCGGGGCCCGCCGTCAGG

TGGAAGCGACCCAAGGGCATCTGCGAGGACCCCCGCCTCTTTGTGGATGG

CATCAGCTCCCACGACCTGCACCAGGGCCAGGTGGGCAACTGCTGGTTTG

TGGCAGCCTGCTCGTCACTTGCCTCCCGGGAGTCGCTGTGGCAAAAGGTC

GAGCAGAAACTCATCTCAGAAGAGGATCTGGAGCAGAAACTCATCTCAGA

AGAGGATCTGGAGCAGAAACTCATCTCAGAAGAGGATCTGTGA
```

Protein Sequence:

```
                                            SEQ ID NO: 11)
    MFSCVKPYED QNYSALRRDC RRRKVLFEDP LFPATDDSLY

YKGTPGPAVR WKRPKGICED PRLFVDGISS HDLHQGQVGN

CWFVAACSSL ASRESLWQKV EQKLISEEDL EQKLISEEDL

EQKLISEEDL *
``` hCAPN5-truncation5: 26-343 amino acids+3×myc (indicated in bold), 1047 nts, 349 amino acids DNA Sequence:

```
                                            SEQ ID NO: 12)
CTCTTCGAGGACCCCCTCTTCCCCGCCACTGACGACTCACTCTACTATAA

GGGCACGCCGGGGCCCGCCGTCAGGTGGAAGCGACCCAAGGGCATCTGCG

AGGACCCCCGCCTCTTTGTGGATGGCATCAGCTCCCACGACCTGCACCAG

GGCCAGGTGGGCAACTGCTGGTTTGTGGCAGCCTGCTCGTCACTTGCCTC

CCGGGAGTCGCTGTGGCAAAAGGTCATCCCAGACTGGAAGGAGCAGGAAT

GGGACCCCGAAAAGCCCAACGCCTACGCGGGCATCTTCCACTTCCACTTC

TGGCGCTTCGGGGAATGGGTGGACGTGGTCATCGATGACCGGCTGCCCAC

AGTCAACAACCAGCTCATCTACTGCCACTCCAACTCCCGCAATGAGTTTT

GGTGCGCCCTAGTGGAGAAGGCCTATGCCAAACTGGCAGGCTGTTACCAG

GCCCTGGATGGAGGCAACACAGCAGACGCACTGGTGGACTTCACGGGTGG

TGTTTCTGAGCCCATCGACCTGACCGAGGGTGACTTTGCCAACGATGAGA

CTAAGAGGAACCAGCTCTTTGAGCGCATGTTAAAGGTGCACAGCCGGGGC

GGCCTCATCAGTGCCTCCATCAAGGCAGTGACAGCAGCTGACATGGAGGC

CCGCCTGGCGTGCGGCCTGGTAAAGGGCCACGCATACGCCGTCACTGATG

TGCGCAAGGTGCGCCTGGGCCACGGCCTACTGGCCTTCTTCAAGTCAGAG

AAGTTGGACATGATCCGCCTGCGCAACCCCTGGGGCGAGCGGGAGTGGAA
```

```
CGGGCCCTGGAGTGACACCTCGGAGGAGTGGCAGAAAGTGAGCAAGAGTG

AGCGGGAGAAGATGGGTGTGACCGTGCAGGACGACGGTGAGTTCTGGATG

ACCTTCGAGGACGTGTGCCGGTACTTCACGGACATCATCAAGTGCCGCGT

GATCGAGCAGAAACTCATCTCAGAAGAGGATCTGGAGCAGAAACTCATCT

CAGAAGAGGATCTGGAGCAGAAACTCATCTCAGAAGAGGATCTGTGA
```

Protein Sequence:

```
                                          SEQ ID NO: 13)
LFEDPLFPAT DDSLYYKGTP GPAVRWKRPK GICEDPRLFV

DGISSHDLHQ GQVGNCWFVA ACSSLASRES LWQKVIPDWK

EQEWDPEKPN AYAGIFHFHF WRFGEWVDVV IDDRLPTVNN

QLIYCHSNSR NEFWCALVEK AYAKLAGCYQ ALDGGNTADA

LVDFTGGVSE PIDLTEGDFA NDETKRNQLF ERMLKVHSRG

GLISASIKAV TAADMEARLA CGLVKGHAYA VTDVRKVRLG

HGLLAFFKSE KLDMIRLRNP WGEREWNGPW SDTSEEWQKV

SKSEREKMGV TVQDDGEFWM TFEDVCRYFT DIIKCRVIEQ

KLISEEDLEQ KLISEEDLEQ KLISEEDL*
``` hCAPN5-truncation6: 181-420 amino acids+3×myc (indicated in bold), 813 nts, 271 amino acids DNA Sequence:

```
                                          SEQ ID NO: 14)
AACACAGCAGACGCACTGGTGGACTTCACGGGTGGTGTTTCTGAGCCCAT

CGACCTGACCGAGGGTGACTTTGCCAACGATGAGACTAAGAGGAACCAGC

TCTTTGAGCGCATGTTAAAGGTGCACAGCCGGGGCGGCCTCATCAGTGCC

TCCATCAAGGCAGTGACAGCAGCTGACATGGAGGCCCGCCTGGCGTGCGG

CCTGGTAAAGGGCCACGCATACGCCGTCACTGATGTGCGCAAGGTGCGCC

TGGGCCACGGCCTACTGGCCTTCTTCAAGTCAGAGAAGTTGGACATGATC

CGCCTGCGCAACCCCTGGGGCGAGCGGGAGTGGAACGGGCCCTGGAGTGA

CACCTCGGAGGAGTGGCAGAAAGTGAGCAAGAGTGAGCGGGAGAAGATGG

GTGTGACCGTGCAGGACGACGGTGAGTTCTGGATGACCTTCGAGGACGTG

TGCCGGTACTTCACGGACATCATCAAGTGCCGCGTGATCAACACATCCCA

CCTGAGCATCCACAAGACGTGGGAGGAGGCCCGGCTGCATGGCGCCTGGA

CGCTGCATGAGGACCCGCGACAGAACCGCGGTGGCGGCTGCATCAACCAC

AAGGACACCTTCTTCCAGAACCCACAGTACATCTTCGAAGTCAAGAAGCC

AGAAGATGAAGTCCTGATCTGCATCCAGCAGCGGCCAAAGCGGTCTACGC

GCCGGGAGGGCAAGGGTGAGGAGCAGAAACTCATCTCAGAAGAGGATCTG

GAGCAGAAACTCATCTCAGAAGAGGATCTGGAGCAGAAACTGATCTGAGA

AGAGGATCTGTGA
```

Protein Sequence:

```
                                          SEQ ID NO: 15)
NTADALVDFT GGVSEPIDLT EGDFANDETK RNQLFERMLK

VHSRGGLISA SIKAVTAADM EARLACGLVK GHAYAVTDVR

KVRLGHGLLA FFKSEKLDMI RLRNPWGERE WNGPWSDTSE

EWQKVSKSER EKMGVTVQDD GEFWMTFEDV CRYFTDIIKC

RVINTSHLSI HKTWEEARLH GAWTLHEDPR QNRGGGCINH

KDTFFQNPQY IFEVKKPEDE VLICIQQRPK RSTRREGKGE

EQKLISEEDL EQKLISEEDL EQKLISEEDL *
``` hCAPN5-truncation7: 421-560 amino acids+3×myc (indicated in bold), 513 nts, 171 amino acids DNA Sequence:

```
                                          SEQ ID NO: 16)
AACCTGGCCATTGGCTTTGACATCTACAAGGTGGAGGAGAACCGCCAGTA

CCGCATGCACAGCCTGCAGCACAAGGCCGCCAGCTCCATCTACATCAACT

CACGCAGCGTCTTCCTGCGCACCGACCAGCCCGAGGGCCGCTATGTCATC

ATCCCCACAACCTTCGAGCCAGGCCACACTGGCGAGTTCCTGCTCCGAGT

CTTCACTGATGTGCCCTCCAACTGCCGGGAGCTGCGCCTGGATGAGCCCC

CACACACCTGCTGGAGCTCCCTCTGTGGCTACCCCCAGCTGGTGACCCAG

GTACATGTCCTGGGAGCTGCTGGCCTCAAGGACTCCCCAACAGGGGCTAA

CTCTTATGTGATCATCAAGTGTGAGGGAGACAAAGTCCGCTCGGCTGTGC

AGAAGGGCACCTCCACACCAGAGCAGAAACTCATCTCAGAAGAGGATCTG

GAGCAGAAACTCATCTCAGAAGAGGATCTGGAGCAGAAACTCATCTCAGA

AGAGGATCTGTGA
```

Protein Sequence:

```
                                          SEQ ID NO: 17)
NLAIGFDIYK VEENRQYRMH SLQHKAASSI YINSRSVFLR

TDQPEGRYVI IPTTFEPGHT GEFLLRVFTD VPSNCRELRL

DEPPHTCWSS LCGYPQLVTQ VHVLGAAGLK DSPTGANSYV

IIKCEGDKVR SAVQKGTSTP EQKLISEEDL EQKLISEEDL

EQKLISEEDL *
```

The particular locations for truncation were carefully determined. Cutting the enzyme in the middle of a helix or sheet could potentially destabilize the protein, causing it not to fold properly, precipitate and make it difficult to do cleavage tests. Thus, sections of the protein were selected that do not interrupt a secondary structure element.

Example 3

Enzyme Kinetics

In enzymatic studies, the $V_{max}$ is the maximum velocity or rate at which an enzyme catalyzes a reaction; when all enzyme active sites are saturated with substrate. The $K_m$ is the substrate concentration at which the reaction rate is half of the maximum. It is an inverse measure of affinity. Thus, a higher $K_m$ value means more substrate is needed to saturate the enzyme. FIGS. 7-11.

Example 4

Inhibitors of CAPN5

Cyclic peptides have been generated that block the binding site otherwise occupied by the 10 amino acid target peptide.

Based on comparative homology to other Calpain molecules (FIG. 5A), these inhibitors can also to inhibit other Calpain molecules.

Example 5

Specificity of CAPN5 Inhibitors

A highly specific peptide that is a proteolytic target of CAPN5 was identified. This peptide is modified to become protease resistant for use as an inhibitor.

Figures 12A, 12B, 12C, 12D:
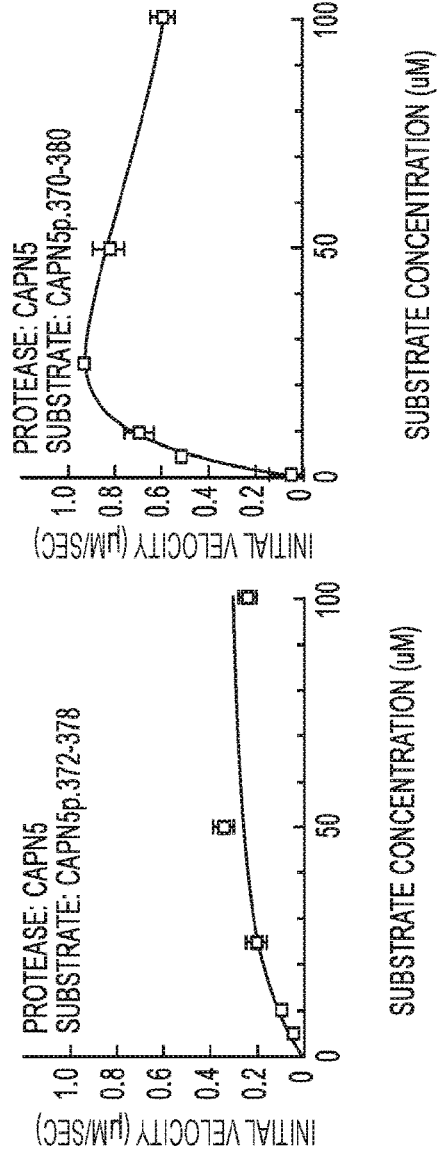
FIGS. 12A-12D. Proteolytic kinetics of CAPN5 is influenced by peptide length near its autoproteolytic site. Peptides substrates that were 7, 11, and 21 amino acids long were incubated in calpain activity buffer. The solution was brought to 37° C. CAPN5 was then added and fluorescence was measured.

Proteolytic kinetics of CAPN5 is influenced by peptide length near its autoproteolytic site. Peptides substrates that were 7, 11, and 21 amino acids long were incubated in calpain activity buffer. The solution was brought to 37° C. CAPN5 was then added and fluorescence was measured. There was mild cleavage of the 7 aa peptide was observed (FIG. 12A), and rapid and high cleavage of the 11 aa peptide (FIG. 12B). The 21 aa peptide was cleaved slower and does not show cleavage substrate inhibition (FIG. 12C). The kinetics data from the Michaelis-Menten and substrate inhibition equations are shown in a table (FIG. 12D).

The peptides that were tested showed calpain-specificity. Peptides were incubated in calpain activity buffer, and the solution was brought to 37° C. Calpain was added and fluorescence was measured. The fluorescence measured for the lead peptide, CAPN5p370-380, was plotted and lines were fit using the following substrate inhibition equation, $Y=Vmax*X/(Km+X*(1+X/Ki))$. The peptide shows high proteolysis when incubated with CAPN5-WT and very limited proteolysis when incubated with CPAN1-WT (FIG. 13A). The fluorescence measure for a previously published calpain-1 peptide, EPLFAERK (SEQ ID NO: 22), was plotted and lines were fit using the following Michaelis-Menten equation, $Y=Vmax*X/(Km+X)$ (FIG. 13B). The peptide shows high proteolysis when incubated with CAPN1-WT and very limited proteolysis when incubated with CAPN5-WT, suggesting substrate specificity. Kinetics data from the Michaelis-Menten and substrate inhibition equations are shown in a table (FIG. 13C).

Figures 14B, 14C:
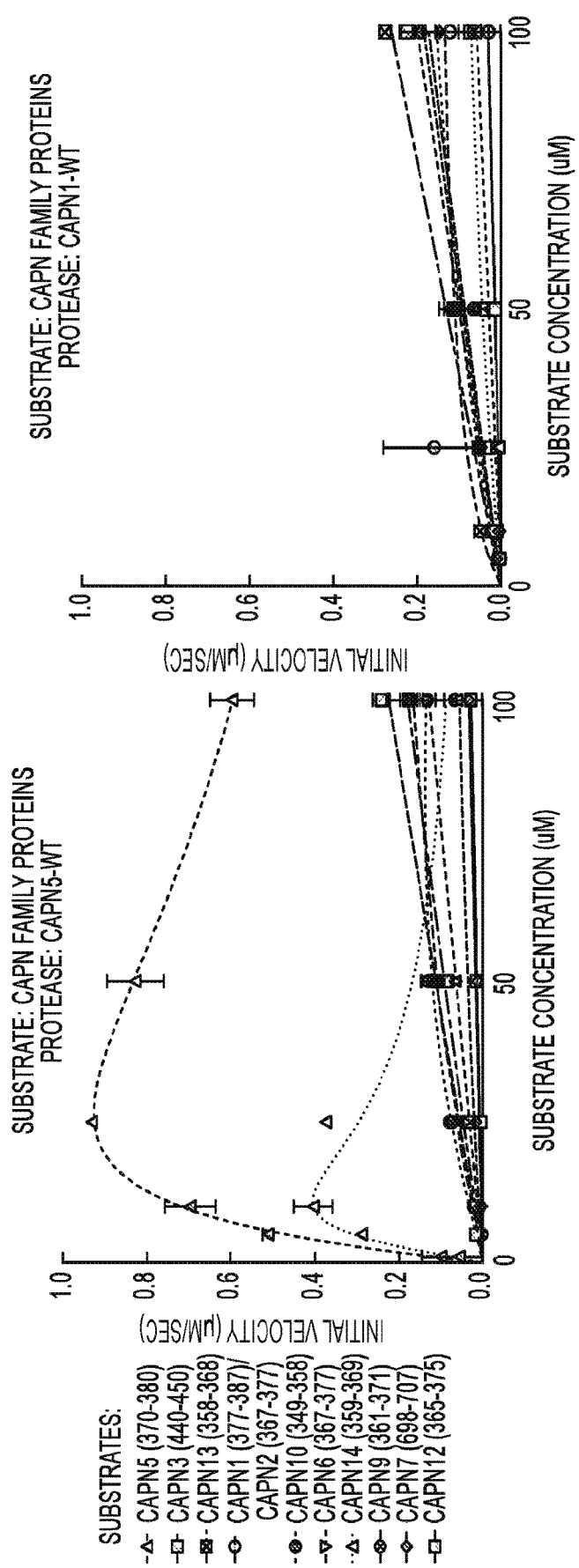

CAPN5 specifically targets a peptide corresponding to its own autocatalytic site and not homologous regions in other calpains. An alignment of the peptides shows very limited sequence homology (FIG. 14A). Peptides corresponding to the homologous regions of the CAPN5 autoprotolysis site in other calpain family members were incubated with CAPN5 protease. CAPN5 did not proteolyze homologous regions of other CAPN members as well as it proteolyzed its own site, although there was some proteolysis of the CAPN14 peptide (FIG. 14B). Peptides tested in FIG. 14B were incubated with CAPN1. CAPN1 does not appear to proteolyze these regions (FIG. 14C). Kinetics data from the Michaelis-Menten and substrate inhibitions equations are shown in a table (FIG. 14D).

Example 6

Second Generation Inhibitors

Figure 15B:
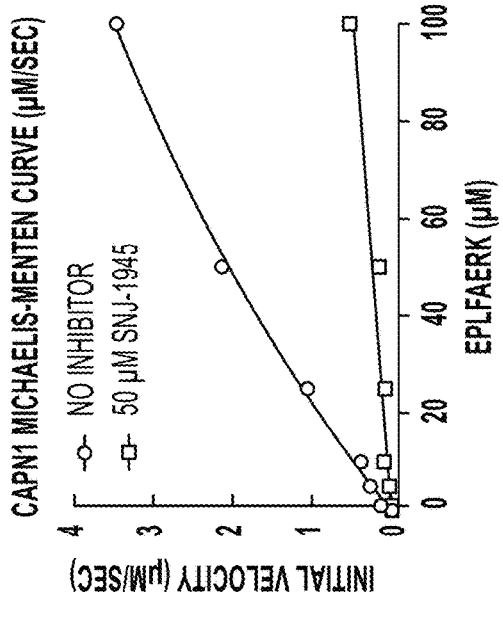
FIGS. 15A-15D: The classical calpain inhibitor SNJ-1945 inhibits CAPN1 but is not a good inhibitor of CAPN5.
Figure 15D:
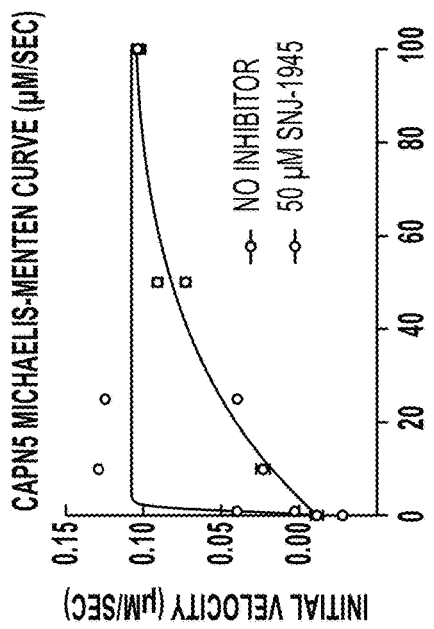
Figure 15A:
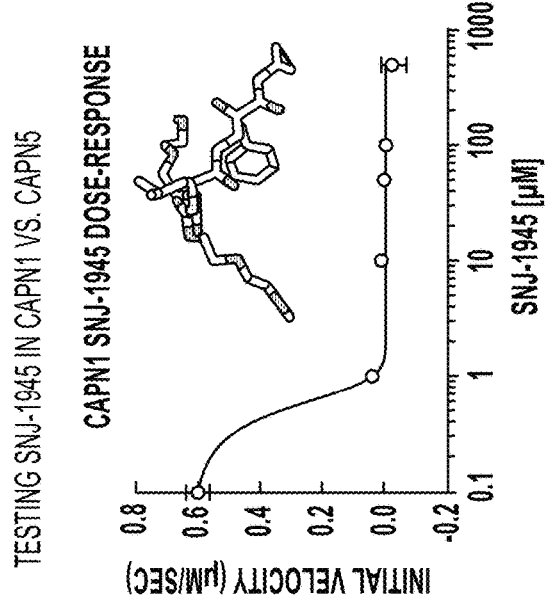
Figure 15C:
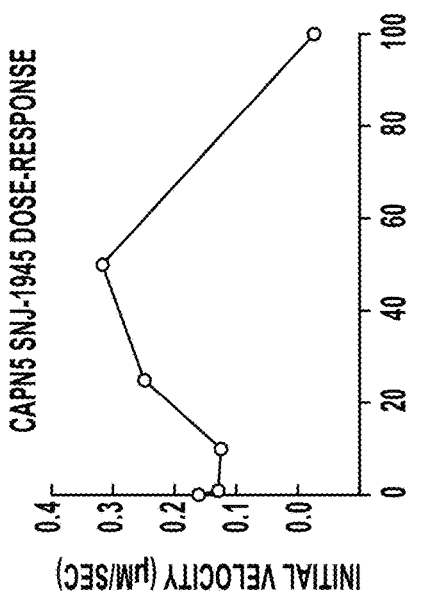

The classical calpain inhibitor SNJ-1945 inhibits CAPN1 but is not a good inhibitor of CAPN5. Various concentrations of SNJ-1945 were incubated in a reaction with 50 µM EPLFAERK (a CAPN1 substrate) (SEQ ID NO: 22) and CAPN1 WT in activity. Addition of 1 µM SNJ-1945 slows the initial reaction rate by 100% (FIG. 15A). CAPN1 WT was incubated with and without SNJ-1945 at increasing concentrations of EPLFAERK substrate (SEQ ID NO: 22) (FIG. 15B). Various concentrations of SNJ-1945 were incubated in a reaction with CAPN5p.370-80 and CAPN5 WT in an activity buffer. Only after addition of 100 µM SNJ-1945 did the initial reaction rate slow to 100% (FIG. 15C). CAPN5 WT was incubated with and without SNJ-1945 at increasing concentrations of CAPN5 p.370-80 substrate (FIG. 15D).

Figure 17:
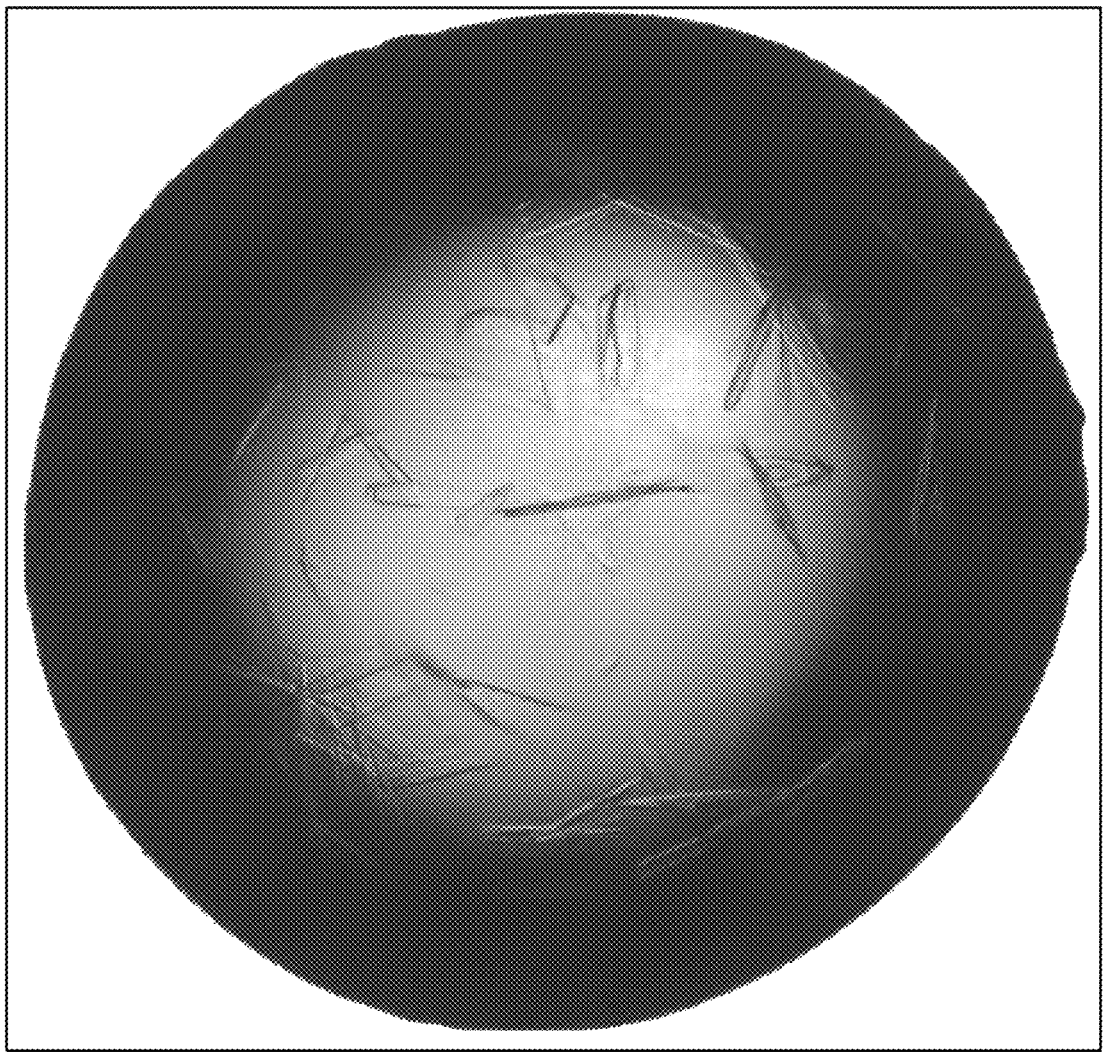
FIG. 17. Co-crystallizatoin of CAPN5 with CAPN5p370-80 peptide.

Second generation inhibitors based off lead compound competitively inhibit CAPN5. First generation lead compound CAPN5 p.370-80 was modified using amide cyclization to generate a second generation competitive cyclic inhibitor. Various concentrations of Cyclic CAPN5 p.370-80 were incubated in a reaction with CAPN5p.370-80 and CAPN5 WT in an activity buffer. Addition of 10 µM Cyclic CAPN5 p.370-80 slows the initial reaction rate by 40% (FIG. 16A). CAPN5 WT was incubated with and without 10 µM Cyclic CAPN5 p.370-80 at increasing concentrations of CAPN5 p.370-80 substrate. Increasing concentrations of substrate does not overcome inhibition by cyclic peptide (FIG. 16B). The co-crystallization of CAPN5 with CAPN5p.370-80 peptide is shown in FIG. 17.

Figure 18A:
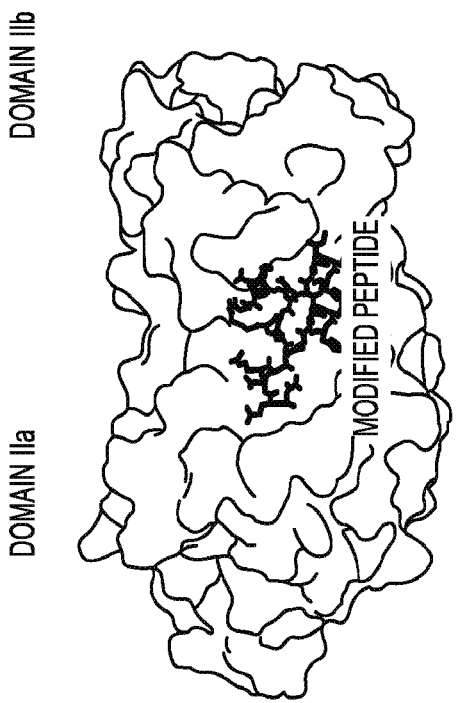
FIGS. 18A-18D. Modification of lead compound reveals potential for competitive inhibition.
Figure 18B:
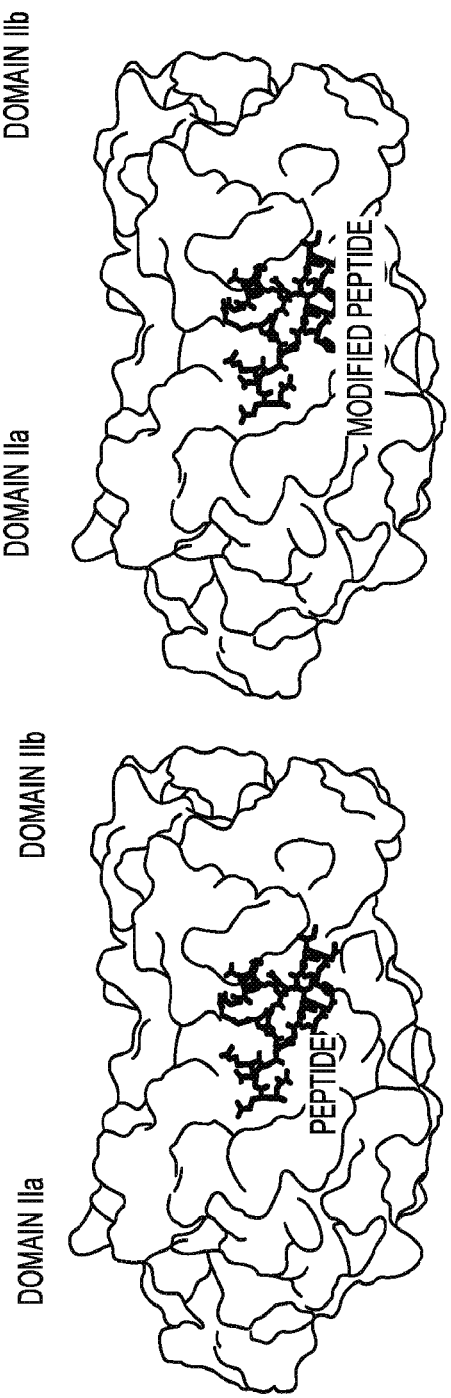
Figure 18C:
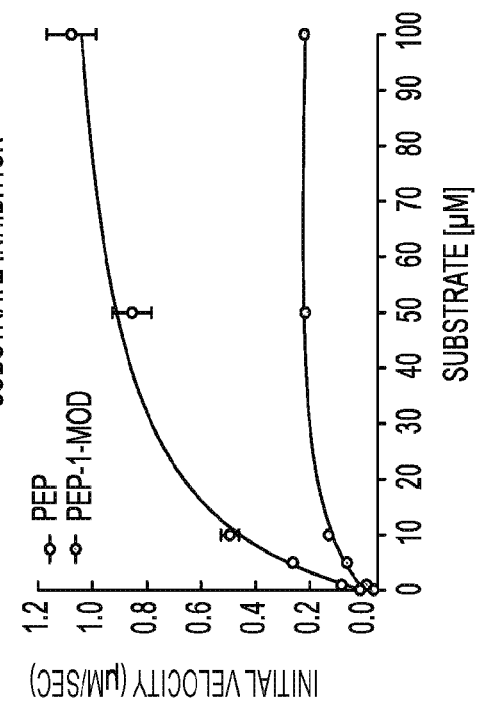
Figure 18D:
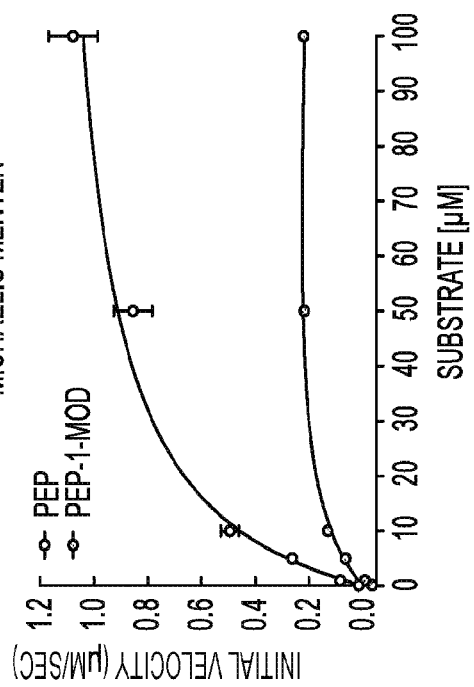
Figure 19G:
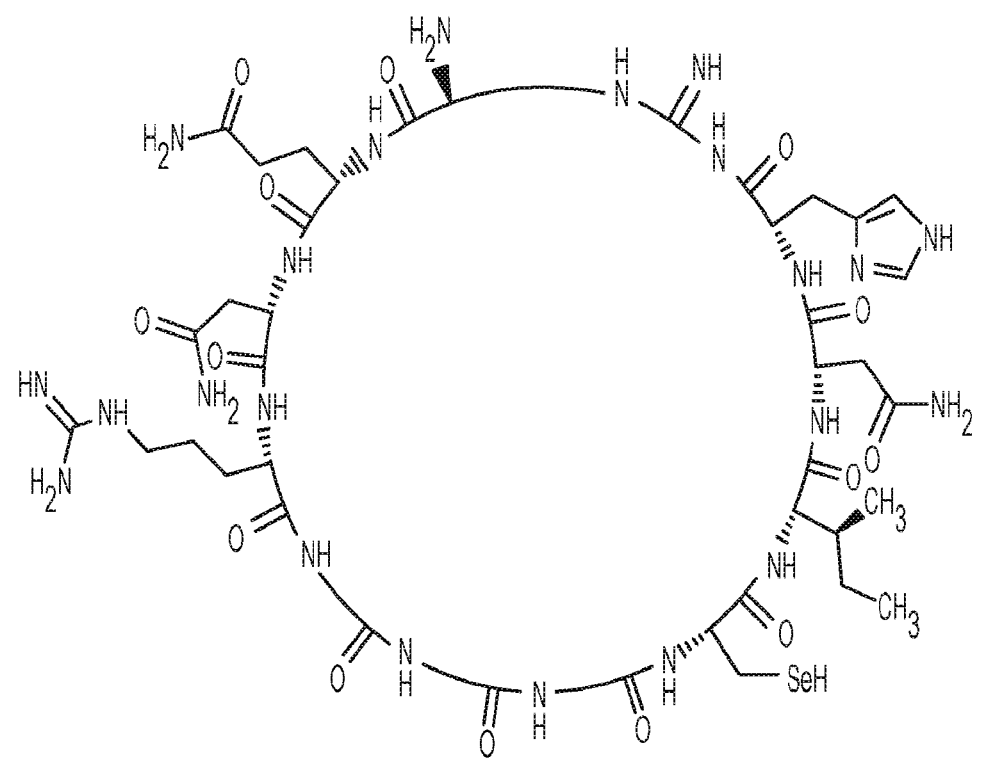

Modification of lead compound reveals potential for competitive inhibition. (A) Structural model of the CAPN5 protease core with the peptide docked to it using AutoDock VINA is shown in FIG. 18A. Scanning modifications were made to the amino acids of the lead compound to make the bonds un-cleavable by CAPN5 (FIG. 18B). Despite modifications, the peptide still fit in the catalytic groove using docking predictions. N-terminal (EDANS) and C-terminal GLU-(DABCYL) FRET tags were added to the peptides for our standard CAPN5 assay and were dissolved in 70% DMSO (FIG. 18C). Peptides incubated for 15 minutes at various concentrations with 5 µg of MBP-CAPN5 WT. Modification of the amino acids slows the reaction rate. Data is plotted as initial velocity (uM/sec) versus peptide concentration fit to the substrate inhibition equation (FIG. 18D).

Example 8

Modification and Activity of CAPN5-370-80 Peptide

Figure 20A:
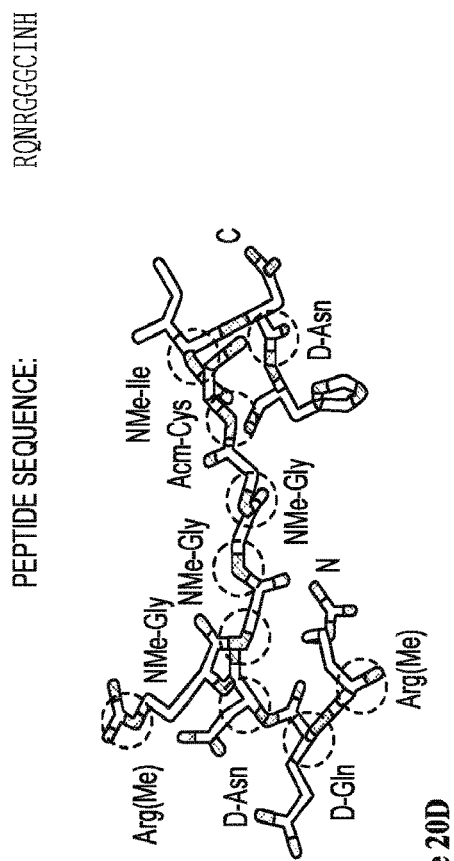
FIGS. 20A-20D. Modification and activity of CAPN5-370-80 peptide.
Figure 20B:
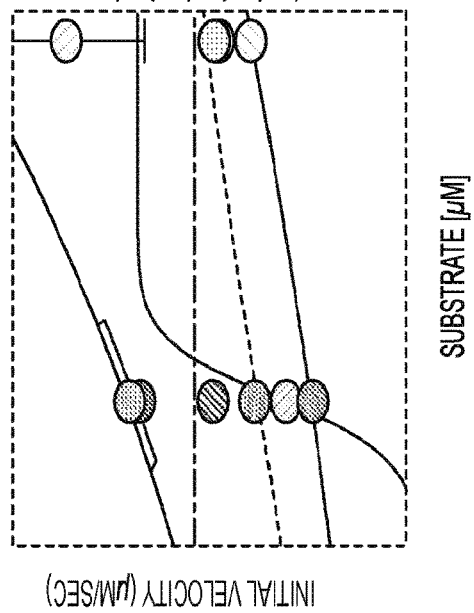
Figure 20C:
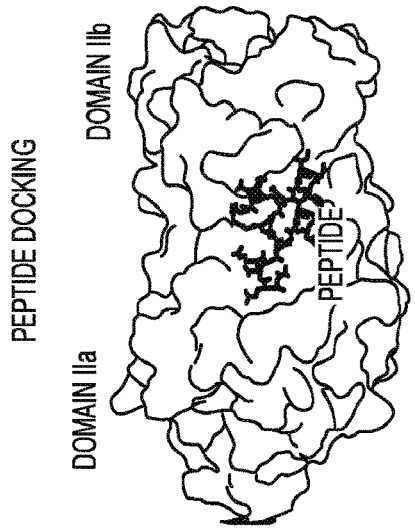
Figure 20D:
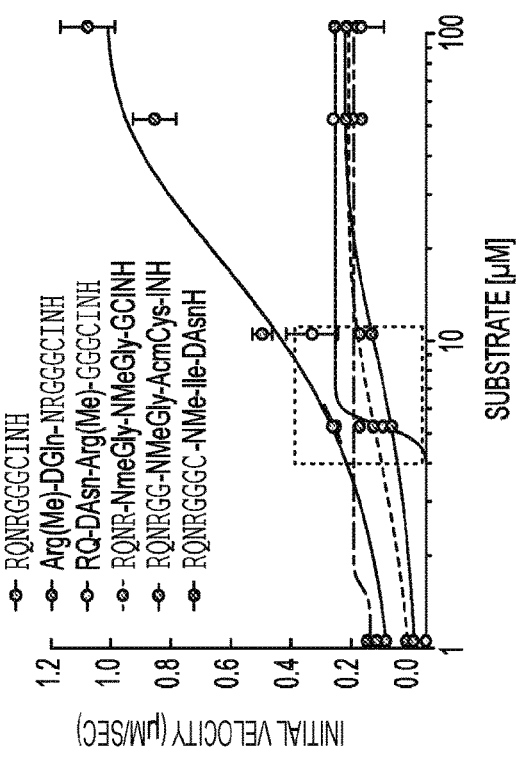

The CAPN5-370-80 peptide was modified (FIGS. 19A-19G) and the activity was evaluated (FIGS. 20A-20D). A structural model of the CAPN5 protease core with the peptide docked to it using AutoDock VINA is provided in FIG. 20A. Chemical structure of the CAPN5-370-80 peptide (RQNRGGGCINH (SEQ ID NO: 23)) is provided in FIG. 20B. Scanning modifications were made to the amino acids of the peptide to make the bonds un-cleavable by CAPN5. The location of the modifications are denoted with circles N-terminal (EDANS) and C-terminal GLU-(DABCYL) FRET tags were added to the peptides for the standard CAPN5 assay and were dissolved in 70% DMSO. Peptides incubated for 15 minutes at various concentrations with 5 µg of MBP-CAPN5 WT in a buffer containing 20 mM Tris, 300 mM NaCl, 2 mM DTT, pH 7.5 to measure activity (FIG. 20C). Data is plotted as initial velocity (uM/sec) versus peptide concentration. Modification of the amino acids slows the reaction rate. Close-up of graph region highlighting the differences in proteolytic activity at 5 μM substrate is provided in FIG. 20D.

Example 9

Testing of Classical Calpain Inhibitors for CAPN5

Figure 21:
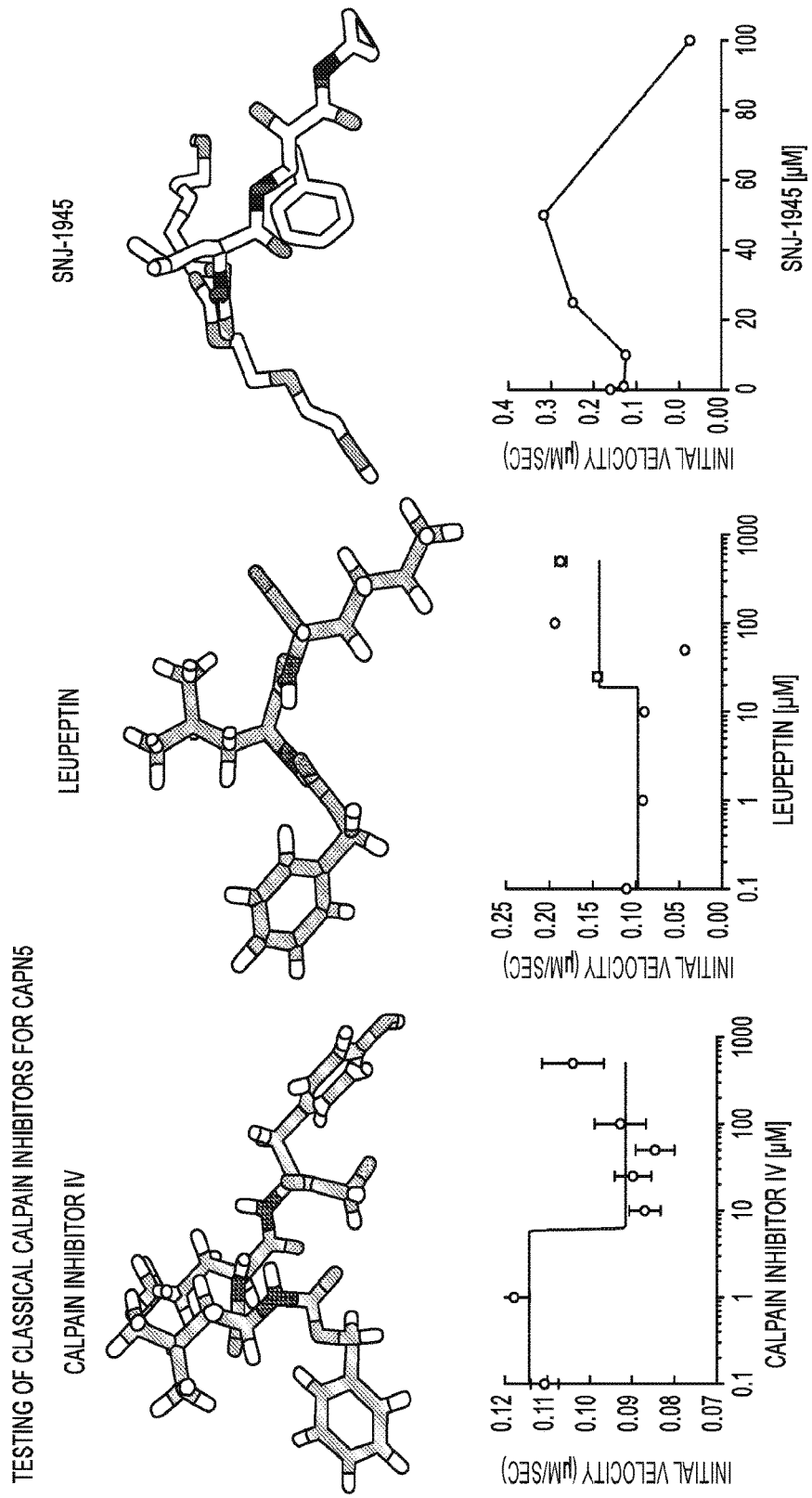
FIG. 21. Results from the testing of classical calpain inhibitors Calpain Inhibitor IV, Leupeptin and SNJ-1945 are provided.

Results from the testing of classical calpain inhibitors Calpain Inhibitor IV, Leupeptin and SNJ-1945 are provided in FIG. 21.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A labelled CAPN5 substrate consisting of
a peptide selected from the group consisting of SEQ ID NO:20 and not more than 9 additional amino acids, SEQ ID NO:21 and not more than 9 additional amino acids, or SEQ ID NO:23 and not more than 19 additional amino acids, and
a detection agent consisting of a fluorescent or colorimetric agent to form the labelled CAPN5 substrate.

2. The CAPN5 substrate of claim 1, wherein the peptide is labelled CAPN5-370-380 (SEQ ID NO:23).

3. The labelled CAPN5 substrate of claim 1, wherein the peptide contains an unnatural amino acid residue.

4. The labelled CAPN5 substrate according to claim 1, wherein the peptide contains a methylated amino acid residue.

5. The labelled CAPN5 substrate according to claim 3, wherein methylated amino acid residue is methyl-arginine, methyl-glycine, or methyl-isoleucine.

6. The labelled CAPN5 substrate according to claim 3, wherein the unnatural amino acid residue is a D-amino acid.

7. The labelled CAPN5 substrate according to claim 3, wherein the D-amino acid is D-glutamine or D-asparagine.

8. The labelled CAPN5 substrate according to claim 3, wherein the unnatural amino acid residue is Acm-cysteine.

9. The labelled CAPN5 substrate of claim 1, wherein the peptide is soluble in aqueous solutions.

10. A composition comprising the labelled CAPN5 substrate of claim 1 and a physiologically acceptable carrier.

11. A solution comprising a carrier and a labelled CAPN5 substrate of claim 1 dispersed in the carrier.

12. A method of detecting CAPN5 comprising administering the labelled CAPN5 substrate of claim 1.

13. The CAPN5 substrate of claim 1, wherein the peptide is labelled CAPN5-370-390 (SEQ ID NO:20).

14. The CAPN5 substrate of claim 1, wherein the peptide is labelled CAPN5-390-410 (SEQ ID NO:21).

* * * * *

UNITED STATES PATENT AND TRADEMARK OFFICE
CERTIFICATE OF CORRECTION

| | |
|---|---|
| PATENT NO. | : 11,981,943 B2 |
| APPLICATION NO. | : 16/340657 |
| DATED | : May 14, 2024 |
| INVENTOR(S) | : Mahajan et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 888 days.

Signed and Sealed this
First Day of April, 2025

Coke Morgan Stewart
*Acting Director of the United States Patent and Trademark Office*

SEQUENCE LISTING

```
<160> NUMBER OF SEQ ID NOS: 45

<210> SEQ ID NO 1
<211> LENGTH: 1923
<212> TYPE: DNA
<213> ORGANISM: Homo sapiens

<400> SEQUENCE: 1
atgttctcgt gtgtgaagcc ctatgaggac cagaactact cagccctgag gcgggactgc      60
cggcgcagga aggtgctctt cgaggacccc ctcttccccg ccactgacga ctcactctac     120
tataagggca cgccggggcc cgccgtcagg tggaagcgac ccaagggcat ctgcgaggac     180
ccccgcctct ttgtggatgg catcagctcc cacgacctgc accagggcca ggtgggcaac     240
tgctggtttg tggcagcctg ctcgtcactt gcctcccggg agtcgctgtg gcaaaaggtc     300
atcccagact ggaaggagca ggaatgggac cccgaaaagc ccaacgccta cgcgggcatc     360
ttccacttcc acttctggcg cttcggggaa tgggtggacg tggtcatcga tgaccggctg     420
cccacagtca acaaccagct catctactgc cactccaact cccgcaatga gttttggtgc     480
gccctagtgg agaaggccta tgccaaactg gcaggctgtt accaggccct ggatggaggc     540
aacacagcag acgcactggt ggacttcacg ggtggtgttt ctgagcccat cgacctgacc     600
gagggtgact tgccaacgat gagactaag aggaaccagc tctttgagcg catgttaaag     660
gtgcacagcc ggggcggcct catcagtgcc tccatcaagg cagtgacagc agctgacatg     720
gaggcccgcc tggcgtgcgg cctggtaaag gccacgcat acgccgtcac tgatgtgcgc     780
aaggtgcgcc tgggccacgg cctactggcc ttcttcaagt cagagaagtt ggacatgatc     840
cgcctgcgca acccctgggg cgagcgggag tggaacgggc cctggagtga cacctcggag     900
gagtggcaga aagtgagcaa gagtgagcgg gagaagatgg gtgtgaccgt gcaggacgac     960
```

```
ggtgagttct ggatgacctt cgaggacgtg tgccggtact tcacggacat catcaagtgc    1020
cgcgtgatca acacatccca cctgagcatc cacaagacgt gggaggaggc ccggctgcat    1080
ggcgcctgga cgctgcatga ggacccgcga cagaaccgcg gtggcggctg catcaaccac    1140
aaggacacct tcttccagaa cccacagtac atcttcgaag tcaagaagcc agaagatgaa    1200
gtcctgatct gcatccagca gcggccaaag cggtctacgc gccgggaggg caagggtgag    1260
aacctggcca tttggctttga catctacaag gtggaggaga accgccagta ccgcatgcac    1320
agcctgcagc acaaggccgc cagctccatc tacatcaact cacgcagcgt cttcctgcgc    1380
accgaccagc ccgagggccg ctatgtcatc atccccacaa ccttcgagcc aggccacact    1440
ggcgagttcc tgctccgagt cttcactgat gtgccctcca actgccggga gctgcgcctg    1500
gatgagcccc cacacacctg ctggagctcc ctctgtggct accccagct ggtgacccag    1560 gtacatgtcc tgggagctgc tggcctcaag gactccccaa caggggctaa ctcttatgtg    1620
atcatcaagt gtgagggaga caaagtccgc tcggctgtgc agaagggcac ctccacacca    1680
gagtacaatg tgaaaggcat cttctaccgc aagaagctga gccagcccat cactgtacag    1740
gtctggaacc accgagtgct gaaggatgaa tttctgggcc aggtgcacct aaaggctgac    1800
ccggacaacc tccaggccct gcataccctc cacctccggg accgaaatag ccggcagccc    1860
agcaacctgc aggcactgt ggccgtgcac attctcagca gcacctccct catggctgtc    1920
tga                                                                  1923

<210> SEQ ID NO 2
<211> LENGTH: 2013
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgttctcgt gtgtgaagcc ctatgaggac cagaactact cagccctgag gcgggactgc     60
cggcgcagga aggtgctctt cgaggacccc ctcttccccg ccactgacga ctcactctac    120
tataagggca cgccggggcc cgccgtcagg tggaagcgac ccaagggcat ctgcgaggac    180
ccccgcctct tgtggatgg catcagctcc cacgacctgc caccagggcca ggtgggcaac    240 tgctggtttg tggcagcctg ctcgtcactt gcctcccggg agtcgctgtg caaaaggtc    300 atcccagact ggaaggagca ggaatgggac cccgaaaagc ccaacgccta cgcgggcatc    360
ttccacttcc acttctggcg cttcggggaa tgggtggacg tggtcatcga tgaccggctg    420
cccacagtca acaaccagct catctactgc cactccaact cccgcaatga gttttggtgc    480
gccctagtgg agaaggccta tgccaaactg gcaggctgtt accaggccct ggatggaggc    540
aacacagcag acgcactggt ggacttcacg ggtggtgttt ctgagcccat cgacctgacc    600
gagggtgact ttgccaacga tgagactaag aggaaccagc tctttgagcg catgttaaag    660
gtgcacagcc ggggcggcct catcagtgcc tccatcaagg cagtgacagc agctgacatg    720
gaggcccgcc tggcgtgcgg cctggtaaag gccacgcat acgccgtcac tgatgtgcgc    780
aaggtgcgcc tgggccacgg cctactggcc ttcttcaagt cagagaagtt ggacatgatc    840
cgcctgcgca accccctgggg cgagcgggag tggaacgggc cctggagtga cacctcggag    900
gagtggcaga aagtgagcaa gagtgagcgg gagaagatgg gtgtgaccgt gcaggacgac    960
ggtgagttct ggatgacctt cgaggacgtg tgccggtact tcacggacat catcaagtgc   1020
```

```
cgcgtgatca acacatccca cctgagcatc cacaagacgt gggaggaggc ccggctgcat    1080
ggcgcctgga cgctgcatga ggacccgcga cagaaccgcg gtggcggctg catcaaccac    1140
aaggacacct tcttccagaa cccacagtac atcttcgaag tcaagaagcc agaagatgaa    1200
gtcctgatct gcatccagca gcggccaaag cggtctacgc gccgggaggg caagggtgag    1260
aacctggcca ttggctttga catctacaag gtggaggaga accgccagta ccgcatgcac    1320
agcctgcagc acaaggccgc cagctccatc tacatcaact cacgcagcgt cttcctgcgc    1380
accgaccagc ccgagggccg ctatgtcatc atccccacaa ccttcgagcc aggccacact    1440
ggcgagttcc tgctccgagt cttcactgat gtgccctcca actgccggga gctgcgcctg    1500
gatgagcccc cacacacctg ctggagctcc ctctgtggct accccagct ggtgacccag    1560 gtacatgtcc tgggagctgc tggcctcaag gactccccaa caggggctaa ctcttatgtg    1620
atcatcaagt gtgagggaga caaagtccgc tcggctgtgc agaagggcac ctccacacca    1680
gagtacaatg tgaaaggcat cttctaccgc aagaagctga ccagcccat cactgtacag    1740 gtctggaacc accgagtgct gaaggatgaa tttctgggcc aggtgcacct aaaggctgac    1800
ccggacaacc tccaggccct gcataccctc cacctccggg accgaaatag ccggcagccc    1860
agcaacctgc caggcactgt ggccgtgcac attctcagca gcacctccct catggctgtc    1920
gagcagaaac tcatctcaga agaggatctg gagcagaaac tcatctcaga agaggatctg    1980
gagcagaaac tcatctcaga agaggatctg tga                                 2013

<210> SEQ ID NO 3
<211> LENGTH: 670
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Phe Ser Cys Val Lys Pro Tyr Glu Asp Gln Asn Tyr Ser Ala Leu
1               5                   10                  15

Arg Arg Asp Cys Arg Arg Lys Val Leu Phe Glu Asp Pro Leu Phe
            20                  25                  30

Pro Ala Thr Asp Asp Ser Leu Tyr Tyr Lys Gly Thr Pro Gly Pro Ala
        35                  40                  45

Val Arg Trp Lys Arg Pro Lys Gly Ile Cys Glu Asp Pro Arg Leu Phe
    50                  55                  60

Val Asp Gly Ile Ser Ser His Asp Leu His Gln Gly Gln Val Gly Asn
65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asp Pro Glu
            100                 105                 110

Lys Pro Asn Ala Tyr Ala Gly Ile Phe His Phe His Phe Trp Arg Phe
        115                 120                 125

Gly Glu Trp Val Asp Val Val Ile Asp Asp Arg Leu Pro Thr Val Asn
    130                 135                 140

Asn Gln Leu Ile Tyr Cys His Ser Asn Ser Arg Asn Glu Phe Trp Cys
145                 150                 155                 160

Ala Leu Val Glu Lys Ala Tyr Ala Lys Leu Ala Gly Cys Tyr Gln Ala
                165                 170                 175
```

-continued

Leu Asp Gly Gly Asn Thr Ala Asp Ala Leu Val Asp Phe Thr Gly
            180                 185                 190

Val Ser Glu Pro Ile Asp Leu Thr Glu Gly Asp Phe Ala Asn Asp Glu
            195                 200                 205

Thr Lys Arg Asn Gln Leu Phe Glu Arg Met Leu Lys Val His Ser Arg
        210                 215                 220

Gly Gly Leu Ile Ser Ala Ser Ile Lys Ala Val Thr Ala Ala Asp Met
225                 230                 235                 240

Glu Ala Arg Leu Ala Cys Gly Leu Val Lys Gly His Ala Tyr Ala Val
                245                 250                 255

Thr Asp Val Arg Lys Val Arg Leu Gly His Gly Leu Leu Ala Phe Phe
            260                 265                 270

Lys Ser Glu Lys Leu Asp Met Ile Arg Leu Arg Asn Pro Trp Gly Glu
        275                 280                 285

Arg Glu Trp Asn Gly Pro Trp Ser Asp Thr Ser Glu Glu Trp Gln Lys
    290                 295                 300

Val Ser Lys Ser Glu Arg Glu Lys Met Gly Val Thr Val Gln Asp Asp
305                 310                 315                 320

Gly Glu Phe Trp Met Thr Phe Glu Asp Val Cys Arg Tyr Phe Thr Asp
                325                 330                 335

Ile Ile Lys Cys Arg Val Ile Asn Thr Ser His Leu Ser Ile His Lys
            340                 345                 350

Thr Trp Glu Glu Ala Arg Leu His Gly Ala Trp Thr Leu His Glu Asp
        355                 360                 365

Pro Arg Gln Asn Arg Gly Gly Gly Cys Ile Asn His Lys Asp Thr Phe
    370                 375                 380

Phe Gln Asn Pro Gln Tyr Ile Phe Glu Val Lys Lys Pro Glu Asp Glu
385                 390                 395                 400

Val Leu Ile Cys Ile Gln Gln Arg Pro Lys Arg Ser Thr Arg Arg Glu
                405                 410                 415

Gly Lys Gly Glu Asn Leu Ala Ile Gly Phe Asp Ile Tyr Lys Val Glu
            420                 425                 430

Glu Asn Arg Gln Tyr Arg Met His Ser Leu Gln His Lys Ala Ala Ser
        435                 440                 445

Ser Ile Tyr Ile Asn Ser Arg Ser Val Phe Leu Arg Thr Asp Gln Pro
    450                 455                 460

Glu Gly Arg Tyr Val Ile Ile Pro Thr Thr Phe Glu Pro Gly His Thr
465                 470                 475                 480

Gly Glu Phe Leu Leu Arg Val Phe Thr Asp Val Pro Ser Asn Cys Arg
                485                 490                 495

Glu Leu Arg Leu Asp Glu Pro Pro His Thr Cys Trp Ser Ser Leu Cys
            500                 505                 510

Gly Tyr Pro Gln Leu Val Thr Gln Val His Val Leu Gly Ala Ala Gly
        515                 520                 525

Leu Lys Asp Ser Pro Thr Gly Ala Asn Ser Tyr Val Ile Ile Lys Cys
    530                 535                 540

Glu Gly Asp Lys Val Arg Ser Ala Val Gln Lys Gly Thr Ser Thr Pro
545                 550                 555                 560

Glu Tyr Asn Val Lys Gly Ile Phe Tyr Arg Lys Lys Leu Ser Gln Pro
                565                 570                 575

Ile Thr Val Gln Val Trp Asn His Arg Val Leu Lys Asp Glu Phe Leu
            580                 585                 590

Gly Gln Val His Leu Lys Ala Asp Pro Asp Asn Leu Gln Ala Leu His

```
                    595                 600                 605
Thr Leu His Leu Arg Asp Arg Asn Ser Arg Gln Pro Ser Asn Leu Pro
        610                 615                 620

Gly Thr Val Ala Val His Ile Leu Ser Ser Thr Ser Leu Met Ala Val
625                 630                 635                 640

Glu Gln Lys Leu Ile Ser Glu Glu Asp Leu Gln Lys Leu Ile Ser
                645                 650                 655

Glu Glu Asp Leu Glu Gln Lys Leu Ile Ser Glu Glu Asp Leu
                660                 665                 670

<210> SEQ ID NO 4
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgttctcgt gtgtgaagcc ctatgaggac cagaactact cagccctgag gcgggactgc      60
cggcgcagga aggtgctctt cgaggacccc ctcttccccg ccactgacga ctcactctac     120
tataagggca cgccggggcc cgccgtcagg tggaagcgac ccaagggcat ctgcgaggac     180
ccccgcctct ttgtggatgg catcagctcc acgacctgc accagggcca ggtgggcaac      240
tgctggtttg tggcagcctg ctcgtcactt gcctcccggg agtcgctgtg gcaaaaggtc     300
atcccagact ggaaggagca ggaatgggac cccgaaaagc caacgcctac gcgggcatc      360 ttccacttcc acttctggcg cttcggggaa tgggtggacg tggtcatcga tgaccggctg     420
cccacagtca caaccagct catctactgc cactccaact cccgcaatga gttttggtgc      480
gccctagtgg agaaggccta tgccaaactg gcaggctgtt accaggccct ggatggaggc     540
aacacagcag acgcactggt ggacttcacg gtggtgttt ctgagcccat cgacctgacc      600
gagcagaaac tcatctcaga agaggatctg gagcagaaac tcatctcaga agaggatctg     660
gagcagaaac tcatctcaga agaggatctg tga                                  693

<210> SEQ ID NO 5
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Phe Ser Cys Val Lys Pro Tyr Glu Asp Gln Asn Tyr Ser Ala Leu
1               5                   10                  15

Arg Arg Asp Cys Arg Arg Arg Lys Val Leu Phe Glu Asp Pro Leu Phe
                20                  25                  30

Pro Ala Thr Asp Asp Ser Leu Tyr Tyr Lys Gly Thr Pro Gly Pro Ala
            35                  40                  45

Val Arg Trp Lys Arg Pro Lys Gly Ile Cys Glu Asp Pro Arg Leu Phe
        50                  55                  60

Val Asp Gly Ile Ser Ser His Asp Leu His Gln Gly Gln Val Gly Asn
65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asp Pro Glu
```

|  |  | 100 |  |  |  | 105 |  |  |  | 110 |  |  |
|---|---|---|---|---|---|---|---|---|---|---|---|---|

Lys Pro Asn Ala Tyr Ala Gly Ile Phe His Phe His Phe Trp Arg Phe
              115                 120                 125

Gly Glu Trp Val Asp Val Val Ile Asp Asp Arg Leu Pro Thr Val Asn
        130                 135                 140

Asn Gln Leu Ile Tyr Cys His Ser Asn Ser Arg Asn Glu Phe Trp Cys
145                 150                 155                 160

Ala Leu Val Glu Lys Ala Tyr Ala Lys Leu Ala Gly Cys Tyr Gln Ala
                165                 170                 175

Leu Asp Gly Gly Asn Thr Ala Asp Ala Leu Val Asp Phe Thr Gly Gly
            180                 185                 190

Val Ser Glu Pro Ile Asp Leu Thr Glu Gln Lys Leu Ile Ser Glu Glu
        195                 200                 205

Asp Leu Glu Gln Lys Leu Ile Ser Glu Glu Asp Leu Glu Gln Lys Leu
    210                 215                 220

Ile Ser Glu Glu Asp Leu
225                 230

<210> SEQ ID NO 6
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

| | | |
|---|---|---|
| atgttctcgt gtgtgaagcc ctatgaggac cagaactact cagccctgag gcgggactgc | 60 |
| cggcgcagga aggtgctctt cgaggacccc ctcttccccg ccactgacga ctcactctac | 120 |
| tataagggca cgccggggcc cgccgtcagg tggaagcgac ccaagggcat ctgcgaggac | 180 |
| ccccgcctct ttgtggatgg catcagctcc cacgacctgc accagggcca ggtgggcaac | 240 |
| tgctggtttg tggcagcctg ctcgtcactt gcctcccggg agtcgctgtg caaaaggtc | 300 |
| atcccagact ggaaggagca ggaatgggac cccgaaaagc caacgccta cgcgggcatc | 360 |
| ttccacttcc acttctggcg cttcgggaa tgggtggacg tggtcatcga tgaccggctg | 420 |
| cccacagtca caaccagct catctactgc cactccaact cccgcaatga gttttggtgc | 480 |
| gccctagtgg agaaggccta tgccaaactg gcaggctgtt accaggccct ggatggaggc | 540 |
| aacacagcag acgcactggt ggacttcacg ggtggtgttt ctgagcccat cgacctgacc | 600 |
| gagggtgact tgccaacga tgagactaag aggaaccagc tctttgagcg catgttaaag | 660 |
| gtgcacagcc gggcggcct catcagtgcc tccatcaagg cagtgacagc agctgacatg | 720 |
| gaggcccgcc tggcgtgcgg cctggtaaag ggccacgcat acgccgtcac tgatgtgcgc | 780 |
| aaggtgcgcc tgggccacgg cctactggcc ttcttcaagt cagagaagtt ggacatgatc | 840 |
| cgcctgcgca ccccctgggg cgagcgggag tggaacgggc cctggagtga cctcggag | 900 |
| gagtggcaga aagtgagcaa gagtgagcgg agaagatgg gtgtgaccgt gcaggacgac | 960 |
| ggtgagttct ggatgacctt cgaggacgtg tgccggtact tcacggacat catcaagtgc | 1020 |
| cgcgtgatca acacatccca cctgagcatc acaagacgt gggaggaggc ccggctgcat | 1080 |
| ggcgcctgga cgctgcatga ggacccgcga cagaaccgcg tggcggctg catcaaccac | 1140 |
| aaggacacct tcttccagaa cccacagtac atcttcgaag tcaagaagcc agaagatgaa | 1200 |
| gagcagaaac tcatctcaga agaggatctg gagcagaaac tcatctcaga agaggatctg | 1260 | gagcagaaac tcatctcaga agaggatctg tga                            1293

<210> SEQ ID NO 7
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Phe Ser Cys Val Lys Pro Tyr Glu Asp Gln Asn Tyr Ser Ala Leu
1               5                   10                  15

Arg Arg Asp Cys Arg Arg Lys Val Leu Phe Glu Asp Pro Leu Phe
            20                  25                  30

Pro Ala Thr Asp Asp Ser Leu Tyr Tyr Lys Gly Thr Pro Gly Pro Ala
        35                  40                  45

Val Arg Trp Lys Arg Pro Lys Gly Ile Cys Glu Asp Pro Arg Leu Phe
    50                  55                  60

Val Asp Gly Ile Ser Ser His Asp Leu His Gln Gly Gln Val Gly Asn
65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asp Pro Glu
            100                 105                 110

Lys Pro Asn Ala Tyr Ala Gly Ile Phe His Phe His Phe Trp Arg Phe
        115                 120                 125

Gly Glu Trp Val Asp Val Val Ile Asp Asp Arg Leu Pro Thr Val Asn
    130                 135                 140

Asn Gln Leu Ile Tyr Cys His Ser Asn Ser Arg Asn Glu Phe Trp Cys
145                 150                 155                 160

Ala Leu Val Glu Lys Ala Tyr Ala Lys Leu Ala Gly Cys Tyr Gln Ala
                165                 170                 175

Leu Asp Gly Gly Asn Thr Ala Asp Ala Leu Val Asp Phe Thr Gly Gly
            180                 185                 190

Val Ser Glu Pro Ile Asp Leu Thr Glu Gly Asp Phe Ala Asn Asp Glu
        195                 200                 205

Thr Lys Arg Asn Gln Leu Phe Glu Arg Met Leu Lys Val His Ser Arg
    210                 215                 220

Gly Gly Leu Ile Ser Ala Ser Ile Lys Ala Val Thr Ala Ala Asp Met
225                 230                 235                 240

Glu Ala Arg Leu Ala Cys Gly Leu Val Lys Gly His Ala Tyr Ala Val
                245                 250                 255

Thr Asp Val Arg Lys Val Arg Leu Gly His Gly Leu Leu Ala Phe Phe
            260                 265                 270

Lys Ser Glu Lys Leu Asp Met Ile Arg Leu Arg Asn Pro Trp Gly Glu
        275                 280                 285

Arg Glu Trp Asn Gly Pro Trp Ser Asp Thr Ser Glu Trp Gln Lys
    290                 295                 300

Val Ser Lys Ser Glu Arg Glu Lys Met Gly Val Thr Val Gln Asp Asp
305                 310                 315                 320

Gly Glu Phe Trp Met Thr Phe Glu Asp Val Cys Arg Tyr Phe Thr Asp
                325                 330                 335

Ile Ile Lys Cys Arg Val Ile Asn Thr Ser His Leu Ser Ile His Lys
            340                 345                 350
```

Thr Trp Glu Glu Ala Arg Leu His Gly Ala Trp Thr Leu His Glu Asp
            355                 360                 365

Pro Arg Gln Asn Arg Gly Gly Gly Cys Ile Asn His Lys Asp Thr Phe
        370                 375                 380

Phe Gln Asn Pro Gln Tyr Ile Phe Glu Val Lys Lys Pro Glu Asp Glu
385                 390                 395                 400

Glu Gln Lys Leu Ile Ser Glu Glu Asp Leu Glu Gln Lys Leu Ile Ser
            405                 410                 415

Glu Glu Asp Leu Glu Gln Lys Leu Ile Ser Glu Glu Asp Leu
            420                 425                 430

<210> SEQ ID NO 8
<211> LENGTH: 1743
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgttctcgt gtgtgaagcc ctatgaggac cagaactact cagccctgag gcgggactgc        60
cggcgcagga aggtgctctt cgaggacccc ctcttccccg ccactgacga ctcactctac       120
tataagggca cgccggggcc cgccgtcagg tggaagcgac ccaagggcat ctgcgaggac       180
ccccgcctct ttgtggatgg catcagctcc acgacctgc accagggcca ggtgggcaac        240
tgctggtttg tggcagcctg ctcgtcactt gcctcccggg agtcgctgtg caaaaggtc        300 atcccagact ggaaggagca ggaatgggac ccgaaaagc caacgcccta cgcgggcatc        360
ttccacttcc acttctggcg cttcgggaa tgggtggacg tggtcatcga tgaccggctg        420
cccacagtca caaccagct catctactgc cactccaact cccgcaatga gttttggtgc        480
gccctagtgg agaaggccta tgccaaactg gcaggctgtt accaggccct ggatggaggc       540
aacacagcag acgcactggt ggacttcacg ggtggtgttt ctgagcccat cgacctgacc       600
gagggtgact ttgccaacga tgagactaag aggaaccagc tctttgagcg catgttaaag       660
gtgcacagcc gggcggcct catcagtgcc tccatcaagg cagtgacagc agctgacatg       720
gaggcccgcc tggcgtgcgg cctggtaaag ggccacgcat acgccgtcac tgatgtgcgc       780
aaggtgcgcc tggccacgg cctactggcc ttcttcaagt cagagaagtt ggacatgatc        840
cgcctgcgca cccctgggg cgagcgggag tggaacgggc cctggagtga cacctcggag       900
gagtggcaga agtgagcaa gagtgagcgg gagaagatgg gtgtgaccgt gcaggacgac       960
ggtgagttct ggatgacctt cgaggacgtg tgccggtact tcacggacat catcaagtgc      1020
cgcgtgatca cacatcccca cctgagcatc cacaagacgt gggaggaggc ccggctgcat      1080
ggcgcctgga cgctgcatga ggacccgcga cagaaccgcg gtggcggctg catcaaccac      1140
aaggacacct tcttccagaa cccacagtac atcttcgaag tcaagaagcc agaagatgaa      1200
gtcctgatct gcatccagca gcggccaaag cggtctacgc gccgggaggg caagggtgag      1260
aacctggcca ttggctttga catctacaag gtggaggaga accgccagta ccgcatgcac      1320
agcctgcagc acaaggccgc cagctccatc tacatcaact cacgcagcgt cttcctgcgc      1380
accgaccagc ccgagggccg ctatgtcatc atccccacaa ccttcgagcc aggccacact      1440
ggcgagttcc tgctccgagt cttcactgat gtgccctcca actgccggga gctgcgcctg      1500
gatgagcccc cacacacctg ctggagctcc ctctgtggct accccagct ggtgacccag       1560 gtacatgtcc tgggagctgc tggcctcaag gactccccaa caggggctaa ctcttatgtg      1620

-continued

```
atcatcaagt gtgagggaga caaagtccgc gagcagaaac tcatctcaga agaggatctg    1680
gagcagaaac tcatctcaga agaggatctg gagcagaaac tcatctcaga agaggatctg    1740
tga                                                                  1743
```

<210> SEQ ID NO 9
<211> LENGTH: 580
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Phe Ser Cys Val Lys Pro Tyr Glu Asp Gln Asn Tyr Ser Ala Leu
1               5                   10                  15

Arg Arg Asp Cys Arg Arg Lys Val Leu Phe Glu Asp Pro Leu Phe
            20                  25                  30

Pro Ala Thr Asp Asp Ser Leu Tyr Tyr Lys Gly Thr Pro Gly Pro Ala
        35                  40                  45

Val Arg Trp Lys Arg Pro Lys Gly Ile Cys Glu Asp Pro Arg Leu Phe
    50                  55                  60

Val Asp Gly Ile Ser Ser His Asp Leu His Gln Gly Gln Val Gly Asn
65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asp Pro Glu
            100                 105                 110

Lys Pro Asn Ala Tyr Ala Gly Ile Phe His Phe His Phe Trp Arg Phe
        115                 120                 125

Gly Glu Trp Val Asp Val Val Ile Asp Asp Arg Leu Pro Thr Val Asn
    130                 135                 140

Asn Gln Leu Ile Tyr Cys His Ser Asn Ser Arg Asn Glu Phe Trp Cys
145                 150                 155                 160

Ala Leu Val Glu Lys Ala Tyr Ala Lys Leu Ala Gly Cys Tyr Gln Ala
                165                 170                 175

Leu Asp Gly Gly Asn Thr Ala Asp Ala Leu Val Asp Phe Thr Gly Gly
            180                 185                 190

Val Ser Glu Pro Ile Asp Leu Thr Glu Gly Asp Phe Ala Asn Asp Glu
        195                 200                 205

Thr Lys Arg Asn Gln Leu Phe Glu Arg Met Leu Lys Val His Ser Arg
    210                 215                 220

Gly Gly Leu Ile Ser Ala Ser Ile Lys Ala Val Thr Ala Ala Asp Met
225                 230                 235                 240

Glu Ala Arg Leu Ala Cys Gly Leu Val Lys Gly His Ala Tyr Ala Val
                245                 250                 255

Thr Asp Val Arg Lys Val Arg Leu Gly His Gly Leu Leu Ala Phe Phe
            260                 265                 270

Lys Ser Glu Lys Leu Asp Met Ile Arg Leu Arg Asn Pro Trp Gly Glu
        275                 280                 285

Arg Glu Trp Asn Gly Pro Trp Ser Asp Thr Ser Glu Glu Trp Gln Lys
    290                 295                 300

Val Ser Lys Ser Glu Arg Glu Lys Met Gly Val Thr Val Gln Asp Asp
305                 310                 315                 320

Gly Glu Phe Trp Met Thr Phe Glu Asp Val Cys Arg Tyr Phe Thr Asp
```

```
                    325                 330                 335
Ile Ile Lys Cys Arg Val Ile Asn Thr Ser His Leu Ser Ile His Lys
                340                 345                 350
Thr Trp Glu Glu Ala Arg Leu His Gly Ala Trp Thr Leu His Glu Asp
            355                 360                 365
Pro Arg Gln Asn Arg Gly Gly Cys Ile Asn His Lys Asp Thr Phe
        370                 375                 380
Phe Gln Asn Pro Gln Tyr Ile Phe Glu Val Lys Lys Pro Glu Asp Glu
385                 390                 395                 400
Val Leu Ile Cys Ile Gln Gln Arg Pro Lys Arg Ser Thr Arg Arg Glu
                405                 410                 415
Gly Lys Gly Glu Asn Leu Ala Ile Gly Phe Asp Ile Tyr Lys Val Glu
            420                 425                 430
Glu Asn Arg Gln Tyr Arg Met His Ser Leu Gln His Lys Ala Ala Ser
        435                 440                 445
Ser Ile Tyr Ile Asn Ser Arg Ser Val Phe Leu Arg Thr Asp Gln Pro
450                 455                 460
Glu Gly Arg Tyr Val Ile Ile Pro Thr Thr Phe Glu Pro Gly His Thr
465                 470                 475                 480
Gly Glu Phe Leu Leu Arg Val Phe Thr Asp Val Pro Ser Asn Cys Arg
                485                 490                 495
Glu Leu Arg Leu Asp Glu Pro His Thr Cys Trp Ser Ser Leu Cys
            500                 505                 510
Gly Tyr Pro Gln Leu Val Thr Gln Val His Val Leu Gly Ala Ala Gly
        515                 520                 525
Leu Lys Asp Ser Pro Thr Gly Ala Asn Ser Tyr Val Ile Ile Lys Cys
530                 535                 540
Glu Gly Asp Lys Val Arg Glu Gln Lys Leu Ile Ser Glu Glu Asp Leu
545                 550                 555                 560
Glu Gln Lys Leu Ile Ser Glu Glu Asp Leu Glu Gln Lys Leu Ile Ser
                565                 570                 575
Glu Glu Asp Leu
            580

<210> SEQ ID NO 10
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atgttctcgt gtgtgaagcc ctatgaggac cagaactact cagccctgag gcgggactgc        60
cggcgcagga aggtgctctt cgaggacccc ctcttccccg ccactgacga ctcactctac       120
tataagggca cgccggggcc cgccgtcagg tggaagcgac ccaagggcat ctgcgaggac       180
ccccgcctct ttgtggatgg catcagctcc cacgacctgc accagggcca ggtgggcaac       240
tgctggtttg tggcagcctg ctcgtcactt gcctcccggg agtcgctgtg gcaaaaggtc       300
gagcagaaac tcatctcaga agaggatctg gagcagaaac tcatctcaga agaggatctg       360
gagcagaaac tcatctcaga agaggatctg tga                                    393

<210> SEQ ID NO 11
<211> LENGTH: 130
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 11

```
Met Phe Ser Cys Val Lys Pro Tyr Glu Asp Gln Asn Tyr Ser Ala Leu
1               5                   10                  15
Arg Arg Asp Cys Arg Arg Lys Val Leu Phe Glu Asp Pro Leu Phe
            20                  25                  30
Pro Ala Thr Asp Asp Ser Leu Tyr Tyr Lys Gly Thr Pro Gly Pro Ala
        35                  40                  45
Val Arg Trp Lys Arg Pro Lys Gly Ile Cys Glu Asp Pro Arg Leu Phe
    50                  55                  60
Val Asp Gly Ile Ser Ser His Asp Leu His Gln Gly Gln Val Gly Asn
65                  70                  75                  80
Cys Trp Phe Val Ala Ala Cys Ser Ser Leu Ala Ser Arg Glu Ser Leu
                85                  90                  95
Trp Gln Lys Val Glu Gln Lys Leu Ile Ser Glu Glu Asp Leu Glu Gln
            100                 105                 110
Lys Leu Ile Ser Glu Glu Asp Leu Glu Gln Lys Leu Ile Ser Glu Glu
        115                 120                 125
Asp Leu
    130
```

<210> SEQ ID NO 12
<211> LENGTH: 1047
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

| | | | |
|---|---|---|---|
| ctcttcgagg acccectctt ccccgccact gacgactcac tctactataa gggcacgccg | | | 60 |
| gggcccgccg tcaggtggaa gcgacccaag ggcatctgcg aggaccccg cctctttgtg | | | 120 |
| gatggcatca gctcccacga cctgcaccag gccaggtgg gcaactgctg gtttgtggca | | | 180 |
| gcctgctcgt cacttgcctc ccgggagtcg ctgtggcaaa aggtcatccc agactggaag | | | 240 |
| gagcaggaat gggaccccga aaagcccaac gcctacgcgg gcatcttcca cttccacttc | | | 300 |
| tggcgcttcg gggaatgggt ggacgtggtc atcgatgacc ggctgcccac agtcaacaac | | | 360 |
| cagctcatct actgccactc caactcccgc aatgagtttt ggtgcgccct agtggagaag | | | 420 |
| gcctatgcca aactggcagg ctgttaccag gccctggatg gaggcaacac agcagacgca | | | 480 |
| ctggtggact tcacgggtgg tgtttctgag cccatcgacc tgaccgaggg tgactttgcc | | | 540 |
| aacgatgaga ctaagaggaa ccagctcttt gagcgcatgt taaggtgca cagccggggc | | | 600 |
| ggcctcatca gtgcctccat caaggcagtg acagcagctg acatggaggc ccgcctggcg | | | 660 |
| tgcggcctgg taagggcca cgcatacgcc gtcactgatg tgcgcaaggt gcgcctgggc | | | 720 |
| cacggcctac tggccttctt caagtcagag aagttggaca tgatccgcct gcgcaacccc | | | 780 |
| tggggcgagc gggagtggaa cgggccctgg agtgacacct cggaggagtg cagaaagtg | | | 840 |
| agcaagagtg agcgggagaa gatgggtgtg accgtgcagg acgacggtga gttctggatg | | | 900 |
| accttcgagg acgtgtgccg gtacttcacg gacatcatca gtgccgcgt gatcgagcag | | | 960 |
| aaactcatct cagaagagga tctggagcag aaactcatct cagaagagga tctggagcag | | | 1020 | aaactcatct cagaagagga tctgtga 1047

```
<210> SEQ ID NO 13
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

| | | | | | | | | | | | | | | | |
|---|---|---|---|---|---|---|---|---|---|---|---|---|---|---|---|
| Leu | Phe | Glu | Asp | Pro | Leu | Phe | Pro | Ala | Thr | Asp | Asp | Ser | Leu | Tyr | Tyr |
| 1 | | | | 5 | | | | | 10 | | | | | 15 | |
| Lys | Gly | Thr | Pro | Gly | Pro | Ala | Val | Arg | Trp | Lys | Arg | Pro | Lys | Gly | Ile |
| | | | 20 | | | | | 25 | | | | | 30 | | |
| Cys | Glu | Asp | Pro | Arg | Leu | Phe | Val | Asp | Gly | Ile | Ser | Ser | His | Asp | Leu |
| | | 35 | | | | | 40 | | | | | 45 | | | |
| His | Gln | Gly | Gln | Val | Gly | Asn | Cys | Trp | Phe | Val | Ala | Ala | Cys | Ser | Ser |
| | 50 | | | | | 55 | | | | | 60 | | | | |
| Leu | Ala | Ser | Arg | Glu | Ser | Leu | Trp | Gln | Lys | Val | Ile | Pro | Asp | Trp | Lys |
| 65 | | | | | 70 | | | | | 75 | | | | | 80 |
| Glu | Gln | Glu | Trp | Asp | Pro | Glu | Lys | Pro | Asn | Ala | Tyr | Ala | Gly | Ile | Phe |
| | | | | 85 | | | | | 90 | | | | | 95 | |
| His | Phe | His | Phe | Trp | Arg | Phe | Gly | Glu | Trp | Val | Asp | Val | Val | Ile | Asp |
| | | | 100 | | | | | 105 | | | | | 110 | | |
| Asp | Arg | Leu | Pro | Thr | Val | Asn | Asn | Gln | Leu | Ile | Tyr | Cys | His | Ser | Asn |
| | | 115 | | | | | 120 | | | | | 125 | | | |
| Ser | Arg | Asn | Glu | Phe | Trp | Cys | Ala | Leu | Val | Glu | Lys | Ala | Tyr | Ala | Lys |
| | 130 | | | | | 135 | | | | | 140 | | | | |
| Leu | Ala | Gly | Cys | Tyr | Gln | Ala | Leu | Asp | Gly | Gly | Asn | Thr | Ala | Asp | Ala |
| 145 | | | | | 150 | | | | | 155 | | | | | 160 |
| Leu | Val | Asp | Phe | Thr | Gly | Gly | Val | Ser | Glu | Pro | Ile | Asp | Leu | Thr | Glu |
| | | | | 165 | | | | | 170 | | | | | 175 | |
| Gly | Asp | Phe | Ala | Asn | Asp | Glu | Thr | Lys | Arg | Asn | Gln | Leu | Phe | Glu | Arg |
| | | | 180 | | | | | 185 | | | | | 190 | | |
| Met | Leu | Lys | Val | His | Ser | Arg | Gly | Gly | Leu | Ile | Ser | Ala | Ser | Ile | Lys |
| | | 195 | | | | | 200 | | | | | 205 | | | |
| Ala | Val | Thr | Ala | Ala | Asp | Met | Glu | Ala | Arg | Leu | Ala | Cys | Gly | Leu | Val |
| | 210 | | | | | 215 | | | | | 220 | | | | |
| Lys | Gly | His | Ala | Tyr | Ala | Val | Thr | Asp | Val | Arg | Lys | Val | Arg | Leu | Gly |
| 225 | | | | | 230 | | | | | 235 | | | | | 240 |
| His | Gly | Leu | Leu | Ala | Phe | Phe | Lys | Ser | Glu | Lys | Leu | Asp | Met | Ile | Arg |
| | | | | 245 | | | | | 250 | | | | | 255 | |
| Leu | Arg | Asn | Pro | Trp | Gly | Glu | Arg | Glu | Trp | Asn | Gly | Pro | Trp | Ser | Asp |
| | | | 260 | | | | | 265 | | | | | 270 | | |
| Thr | Ser | Glu | Glu | Trp | Gln | Lys | Val | Ser | Lys | Ser | Glu | Arg | Glu | Lys | Met |
| | | 275 | | | | | 280 | | | | | 285 | | | |
| Gly | Val | Thr | Val | Gln | Asp | Asp | Gly | Glu | Phe | Trp | Met | Thr | Phe | Glu | Asp |
| | 290 | | | | | 295 | | | | | 300 | | | | |
| Val | Cys | Arg | Tyr | Phe | Thr | Asp | Ile | Ile | Lys | Cys | Arg | Val | Ile | Glu | Gln |
| 305 | | | | | 310 | | | | | 315 | | | | | 320 |
| Lys | Leu | Ile | Ser | Glu | Glu | Asp | Leu | Gln | Lys | Leu | Ile | Ser | Glu | Glu | |
| | | | | 325 | | | | | 330 | | | | | 335 | |
| Asp | Leu | Glu | Gln | Lys | Leu | Ile | Ser | Glu | Glu | Asp | Leu | | | | |
| | | | 340 | | | | | 345 | | | | | | | |

<210> SEQ ID NO 14
<211> LENGTH: 813
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
aacacagcag acgcactggt ggacttcacg ggtggtgttt ctgagcccat cgacctgacc      60
gagggtgact ttgccaacga tgagactaag aggaaccagc tctttgagcg catgttaaag     120
gtgcacagcc ggggcggcct catcagtgcc tccatcaagg cagtgacagc agctgacatg     180
gaggcccgcc tggcgtgcgg cctggtaaag ggccacgcat acgccgtcac tgatgtgcgc     240
aaggtgcgcc tggccacgg cctactggcc ttcttcaagt cagagaagtt ggacatgatc     300
cgcctgcgca accctgggg cgagcgggag tggaacgggc cctggagtga cacctcggag     360
gagtggcaga agtgagcaa gagtgagcgg gagaagatgg gtgtgaccgt gcaggacgac     420
ggtgagttct ggatgacctt cgaggacgtg tgccggtact tcacggacat catcaagtgc     480
cgcgtgatca acacatccca cctgagcatc acaagacgt gggaggaggc ccggctgcat     540
ggcgcctgga cgctgcatga ggacccgcga cagaaccgcg gtggcggctg catcaaccac     600
aaggacacct tcttccagaa cccacagtac atcttcgaag tcaagaagcc agaagatgaa     660
gtcctgatct gcatccagca gcggccaaag cggtctacgc gccgggaggg caagggtgag     720
gagcagaaac tcatctcaga agaggatctg gagcagaaac tcatctcaga agaggatctg     780
gagcagaaac tcatctcaga agaggatctg tga                                  813
```

<210> SEQ ID NO 15
<211> LENGTH: 270
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Asn Thr Ala Asp Ala Leu Val Asp Phe Thr Gly Gly Val Ser Glu Pro
1               5                   10                  15

Ile Asp Leu Thr Glu Gly Asp Phe Ala Asn Asp Glu Thr Lys Arg Asn
            20                  25                  30

Gln Leu Phe Glu Arg Met Leu Lys Val His Ser Arg Gly Gly Leu Ile
        35                  40                  45

Ser Ala Ser Ile Lys Ala Val Thr Ala Ala Asp Met Glu Ala Arg Leu
    50                  55                  60

Ala Cys Gly Leu Val Lys Gly His Ala Tyr Ala Val Thr Asp Val Arg
65                  70                  75                  80

Lys Val Arg Leu Gly His Gly Leu Leu Ala Phe Phe Lys Ser Glu Lys
                85                  90                  95

Leu Asp Met Ile Arg Leu Arg Asn Pro Trp Gly Glu Arg Glu Trp Asn
            100                 105                 110

Gly Pro Trp Ser Asp Thr Ser Glu Glu Trp Gln Lys Val Ser Lys Ser
        115                 120                 125

Glu Arg Glu Lys Met Gly Val Thr Val Gln Asp Gly Glu Phe Trp
    130                 135                 140

Met Thr Phe Glu Asp Val Cys Arg Tyr Phe Thr Asp Ile Ile Lys Cys
145                 150                 155                 160
```

Arg Val Ile Asn Thr Ser His Leu Ser Ile His Lys Thr Trp Glu Glu
            165                 170                 175

Ala Arg Leu His Gly Ala Trp Thr Leu His Glu Asp Pro Arg Gln Asn
        180                 185                 190

Arg Gly Gly Gly Cys Ile Asn His Lys Asp Thr Phe Phe Gln Asn Pro
    195                 200                 205

Gln Tyr Ile Phe Glu Val Lys Lys Pro Glu Asp Glu Val Leu Ile Cys
    210                 215                 220

Ile Gln Gln Arg Pro Lys Arg Ser Thr Arg Arg Gly Lys Gly Glu
225                 230                 235                 240

Glu Gln Lys Leu Ile Ser Glu Glu Asp Leu Gln Lys Leu Ile Ser
            245                 250                 255

Glu Glu Asp Leu Glu Gln Lys Leu Ile Ser Glu Glu Asp Leu
            260                 265                 270

<210> SEQ ID NO 16
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
aacctggcca ttggctttga catctacaag gtggaggaga accgccagta ccgcatgcac      60
agcctgcagc acaaggccgc cagctccatc tacatcaact cacgcagcgt cttcctgcgc     120
accgaccagc ccgagggccg ctatgtcatc atccccacaa ccttcgagcc aggccacact     180
ggcgagttcc tgctccgagt cttcactgat gtgccctcca actgccggga gctgcgcctg     240
gatgagcccc cacacacctg ctggagctcc ctctgtggct accccagct ggtgacccag      300 gtacatgtcc tggagctgc tggcctcaag gactccccaa caggggctaa ctcttatgtg      360
atcatcaagt gtgagggaga caaagtccgc tcggctgtgc agaagggcac ctccacacca     420
gagcagaaac tcatctcaga agaggatctg gagcagaaac tcatctcaga agaggatctg     480
gagcagaaac tcatctcaga agaggatctg tga                                   513

<210> SEQ ID NO 17
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asn Leu Ala Ile Gly Phe Asp Ile Tyr Lys Val Glu Glu Asn Arg Gln
1               5                   10                  15

Tyr Arg Met His Ser Leu Gln His Lys Ala Ala Ser Ser Ile Tyr Ile
            20                  25                  30

Asn Ser Arg Ser Val Phe Leu Arg Thr Asp Gln Pro Glu Gly Arg Tyr
        35                  40                  45

Val Ile Ile Pro Thr Thr Phe Glu Pro Gly His Thr Gly Glu Phe Leu
    50                  55                  60

Leu Arg Val Phe Thr Asp Val Pro Ser Asn Cys Arg Glu Leu Arg Leu
65                  70                  75                  80

Asp Glu Pro Pro His Thr Cys Trp Ser Ser Leu Cys Gly Tyr Pro Gln
            85                  90                  95

Leu Val Thr Gln Val His Val Leu Gly Ala Ala Gly Leu Lys Asp Ser
            100                 105                 110

Pro Thr Gly Ala Asn Ser Tyr Val Ile Ile Lys Cys Glu Gly Asp Lys
        115                 120                 125

Val Arg Ser Ala Val Gln Lys Gly Thr Ser Thr Pro Glu Gln Lys Leu
    130                 135                 140

Ile Ser Glu Glu Asp Leu Glu Gln Lys Leu Ile Ser Glu Glu Asp Leu
145                 150                 155                 160

Glu Gln Lys Leu Ile Ser Glu Glu Asp Leu
                165                 170

<210> SEQ ID NO 18
<211> LENGTH: 16
<212> TYPE: PRT
<213> ORGANISM: Unknown
<220> FEATURE:
<223> OTHER INFORMATION: Description of Unknown:
      PDGFB sequence

<400> SEQUENCE: 18

Lys Ile Glu Ile Val Arg Lys Lys Pro Ile Phe Lys Lys Ala Thr Val
1               5                   10                  15

<210> SEQ ID NO 19
<211> LENGTH: 11
<212> TYPE: PRT
<213> ORGANISM: Unknown
<220> FEATURE:
<223> OTHER INFORMATION: Description of Unknown:
      IRX3 sequence

<400> SEQUENCE: 19

Ala Ala Gly His Pro Ala Ala Ala Ala Ala Phe
1               5                   10

<210> SEQ ID NO 20
<211> LENGTH: 21
<212> TYPE: PRT
<213> ORGANISM: Homo sapiens

<400> SEQUENCE: 20

Arg Gln Asn Arg Gly Gly Gly Cys Ile Asn His Lys Asp Thr Phe Phe
1               5                   10                  15

Gln Asn Pro Gln Tyr
            20

<210> SEQ ID NO 21
<211> LENGTH: 21
<212> TYPE: PRT
<213> ORGANISM: Homo sapiens

<400> SEQUENCE: 21

Tyr Ile Phe Glu Val Lys Lys Pro Glu Asp Glu Val Leu Ile Cys Ile
1               5                   10                  15

Gln Gln Arg Pro Lys
            20

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Glu Pro Leu Phe Ala Glu Arg Lys
1               5

<210> SEQ ID NO 23
<211> LENGTH: 11
<212> TYPE: PRT
<213> ORGANISM: Homo sapiens

<400> SEQUENCE: 23

Arg Gln Asn Arg Gly Gly Gly Cys Ile Asn His
1               5                   10

<210> SEQ ID NO 24
<211> LENGTH: 22
<212> TYPE: PRT
<213> ORGANISM: Homo sapiens

<400> SEQUENCE: 24

Arg Gly Ser Thr Ala Gly Gly Cys Arg Asn Tyr Pro Ala Thr Phe Trp
1               5                   10                  15

Val Asn Pro Gln Phe Lys
            20

<210> SEQ ID NO 25
<211> LENGTH: 22
<212> TYPE: PRT
<213> ORGANISM: Homo sapiens

<400> SEQUENCE: 25

Arg Gly Ser Thr Ala Gly Gly Cys Arg Asn Tyr Pro Asn Thr Phe Trp
1               5                   10                  15

Met Asn Pro Gln Tyr Leu
            20

<210> SEQ ID NO 26
<211> LENGTH: 22
<212> TYPE: PRT
<213> ORGANISM: Homo sapiens

<400> SEQUENCE: 26

Arg Gly Cys Ser Ala Gly Gly Cys Arg Asn Phe Pro Asp Thr Phe Trp
1               5                   10                  15

Thr Asn Pro Gln Tyr Arg
            20

<210> SEQ ID NO 27
<211> LENGTH: 22
<212> TYPE: PRT
<213> ORGANISM: Homo sapiens

<400> SEQUENCE: 27

Arg Gln Asn Arg Gly Gly Gly Cys Ile Asn His Lys Asp Thr Phe Phe
1               5                   10                  15

Gln Asn Pro Gln Tyr Ile
            20

<210> SEQ ID NO 28
<211> LENGTH: 22
<212> TYPE: PRT
<213> ORGANISM: Homo sapiens

```
<400> SEQUENCE: 28

Leu Met Asn Arg Ser Gly Gly Cys Tyr Asn Arg Asp Thr Phe Leu
1               5                   10                  15

Gln Asn Pro Gln Tyr Ile
            20

<210> SEQ ID NO 29
<211> LENGTH: 21
<212> TYPE: PRT
<213> ORGANISM: Homo sapiens

<400> SEQUENCE: 29

Gly Ser Thr Ala Gly Gly Cys Gln Asn Tyr Pro Ala Thr Tyr Trp Thr
1               5                   10                  15

Asn Pro Gln Phe Lys
            20

<210> SEQ ID NO 30
<211> LENGTH: 21
<212> TYPE: PRT
<213> ORGANISM: Homo sapiens

<400> SEQUENCE: 30

Gly Ser Thr Ala Gly Gly Cys Arg Asn Phe Leu Asp Thr Phe Trp Thr
1               5                   10                  15

Asn Pro Gln Ile Lys
            20

<210> SEQ ID NO 31
<211> LENGTH: 22
<212> TYPE: PRT
<213> ORGANISM: Homo sapiens

<400> SEQUENCE: 31

Arg Gly Ser Ser Ala Gly Gly Cys Arg Asn His Pro Gly Thr Phe Trp
1               5                   10                  15

Thr Asn Pro Gln Phe Lys
            20

<210> SEQ ID NO 32
<211> LENGTH: 22
<212> TYPE: PRT
<213> ORGANISM: Homo sapiens

<400> SEQUENCE: 32

Arg Gly Phe Asn Ser Gly Gly Ser Gln Pro Asn Ala Glu Thr Phe Trp
1               5                   10                  15

Thr Asn Pro Gln Phe Arg
            20

<210> SEQ ID NO 33
<211> LENGTH: 23
<212> TYPE: PRT
<213> ORGANISM: Homo sapiens

<400> SEQUENCE: 33

Leu Gly Asn Thr Ala Gly Gly Pro Arg Asn Asp Ala Gln Phe Asn Phe
1               5                   10                  15

Ser Val Gln Glu Pro Met Glu
            20
```

<210> SEQ ID NO 34
<211> LENGTH: 23
<212> TYPE: PRT
<213> ORGANISM: Homo sapiens

<400> SEQUENCE: 34

Lys Arg Ser Thr Ala Gly Gly Gln Arg Gln Leu Leu Gln Asp Thr Phe
1               5                   10                  15

Trp Lys Asn Pro Gln Phe Leu
            20

<210> SEQ ID NO 35
<211> LENGTH: 11
<212> TYPE: PRT
<213> ORGANISM: Homo sapiens

<400> SEQUENCE: 35

Arg Gly Ser Thr Ala Gly Gly Cys Arg Asn Tyr
1               5                   10

<210> SEQ ID NO 36
<211> LENGTH: 11
<212> TYPE: PRT
<213> ORGANISM: Homo sapiens

<400> SEQUENCE: 36

Arg Gly Cys Ser Ala Gly Gly Cys Arg Asn Phe
1               5                   10

<210> SEQ ID NO 37
<211> LENGTH: 11
<212> TYPE: PRT
<213> ORGANISM: Homo sapiens

<400> SEQUENCE: 37

Leu Met Asn Arg Ser Gly Gly Cys Tyr Asn Asn
1               5                   10

<210> SEQ ID NO 38
<211> LENGTH: 10
<212> TYPE: PRT
<213> ORGANISM: Homo sapiens

<400> SEQUENCE: 38

Gly Gln Ser Ala Gly Gly Cys Gly Asn Phe
1               5                   10

<210> SEQ ID NO 39
<211> LENGTH: 11
<212> TYPE: PRT
<213> ORGANISM: Homo sapiens

<400> SEQUENCE: 39

Gly Ser Thr Ala Gly Gly Cys Arg Asn Phe Leu
1               5                   10

<210> SEQ ID NO 40
<211> LENGTH: 10
<212> TYPE: PRT
<213> ORGANISM: Homo sapiens

<400> SEQUENCE: 40

Gly Gln Ser Ala Gly Gly Cys Arg Asn Asn
1               5                   10

```
<210> SEQ ID NO 41
<211> LENGTH: 11
<212> TYPE: PRT
<213> ORGANISM: Homo sapiens

<400> SEQUENCE: 41

Arg Gly Phe Asn Ser Gly Gly Ser Gln Pro Asn
1               5                   10

<210> SEQ ID NO 42
<211> LENGTH: 11
<212> TYPE: PRT
<213> ORGANISM: Homo sapiens

<400> SEQUENCE: 42

Leu Gly Asn Thr Ala Gly Gly Pro Arg Asn Asp
1               5                   10

<210> SEQ ID NO 43
<211> LENGTH: 11
<212> TYPE: PRT
<213> ORGANISM: Homo sapiens

<400> SEQUENCE: 43

Lys Arg Ser Thr Ala Gly Gly Gln Arg Gln Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: N-Me-Gly

<400> SEQUENCE: 44

Arg Gln Asn Arg Gly Gly Gly Cys Ile Asn His
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: N-Me-Gly
<220> FEATURE:
<221> NAME/KEY: MOD_RES
<222> LOCATION: (8)..(8)
<223> OTHER INFORMATION: Acm-Cys

<400> SEQUENCE: 45

Arg Gln Asn Arg Gly Gly Gly Cys Ile Asn His
1               5                   10
```